US008647644B1

(12) United States Patent (10) Patent No.: US 8,647,644 B1
Torney et al. (45) Date of Patent: Feb. 11, 2014

(54) METHODS OF USING CAPPED MESOPOROUS SILICATES

(75) Inventors: Francois Jean George Torney, Beaumont (FR); Kan Wang, Ames, IA (US); Victor Shang-Yi Lin, Ames, IA (US); Brian G. Trewyn, Ames, IA (US); Supratim Giri, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 779 days.

(21) Appl. No.: 11/788,147

(22) Filed: Apr. 19, 2007

Related U.S. Application Data

(60) Provisional application No. 60/793,339, filed on Apr. 19, 2006.

(51) Int. Cl.
    *A61K 9/00* (2006.01)
(52) U.S. Cl.
    USPC .......................................... 424/400; 424/489
(58) Field of Classification Search
    USPC ......................................................... 424/400
    See application file for complete search history.

(56) References Cited

U.S. PATENT DOCUMENTS

| | | |
|---|---|---|
| 4,062,965 A | 12/1977 | Holtschmidt et al. |
| 4,522,806 A | 6/1985 | Muhlemann et al. |
| 5,104,515 A | 4/1992 | Chu et al. |
| 5,110,572 A | 5/1992 | Calabro et al. |
| 5,143,879 A | 9/1992 | Whitehurst |
| 5,145,816 A | 9/1992 | Beck et al. |
| 5,156,828 A | 10/1992 | Degnan et al. |
| 5,156,829 A | 10/1992 | McCullen et al. |
| 5,198,203 A | 3/1993 | Kresge et al. |
| 5,364,797 A | 11/1994 | Olson et al. |
| 5,380,947 A | 1/1995 | Chen et al. |
| 5,629,282 A | 5/1997 | Bhakoo |
| 5,922,635 A | 7/1999 | Olah et al. |
| 5,965,264 A | 10/1999 | Barenberg et al. |
| 6,475,497 B1 | 11/2002 | Rajaiah et al. |
| 6,696,258 B1 | 2/2004 | Wei et al. |
| 6,723,862 B2 | 4/2004 | Shuguang et al. |
| 6,863,942 B2 | 3/2005 | Ren et al. |
| 6,969,693 B2 | 11/2005 | Sauvage et al. |
| 7,195,780 B2 | 3/2007 | Dennis et al. |
| 7,563,451 B2 | 7/2009 | Lin et al. |
| 8,246,999 B2 | 8/2012 | Lin et al. |
| 2002/0164380 A1 | 11/2002 | Ma et al. |
| 2003/0157330 A1 | 8/2003 | Ostafin et al. |
| 2004/0213996 A1 | 10/2004 | Fujiwara et al. |
| 2006/0018966 A1 | 1/2006 | Lin et al. |
| 2006/0120955 A1 | 6/2006 | Miyata |
| 2006/0154069 A1 | 7/2006 | Lin et al. |
| 2009/0104700 A1 | 4/2009 | Samuel et al. |
| 2009/0252811 A1 | 10/2009 | Lin et al. |
| 2012/0244569 A1 | 9/2012 | Samuel et al. |

FOREIGN PATENT DOCUMENTS

| | | |
|---|---|---|
| EP | 2195438 B1 | 1/2013 |
| WO | WO-2005/009602 A2 | 2/2005 |
| WO | WO-2006/034239 A2 | 3/2006 |

OTHER PUBLICATIONS

Xu H et al. J. Biomed Mater Res A. "Room-temperature preparation and characterization of poly (ethylene glycol)-coated silica nanoparticles for biomedical applications" 2003 15;66(4), pp. 870-879).*
Christou et al., Plant Physiol. Stable Transformation of Soybean Callus by DNA-Coated Gold Particles ,1988 87, pp. 671-674.*
"Adhesive-Types of Adhesive Bonding", [online]. © 2007 Net Industries. [archived Nov. 2, 2007]. Retrieved from the Internet: <URL: http://science.jrank.org/pages/87/Adhesive-Types-adhesive-bonding.html>, (2007), 1 pg.
"U.S. Appl. No. 10/830,479, Response filed Oct. 1, 2008 to Final Office Action mailed Aug. 1, 2008", 11 pgs.
"U.S. Appl. No. 10/830,479, Response filed Nov. 25, 2008 to Final Office Action mailed Aug. 1, 2008", 12 pgs.
"U.S. Appl. No. 10/830,479, Advisory Action mailed Oct. 31, 2008", 3 pgs.
"U.S. Appl. No. 10/830,479, Supplemental Notice of Allowability mailed Feb. 17, 2009", 2 pgs.
"U.S. Appl. No. 10/830,479, Notice of Allowance mailed Jan. 9, 2009", 4 pgs.
"U.S. Appl. No. 10/830,479, Non-Final Office Action mailed Nov. 9, 2007", 9 pgs.
"U.S. Appl. No. 10/830,479, Response filed Apr. 9, 2008 to Non-Final Ofice Action mailed Nov. 9, 2007", 14 pgs.
"U.S. Appl. No. 10/830,479, Final Office Action mailed Aug. 1, 2008", 8 pgs.
"U.S. Appl. No. 10/830,479, Response filed Oct. 8, 2007 to Restriction Requirement mailed Aug. 8, 2007", 8 pgs.
"U.S. Appl. No. 10/830,479, Restriction Requirement Received mailed Aug. 8, 2007", 8 pgs.
"U.S. Appl. No. 10/945,545, Response filed Oct. 20, 2008 to Non Final Office Action mailed Jun. 20, 2008", 15 pgs.
"U.S. Appl. No. 10/945,545, Non-Final Office Action mailed Jun. 20, 2008", 21 pgs.
"U.S. Appl. No. 10/945,545, Final Office Action mailed Jan. 28, 2009", 19 pgs.
"International Application Serial No. PCT/US04/23468, International Search Report mailed Apr. 11, 2006", 2 pgs.
"International Application Serial No. PCT/USO4/23468, Written Opinion mailed Apr. 11, 2006", 5 pgs.
"International Application Serial No. PCT/US05/33578, International Search Report mailed Jun. 16, 2006", 3 pgs.
"International Application Serial No. PCT/US05/33578, Written Opinion mailed Jun. 16, 2006", 6 pgs.
"This Issue Summary", *Nature Nanotechnoloov*, 2(5), (May 2007), 1 pg.
Anderson, M. T., et al., "Effect of Methanol Concentration on CTAB Micellization and on the Formation of Surfactant-Templated Silica (STS)", *Chemistry of Materials*, 10, (1998), 1490-1500.

(Continued)

*Primary Examiner* — James Rogers
(74) *Attorney, Agent, or Firm* — Schwegman Lundberg & Woessner, P.A.

(57) ABSTRACT

The invention provides an article having a mesoporous silicate matrix, such as a particle, having one or more pores; and one or more releasable caps obstructing one or more of the pores for delivery of one or more agents to plant cells or other chlorophyll containing cells, or fungi.

24 Claims, 13 Drawing Sheets

(56) References Cited

OTHER PUBLICATIONS

Anwander, R., et al., "Enhanced catalytic activity of MCM-41-grafted aluminum isopropoxide in MPV reductions", *Chem. Commun.*, (1998), 1811-1812.

Aughenbaugh, W., et al., "Silica sol-gel for the controlled release of antibiotics. II. The effect of synthesis parameters on the in vitro release kinetics of vancomycin", *J. Biomed. Mater. Res.*, 57(2), (2001), 321-326.

Babonneau, F., et al., "Structural characterization of organically-modified porous silicates synthesized using $CTA^+$ surfactant and acidic conditions", *Journal of Materials Chemistry*, 9(1), (1999), 175-178.

Bagshaw, S. A., et al., "Templating of Mesoporous Molecular Sieves by Nonionic Polyethylene Oxide Surfactants", *Science*, 269(5228), (1995), 1242-1244.

Baker, Jr., J. R., et al., "The Synthesis and Testing of Anti-Cancer Therapeutic Nanodevices", *Biomedical Microdevices*, 3(1), (2001), 61-69.

Beck, J. S., et al., "A New Family of Mesoporous Molecular Sieves Prepared With Liquid Crystal Templates", *Journal of the American Chemical Society*, 114(27), (1992), 10834-10843.

Brown, J., et al., "Selective adsorption of $Hg^{2+}$ by thiol-functionalized nanoporous silica", *Chem. Commun.*, (1999), 69-70.

Burleigh, M. C., et al., "Amine-Functionalized Periodic Mesoporous Organosilicas", *Chemicals of Materials*, 13(12), (2001), 4760-4766.

Burleigh, M. C., et al., "Direct Synthesis of Periodic Mesoporous Organosilicas: Functional Incorporation by Co-condensation with Organosilanes", *The Journal of Physical Chemistry B*, 105(41), (2001), 9935-9942.

Burleigh, M. C., et al., "Imprinted Polysilsesquioxanes for the Enhanced Recognition of Metal Ions", *Chemistry of Materials*, 13(8), (2001), 2537-2546.

Cai, Q., et al., "Dilute Solution Routes to Various Controllable Morphologies of MCM-41 Silica with a Basic Medium", *Chemistry of Materials*, 13(2), (2001), 258-263.

Colvin, V. L., et al., "Semiconductor nanocrystals covalently bound to metal surfaces with self-assembled monolayers", *Journal of the American Chemical Society*, 114(13), (1992), 5221-5230.

Corma, A., "From Microporous to Mesoporous Molecular Sieve Materials and Their Use in Catalysis", *Chemical Reviews*, 97(6), (1997), 2373-2420.

Dai, S., et al., "Imprint Coating: A Novel Synthesis of Selective Functionalized Ordered Mesoporous Sorbents", *Angew. Chem. Int. Ed.*, 38(9), (1999), 1235-1239.

Davis, M. E., "Ordered porous materials for emerging applications", *Nature*, 417, (2002), 813-821.

Denning, J., et al., "Gene transfer into eukaryotic cells using activated polyamidoamine dendrimers", *Reviews in Molecular Biotechnology*, 90, (2002), 339-347.

Descalzo, A. B., et al., "A New Approach to Chemosensors for Anions Using MCM-41 Grafted with Amino Groups", *Advanced Materials*, 14(No. 13-14), (2002), 966-969.

Diaz, J. F., et al., "Enzyme immobolization in MCM-41 molecular sieve", *Journal of Molecular Catalysis B: Enzymatic 2*, (1996), 115-126.

Ebright, Y. W., et al., "S-[2-(4-Azidosalicylamido)ethylthio]-2-thiopyridine: Radioiodinatable, Cleavable, Photoactivatible Cross-Linking Agent", *Bioconjugate Chemistry*, 7(3), (1996), 380-384.

Esfand, R., et al., "Poly(amidoamine) (PAMAM) dendrimers: from biomimicry to drug delivery and biomedical applications", *Drug Discovery Today*, 6(8), (2001), 427-436.

Etienne, M., et al., "Organically-modified mesoporous silica spheres with MCM-41 architecture", *New J. Chem.*, 26, (2002), 384-386.

Fan, H, et al., "Rapid prototyping of patterned functional nanostructures", *Nature*, 405(6782), (May 4, 2000), 56-60.

Feng, et al., "Functionalized Monolayers on Ordered Mesoporous Supports", *Science*, 276, (1997), 923-926.

Fowler, C. E., et al., "Covalent coupling of an organic chromophore into functionalized MCM-41 mesophases by template-directed co-condensation", *Chem. Commun.*, (1998), 1825-1826.

Fowler, C. E., et al., "Nanoscale Materials with Mesostructured Interiors", *Advanced Materials*, 13(9), (2001), 649-652.

Fowler, C. E., et al., "Synthesis and characteristics of ordered organo-silica-surfactant mesophases with functionalized MCM-41-type architecture", *Chem. Commun.*, (1997), 1769-1770.

Galbraith, D. W, "Silica breaks through in plants", *Nature Nanotechnology*, 2, (2007), 272-273.

Gruenhagen, J. A., et al., "Real-Time Imaging of Tunable Adenosine 5-Triphosphate Release from an MCM-41-Type Mesoporous Silica Nanosphere-Based Delivery System", *Applied Spectroscopy*, 59(4), (2005), 424-431.

Gryglewicz, S, "Rapeseed oil methyl esters preparation using heterogeneous catalysts", *Bioresource Technology*, 70, (1999), 249-253.

Grynkiewicz, G., et al., "A New Generation of $Ca^{2+}$ Indicators with Greatly Improved Fluorescence Properties", *The Journal of Biological Chemistry*, 260(6), (1985), 3440-3450.

Gupta, et al., "Hydrogels: from controlled release to pH-responsive drug delivery", *Drug Discovery Today*, 7(10), (2002), 569-579.

Hall, S. R., et al., "Template-directed synthesis of bi-functionalized organo-MCM-41 and phenyl-MCM-48 silica mesophases", *Chem. Commun.*, (1999), 201-202.

Han, Y.-J., et al., "Mesoporous Silicate Sequestration and Release of Proteins", *Journal of the American Chemical Society*, 121(42), (1999), 9897-9898.

He, X., et al., "Recent Advances in Synthesis and Applications of Transition Metal Containing Mesoporous Molecular Sieves", *Angew. Chem. Int. Ed.*, 41, (2002), 214-229.

He, X.-X., et al., "Bioconjugated Nanoparticles for DNA Protection from Cleavage", *Journal of the American Chemical Society*, 125(24), (2003), 7168-7169.

Hirai, T., et al., "Size-selective incorporation of CdS nanoparticles into mesoporous Silica", *The Journal of Physical Chemistry B*, 103 21 (1999), 4228-4230.

Hossain, K. Z., et al., "Intraframework Metal Ion Adsorption in Ligand-Functionalized Mesoporous Silica", *Advanced Materials*, 14(15), (2002), 1053-1056.

Huang, D.-M., et al., "Highly efficient cellular labeling of mesoporous nanoparticles in human mesenchymal stem cells: implication for stem cell tracking", *The FASEB Journal*, 19, (2005), 2014-2016.

Huh, S., et al., "Organic Functionalization and Morphology Control of Mesoporous Silicas via a Co-Condensation Synthesis Method", *Chemistry of Materials*, 15(22), (2003), 4247-4256.

Huo, Q., et al., "A New Class of Silica Cross-Linked Micellar Core-Shell Nanoparticles", *Journal of the American Chemical Society*, 128(19), (2006), 6447-6453.

Huo, Q., et al., "Room Temperature Growth of Mesoporous Silica Fibers: A New High-Surface-Area Optical Waveguide", *Adv. Mater.*, 9(12), (1997), 974-978.

Huo, Q., et al., "Surfactant Control of Phases in the Synthesis of Mesoporous Silica-Based Materials", *Chemistry of Materials*, 8(5), (1996), 1147-1160.

Inagaki, S., et al., "An Ordered Mesoporous Organosilica Hybrid Material With a Crystal-Like Wall Structure", *Nature*, 416, (2002), 304-307.

Inagaki, S., et al., "Synthesis of Highly Ordered Mesoporous Materials, FSM-16, Derived from Kanemite", *Bull. Chem. Soc. Jpn.*, 69, (1996), 1449-1457.

Jeftinija, S. D., et al., "Neuroligand-Evoked Calcium-Dependent Release of Excitatory Amino Acids from Cultured Astrocytes", *Journal of Neurochemistry*, 66, (1996), 676-684.

Jeremic, A., et al., "ATP stimulates calcium-dependent glutamate release from cultured astrocytes", *Journal of Neurochemistry*, 77, (2001), 664-675.

Kageyama, K., et al., "Extrusion Polymerization: Catalyzed Synthesis of Crystalline Linear Polyethylene Nanofibers Within a Mesoporous Silica", *Science*, 285(5436), (1999),2113-2115.

Karakassides, M. A., et al., "Synthesis and characterization of copper containing mesoporous silicas", *Journal of Materials Chemistry*, 10, (2000), 403-408.

Kawahara, et al., "Antibacterial effect of silver-zeolite on oral bacteria under anaerobic conditions", *Dental Materials*, (16(2000)), 452-455 pgs.

(56) References Cited

OTHER PUBLICATIONS

Kisler, J. M., et al., "Separation of biological molecules using mesoporous molecular sieves", *Microporous and Mesoporous Materials*, 44-45, (2001), 769-774.

Kneuer, C., et al., "A Nonviral DNA Delivery System Based on Surface Modified Silica-Nanoparticles Can Efficiently Transfect Cells in Vitro", *Bioconiuqate Chemistry*, 11(6), (200), 926-932.

Kortesuo, P., et al., "In vitro evaluation of sol-gel processed spray dried silica gel microspheres as carrier in controlled drug delivery", *International Journal of Pharamaceuticals*, 200, (2000), 223-229.

Kresge, C. T., et al., "Ordered mesoporous molecular sieves synthesized by a liquid crystal template mechanism", *Nature*, 359(6397), (1992), 710-712.

Lai, Cheng-Yu, et al., "A Mesoporous Silica Nanosphere-Based Carrier System with Chemically Removable CdS Nanoparticle Caps for Stimuli-Responsive Controlled Release of Neurotransmitters and Drug Molecules", *Journal of the American Chemical Society*, 125, (2003), 4451-4459.

Langer, R., "Polymer-controlled drug delivery systems", *Accounts of Chemical Research*, 26(10), (2002), 537-542.

Lim, M. H., et al., "Synthesis of Ordered Microporous Silicates with Organosulfur Surface Groups and Their Applications as Solid Acid Catalysts", *Chemistry of Materials*, 10(2), (1998), 467-470.

Lim, M.. H., et al., "Comparative Studies of Grafting and Direct Synthesis of Inorganic-Organic Hybrid Mesoporous Materials", *Chemistry of Materials*, 11(11), (1999), 3285-3295.

Lim, M. H, et al., "Synthesis and Characterization of a Reactive Vinyl-Functionalized MCM-41: Probing the Internal Pore Structure by a Bromination Reaction", *Journal of the American Chemical Society*, 119(17), (1997), 4090-4091.

Lin, H.-P., et al., "Structural and Morphological Control of Cationic Surfactant-Templated Mesoporous Silica", *Accounts of Chemical Research*, 35(111, (2002), 927-935.

Lin, V S, et al., "Molecular recognition inside of multifunctionalized mesoporous silicas: toward selective fluorescence detection of dopamine and glucosamine", *J Am Chem Soc.*, 123(46), (Nov. 21, 2001), 11510-11.

Lin, V. S, et al., "Oxidative Polymerization of 1,4-Diethynylbenzene into Highly Conjugated Poly(phenylene butadiynylene) within the Channels of Surface-Functionalized Mesoporous Silica & Alumina Materials", *Journal of the American Chemical Society*, 124(31), (2002), 9040-9041.

Lin, Y., et al., "Selective Sorption of Cesium Using Self-Assembled Monolayers on Mesoporous Supports", *Environmental Science & Technology*, 35(19), (2001), 3962-3966.

Liu, J., et al., "Molecular Assembly in Ordered Mesoporosity: A New Class of Highly Functional Nanoscale Materials", *The Journal of Physical Chemistry A*, 104(36), (2000), 8328-8339.

Luo, D., et al., "A self-assembled, modular DNA delivery system mediated by silica nanoparticles", *Journal of Controlled Release*, 95, (2004), 333-341.

Luo, D., et al., "Enhancement of transfection by physical concentration of DNA at the cell surface", *Nature Biotechnology*, 18, (2000), 893-895.

MaClachlan, M. J., et al., "Writing on the Wall with a New Synthetic Quill", *Chem. Eur. J.*, 6(14), (2000), 2507-2511.

Mal, N. K., et al., "Photocontrolled reversible release of guest molecules from coumarin-modified mesoporous silica", *Nature*, 421, (2003), 350-353.

Marler, B., et al., "Influence of the sorbate type on the XRD peak intensities of loaded MCM-41", *Microporous Materials*, 6, (1996), 375-383.

Moller, K., et al., "Synthesis of Ordered Mesoporous Methacrylate Hybrid Systems: Hosts for Molecular Polymer Composites", *Chemistry of Materials*, 11(3), (1999), 665-673.

Moller, K., et al., "Inclusion Chemistry in Periodic Mesoporous Hosts", *Chemistry of Materials*, 10(10), (1998), 2950-2963.

Muñoz, B., et al., "MCM-41 Organic Modification as Drug Delivery Rate Regulator", *Chemistry of Materials*, 15(2), (2003), 500-503.

Neary, J. T., et al., "ATP-evoked calcium signal stimulates protein phosphorylation/dephosphorylation in astrocytes", *Brain Research*, 566, (1991), 89-94.

Newman, E. A., et al., "Calcium Waves in Retinal Glial Cells", *Science*, 275, (1997), 844-847.

Niemeyer, C., "Nanoparticles, proteines, and nucleic acids : biotechnology meets materials science", *Angew Chem. Int. Ed*, (2001), 4129-4158.

Ozin, G. A., "Panoscopic mateirals: synthesis over 'all' length scales", *Chem. Comm.*, (2000), 419-432.

Price, P. M., et al., "Modified silicas for clean technology", *J. Chem. Soc., Dalton Trans.*, (2000), 101-110.

Quintana, A., et al., "Design and Function of a Denrimer-Based Therapeutic Nanodevice Targeted to Tumor Cells Through the Folate Recepotr", *Pharmaceutical Research*, 19(9), (2002), 1310-1316.

Radin, S., et al., "Silica sol-gel for the controlled release of antiboitics. I. Synthesis, characterization, and in vitro release", *J. Biomed. Mater. Res.*, 57, (2001), 313-320.

Radu, D. R., et al., "Fine-Tuning the Degree of Organic Functionalization of Mesoporous Silica Nanosphere Materials via an Interfacially Designed Co-Condensation Method", *Chem. Commun.*, (2005), 1264-1266.

Radu, D. R, et al., "A polyamidoamine dendrimer-capped mesoporous silica nanosphere-based gene transfection reagent", *J Am Chem Soc*, 126(41), (Oct. 20, 2004), 14 pgs.

Ramila, A., et al., "Mesoporous MCM-41 as Drug Host System", *Journal of Sol-Gel Science and Technology*, 26, (2003), 1199-1202.

Ryoo, R., et al., "Disordered Molecular Sieve with Branched Mesoporous Channel Network", *The Journal of Physical Chemistry*, 100(451, (1996), 17718-17721.

Sadasivan, S., et al., "Synthesis and shape modification of organo-functionalised silica nanoparticles with ordered mesostructured interiors", *Journal of Materials Chemistry*, 13, (2003), 1023-1029.

Sanford, J. C., et al., "Optimizing the Biolistic Process for Different Biological Applications", *Methods in Enzymology*, 217, (1993), 483-509.

Sayari, A., "Catalysis by Crystalline Mesoporous Molecular Sieves", *Chemistry of Materials*, 8(8), (1996), 1840-1852.

Sayari, A., et al., "Periodic Mesoporous Silica-Based Organic-Inorganic Nanocomposite Materials", *Chemistry of Materials*, 13(10), (2001), 3151-3168.

Schumacher, K., et al., "The Synthesis of Spherical Mesoporous Molecular Sieves MCM-48 with Heteroatoms Incorporated into the Silica Framework", *Adv. Mater.*, 11(14), (1999), 1194-1198.

Sheen, et al., "An in vitro evaluation of the availabilitiy of cetylpyridinium chloride and chlorhexidine in some commercially available mouthrinse products", *British Dental Journal*, 194(4), (2003), 207-210.

Shukla, R., et al., "Biocompatibility of Gold Nanoparticles and Their Endocytotic Fate Inside the Cellular Compartment: A Microscopic Overview", *Langmuir*, 21, (2005), 10644-10654.

Shyu, S.-G., et al., "Immobilization of Rh(PPh$_3$)$_3$CI on phosphinated MCM-41 for catalytic hydrogenation of olefins", *Chem. Commun.*, (1999), 2337-2338.

Sing, K., et al., "Reporting Physisorption Data for Gas Solid Systems With Special Reference to the Determination of Surface-Area and Porosity", *Pure Appl. Chem.*, 57, (9185), 603-619.

Slowing, I., et al., "Effect of Surface Functionalization of MCM-41-Type Mesoporous Silica Nanoparticles on the Endocytosis by Human Cancer Cells", *Journal of American Chemical Society*, 128(46), (2006), 14792-14793.

Slowing, I. I, et al., "Mesoporous Silica Nanoparticles for Intracellular Delivery of Membrane-Impermeable Proteins", *Journal of American Chemical Society*, 129(28), (2007), 8845-8849.

Slowing, I. I., et al., "Supporting Information Mesoporous Silica Nanoparticles for Intracellular Delivery of Membrane Impermeable Proteins", *Journal of American Chemical Society*, (2007), 1-9.

Soler-Illia, G. J., et al., "Chemical Strategies to Design Textured Materials: from Microporous and Mesoporous Oxides to Nanonetworks and Heirarchical Structures", *Chem. Rev.*, 102, (2002), 4093-4138.

(56) References Cited

OTHER PUBLICATIONS

Stein, A., "Advances in Microporous and Mesoporous Solids—Highlights of Recent Progress", *Advanced Materials*, 15(10), (2003), 763-775.

Stein, A., et al., "Hybrid Inorganic-Organic Mesoporous Silicates-Nanoscopic Reactors Coming of Age", *Advanced Materials*, 12 (19), (2000), 1403-1419.

Stöber, W., et al., "Controlled Growth of Monodisperse Silica Spheres in the Micron Size Range", *Journal of Colloid and Interface Science*, 26, (1968), 62-69.

Su, F., et al., "Ordered mesoporous carbon particles covered with carbon naotubes", *Carbon*, 44, (2006), 801-803.

Subramanian, S., et al., "Quantitative analysis of transient gene expression in mammalian cells using the green fluorescent protein", *Journal of Biotechnology*, 49, (1996), 137-151.

Suzuki, K., et al., "Synthesis of Silica Nanoparticles Having a Well-Ordered Mesostructure Using a Double Surfactant Systems", *Journal of American Chemical Society*, 126, (2004), 462-463.

Takahashi, H., et al., "Immobilized enzymes in ordered mesoporous silica materials and improvement of their stability and catalytic activity in an organic solvent", *Microporous and Mesoporous Materials*, 44-45, (2001), 755-762.

Torney, F., et al., "Mesoporous silica nanoparticles deliver DNA and chemicals into plants", *Nature Nanotechnology 2*, (2007), (Published online: Apr. 29, 2007), 295-300.

Torney, F., et al., "Mesoporous silica nanoparticles deliver DNA and chemicals into plants (supplementary methods)", (2007), 7 pgs.

Uhrich, K. E., et al., "Polymeric Systems for Controlled Drug ReleaSE", *Chemical Reviews*, 99(11), (1999), 3181-3198.

Vallet, R., et al., "A new property of MCM-41 : drug delivery system", *Chem. Mater*, OARN, (2000), 308-311.

Wang, S., et al., "Incorporation of CdS Nanoparticles Inside Ordered Mesoporous Silica SBA-1 via Ion Exchange", *Advanced Materials*, 14(18), (2002), 1311-1313.

Wang, Z., et al., "Direct Observation of Calcium-Independent Intercellular ATP Signaling in Astrocytes", *Analytical Chemistry*, 72(9), (2000), 2001-2007.

Winkler, H., et al., "Quantum-Confined Gallium Nitride in MCM-41", *Advanced Materials*, 11(17), (1999), 1444-1448.

Wirnsberger, G., et al., "pH Sensing with mesoporous thin films", *Chem. Comm.*, Issue 1, (2001), 119-120.

Yanagisawa, T., et al., "The Preparation of Alkyltrimethylammonium-Kanemite Complexes and Their Conversion to Microporous Materials", *Bull. Chem. Soc. Jpn.*, 63(4), (1990), 988-992.

Yang, Q., et al., "Sulfuric Acid-Functionalized Mesoporous Benzene-Silican with a Molecular-Scale Periodicity in the Walls", *Journal of the American Chemical Society*, 124, (2002), 9694-9695.

Ying, J. Y., et al., "Synthesis and Applications of Supramolecular-Templated Mesoporous Materials", *Angewandte Chemie International Edition*, 38, (1999), 56-77.

Yiu, H. H. P., et al., "Enzyme immobilisation using siliceous mesoporous molecular sieves", *Microporous and Mesoporous Materials*, 44-45, (2001), 763-768.

Yoshitake, H., et al., "Adsorption Behavior of Arsenate at Transition Metal Cations Captured by Amino-Functionalized Mesoporous Silicas", *Chemistry of Materials*, 15(8), (2003), 1713-1721.

Yoshitake, H., et al., "Oxyanion Adsorptions by Mono-, Di-, and Triamino-Functionalized MCM-48", *Bull. Chem. Soc. Jpn.*, 76, (2003), 847-852.

Zhang, W.-H., et al., "Preparation and Characterization of ZnO Clusters inside Mesoporous Silica", *Chemistry of Materials*, 12(5), (2000), 1408-1413.

Zhang, W.-H., et al., "Synthesis and Characterization of Nanosized ZnS Confined in Ordered Mesoporous Silica", *Chemistry of Materials*, 13(2), (2001), 648-654.

Zhao, D., et al., "Morphological Control of Highly Ordered Mesoporous Silica SBA-15", *Chemistry of Materials*, 12(2), (2000), 275-279.

Zhu, Y., et al., "Developmental expression of metabotropic $P2Y_1$ and $P2Y_2$ receptors in freshly isolated astrocytes from rat hippocampus", *Journal of Neurochemistry*, 77, (2001), 530-541.

Zub, Y. L., et al., "Polyfunctionalised surfactant-templated adsorbents with high specific surface areas", *Mendeleev Commun.*, 11(6), (2001), 208-210.

Zuo, J., et al., "An estrogen receptor-based transactivator XVE mediates highly inducible gene expression in transgenic plants", *The Plant Journal*, 24(2), (2000), 265-273.

"U.S. Appl. No. 12/411,869, Final Office Action mailed Feb. 28, 2012", 17 pgs.

"U.S. Appl. No. 12/411,869, Response filed Nov. 9, 2011 to Non Final Office Action mailed Aug. 29, 2011", 10 pgs.

"U.S. Appl. No. 12/411,869, Examiner Interview Summary mailed Apr. 18, 2012", 3 pgs.

"U.S. Appl. No. 12/4.11,869, Non Final Office Action mailed Aug. 29, 2011", 15 pgs.

"U.S. Appl. No. 12/411,869, Notice of Allowance mailed Apr. 26, 2012", 7 pgs.

"U.S. Appl. No. 12/411,869, Response filed Apr. 10, 2012 to Final Office Action mailed Feb. 28, 2012", 13 pgs.

Azamian, B. R., et al,, "Directly observed covalent coupling of quantum dots to single-wall carbon nanotubes", *ChemComm*, (2002), 366-367.

Esumi, K., et al., "Adsorption of poly(ethyleneglycol) and poly(amidoamine)dendrimer from their mixtures on alumina/water and silica/water interfaces", *Colloids and Surfaces 194*, (2001), 7-12.

Nooney, R. I., et al., "Synthesis of Nanoscale Mesoporous Silica Spheres with Controlled Particle Size", *Chem. Mater.* 14, (2002), 4721-4728.

Ottaviani, M. F., et al. "EPR Investigation of the Adsorption of Dendrimers on Porous Surfaces", *J. Phys. Chem B 107.*, (2003), 2046-2053.

* cited by examiner

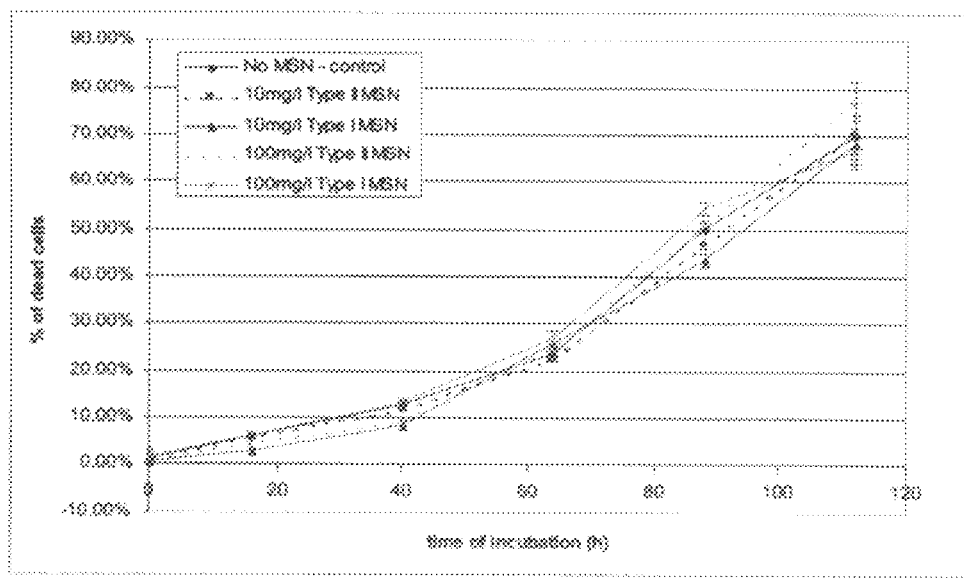
FIG. 22
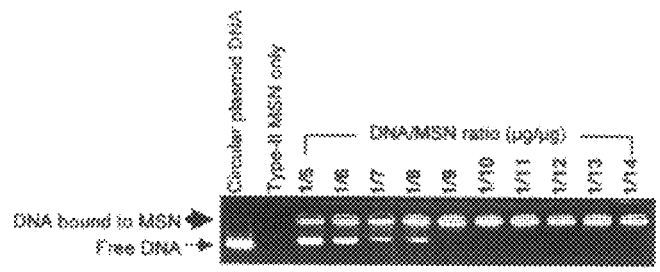
FIG. 23
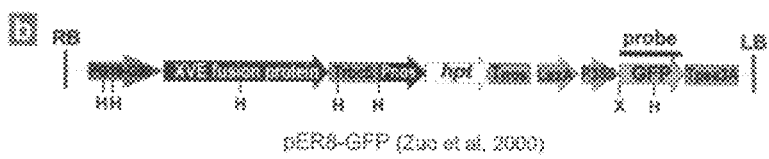
FIG. 24

METHODS OF USING CAPPED MESOPOROUS SILICATES

CROSS-REFERENCE TO RELATED APPLICATIONS

This patent application claims priority to U.S. Provisional Patent Application Ser. No. 60/793,339, filed on Apr. 19, 2006, the content of which is incorporated herein by reference in its entirety.

STATEMENT OF GOVERNMENT RIGHTS

The invention was made with a grant from the Government of the United States of America (grants CHE0239570, DBI0077692 and DBI0110023 from the National Science Foundation). The Government has certain rights in the invention.

BACKGROUND

The development of surfactant-templated mesostructures represents a major advance in materials chemistry. Several attractive features, such as large surface areas, tunable pore sizes and volumes, and well-defined surface properties make mesostructured materials ideal for hosting molecules of various sizes, shapes, and functionalities. For example see Stein et al., *Adv. Mater.* 2000, 12:1403; and Sayari et al., *Chem. Mater.* 2001, 13:3151. Hexagonally ordered mesoporous silicate structures were discovered by Mobil Corp. (M41S materials like MCM-41) and by Kuroda et al. (FSM-16 materials). See, e.g., Kresge et al., *Nature* 1992, 359:710 and Yanagisawa et al., *Bull. Chem. Soc. Jpn.* 1990, 63:988 (1990). Structures of uniform pore sizes can now be formed throughout the mesopore size range, which encompasses 2-50 nm by IUPAC definition. See, Sing et al., *Pure Appl. Chem.* 1985, 57:603.

In the field of drug delivery, many site-selective deliveries, e.g., deliveries of highly toxic antitumor drugs, such as Taxol, require "zero release" before reaching the targeted cells or tissues. Unfortunately, the release of compounds from many drug delivery systems takes place immediately upon dispersion of the drug/carrier composites in water. For example, see Radin et al., *J. Biomed. Mater. Res.* 2001, 57:313; Aughenbaugh et al., *J. Biomed. Mater. Res.* 2001, 57:321; and Kortesuo et al., *Int. J. Pharm.* 2000, 200:223. The release mechanism of other systems, such as biodegradable polymer-based drug delivery systems, also relies on the hydrolysis-induced erosion of the carrier structure. See Uhrich et al., *Chem. Rev.* 1999, 99:3181; and Langer, *Acc. Chem. Res.* 1993, 26:537. Additionally, many polymeric based release systems require organic solvents for drug loading, which can trigger undesirable modifications of the structure or function of the encapsulated molecules, such as protein denaturation or aggregation. See Li and Kissel, *Controlled Release* 1993, 27:247.

The development of mesoporous silica-based carrier systems for controlled-release delivery of drugs, biocides, genes, or even proteins in vitro or in vivo is of keen interest. See Vallet-Regi et al., *Chem. Mater.* 2001, 13:308; Munoz et al., *Chem. Mater.* 2003, 15:500; Ramila et al., *J. Sol.-Gel Sci. Technol.* 2003, 26:1199; Diaz et al., *J. Mol. Catal. B: Enzym.* 1996, 2:115; Han et al., *J. Am. Chem. Soc.* 1999, 121:9897; Kisler et al., *Microporous Mesoporous Mater.* 2001, 44-45:769; Yiu et al., *Microporous Mesoporous Mater.* 2001, 44-45:763; and Takahashi et al., *Microporous Mesoporous Mater.* 2001, 44-45:755. Additionally, recent reports in the literature have demonstrated that polyamidoamine (PAMAM) dendrimers can serve as non-viral gene transfection reagents (Dennig and Duncan, *Rev. Mol. Biotechnol.* 2002, 90:339, and the references therein; Esfand and Tomalia, *Drug Discovery Today* 2001, 6:427). However, only those PAMAMs of high generations (G>5) have been shown to be efficient in gene transfection. The required procedures for the synthesis and purification of these high G PAMAMs are usually tedious and low-yielding. In contrast, the low G PAMAMs (G<3) are typically nontoxic and easily synthesized. Despite these benefits, the smaller molecular sizes and the limited surface charges of the low G PAMAMs prohibit efficient complexation with plasmid DNAs in solution due to the entropy penalty. Despite this current interest, there remains a need for novel carrier systems that can be used for controlled-release delivery.

SUMMARY OF THE INVENTION

A mesoporous silica-based delivery system is provided for use in introducing one or more agents to plant cells or other chlorophyll containing cells, e.g., algal cells, or fungal cells. In one embodiment, the mesoporous silica-based delivery system is employed to introduce one or more agents to *Chlamydomonas* spp. such as *Chlamydomonas reinhardii*. The one or more agents may be applied (absorbed), adhered, or affixed, e.g., covalently linked, to, the surface of a mesoporous silicate body which has a polymer or ligand receptor coating, contained within pores of the mesoporous silicate body, or a combination thereof. In one embodiment, the coating is a polymer which enhances endocytosis. In one embodiment, the mesoporous silicate body is coated with, e.g., by absorption, or covalently linkage to, a polymer such as poly (amidoamine), polyethylene glycol (PEG) or triethylene lycol (TEG). In one embodiment, the coating is selected as one that binds, e.g., noncovalently via electrostatic interactions, nucleic acid or polypeptides or other ligands. In one embodiment, dendrimers or other polymers complex or otherwise bind bioactive agents, such as nucleic acids, including plasmid DNA, to form stable bioactive agent-MSN complexes. In one embodiment, the coating inhibits random aggregation of mesoporous silicate bodies. In one embodiment, the agent includes isolated DNA, RNA, polypeptide or peptide, which is applied or affixed to a polymer coating on the surface of a mesoporous silicate body.

In one embodiment, the release of the one or more agents can occur from pores within the mesoporous matrix. The pores of the mesoporous silica matrix thus act as reservoirs that can be loaded with a variety of molecules, e.g., bioactive agents such as oligonucleotides, small RNAs, peptides including hormones, e.g., plant growth hormones, enzymes, and the like. Encapsulated agents for use in the methods include but are not limited to antibacterial agents, antifungal agents, antiviral agents, nutrients, hormones, peptides, isolated nucleic acids such as isolated RNA or isolated DNA, or any combination thereof. In one embodiment, the antibacterial agents are those disclosed in U.S. published application number 20060018966. The openings of the loaded mesopores are then reversibly capped (e.g., with inorganic nanoparticles, or organic molecules such as polymers including biodegradable oligomers or dendritic polymers (dendrimers), or proteins).

The loaded and capped and/or surface complexed delivery systems allow for the controlled release of the agent(s) from the pores and/or surface of the mesoporous matrix, which can be formed as nanoparticles. In one embodiment, the capped mesoporous silica particles of the invention can be used as controlled-release carriers for the delivery of one or more agents enclosed in the pores to plant cells Given that one loading and release mechanism is based on the capping and uncapping of the openings of the mesopores, no chemical modification of the loaded molecules is needed to bind them to the pores, and no specific reaction is required to release them, apart from application of conditions required to remove the caps. In one embodiment, the capped mesoporous silica particles of the invention can be used as controlled-release carriers for the delivery of one or more agents complexed with the pore caps or surface coating. The mesoporous silicate bodies having the agents may be introduced to cells, such as plant cells via any means, e.g., bombardment, endocytosis, electroporation, and the like.

Accordingly the invention provides an article including a mesoporous silicate body that may be variously shaped and sized, having a multiplicity of pores; one or more caps obstructing one or more of the pores; and one or more agents contained within one or more of the capped pores or complexed with the surface of the body. In one embodiment, one or more bioactive agents are complexed with the outer surface of the article, complexed with molecules that occlude or otherwise cap the pores. The invention also provides novel processes and intermediates disclosed herein that are useful for preparing mesoporous silicates and articles of the invention.

The invention thus provides a mesoporous silicate body, such as a particulate solid, having one or more pores and one or more removable caps obstructing one or more of the pores. The silicate body can be a microparticle or a nanoparticle. The pores of the silicate bodies can be about 1 to about 50 nm in diameter, e.g., less than about 30 to about 50 nm in diameter, and can be about 1 nm to about 3 nm in diameter. The mesoporous silicate body can be a spherule having a diameter of about 40 to about 100 nm, about 100 to about 300 nm, about 300 to about 600 nm, or about 500 nm to about 4 µm. The mesoporous silicate body can also be a rod having a length of about 500 nm to about 1 µm, about 400 nm to about 600 nm, or about 50 nm to about 250 nm. The rods can have various diameters, typically from about 50 nm to about 500 nm.

The mesoporous silicate bodies can have removable caps, which can include inorganic and/or organic molecules. In one embodiment, the removable cap is a particle of iron oxide or gold, e.g., an iron oxide or gold nanoparticle. The nanoparticle may be covalently bonded to the mesoporous silicate, optionally through a linking group. The linking group can be any suitable cleavable moiety, for example, a linking group such as 2-(propyldisulfanyl)ethylamine, a urea containing group, or a linking group with groups susceptible to oxidation, e.g., by a reducing agent such as DTT, glutathione, cysteine, or dihydrolipoic acid, a linking group such as X—CH$_2$CH$_2$CH$_2$SSCH$_2$CH$_2$NH—C(=O)CH$_2$—Y, wherein X is a silicon atom of the mesoporous silicate and Y is a cap for the pore, such as nanoparticle. The cap of the mesoporous silicate may include an organic polymer. For example, the cap may include a poly(amidoamine), a polypeptide, or an oligonucleotide. The cap may also be a hyper-branched polymer. One example of a hyper-branched polymer is a dendrimer. Dendrimer caps can be anionic, neutral or cationic dendrimers. The caps may also be a biodegradable polymer, such as a poly(amidoamine).

In one embodiment, the mesoporous silicate bodies can deliver a nucleic acid to a plant cell by contacting the plant cell with a silicate body under conditions such that the silicate body is taken up by the cell. The nucleic acid may be DNA that is endogenous or heterologous to the plant cell into which it is delivered. The DNA molecule may be on a plasmid. The DNA may include at least one region that encodes a protein or other gene product. The mesoporous silicate bodies can deliver an effective amount of the nucleic acid as well as at least one other agent, where at least one agent is delivered to a plant cell by removing at least some of the caps from the pores so as to release an effective amount of the encapsulated agent. The caps may be removed from the pores by cleaving the linking groups. For example, a linking group that has a disulfide bond can be cleaved with a reducing agent.

Plant cells within the scope of the invention include but are not limited to dicots or monocots, e.g., monocots and other cereal crops including, but not limited to, asparagus, barley, maize (*Zea mays*), oats, orchardgrass, rice, millet, rye, sorghum (*Sorghum bicolor*), sugar cane (*Saccharum* spp), tall fescue (*Festuca arundinacea*), turfgrass (*Agrostis palustris*), and wheat (*Triticum aestivum*), while dicots include but are not limited to legumes, e.g., soybean, sunflower, *Brassica*, safflower, cotton, sugar beet, potato, *Arabidopsis*, tobacco, hemp and buckwheat.

In one embodiment, the invention provides a system for the delivery of molecules to the organelles of plant cells. The system employs mesoporous silicate nanoparticles having an average size of about 250 nm to achieve targeted delivery of DNA into plant organelles. In one embodiment, the mesoporous silicate nanoparticle may be coated with DNA as well as various chemicals allowing cell penetration. The porous nature of the material also allows mesoporous silicate nanoparticle to be filled with small molecules (e.g., dyes, chemical inducers, or siRNA). The pores can then be capped by larger molecules (such as polymers, proteins, nanoparticles, and quantum dots) that are chemically or magnetically-controlled to release the molecules encapsulated in the pores.

In particular, the following in planta delivery methods may be employed: endocytosis of the nanoparticles by plant cells, physical penetration of the nanoparticles within the cell using magnetic force, and particle bombardment, e.g., of intact cells in a plant. As described herein, when nucleic acids associated with the particles encode a reporter, reporter expression was observed in transformed plant tissue transiently and stably. Thus, the particles may be employed to target nucleic acids, peptides and/or small molecules to plastids and/or mitochondria to achieve targeted drug and/or nucleic acid delivery, and/or non-nuclear genome transformation. The targeting may be achieved by targeting polypeptides or proteins linked to the nanoparticles or to its capping material, providing localization to the desired subcellular location using the cellular addressing machinery, or by antibody-antigen affinity.

Organelle transformation has several advantages compared to nuclear transformation. The advantages for chloroplast transformation include high level production for prokaryotic origin proteins and the possibility of avoiding dissemination of the transgene through pollen.

In one embodiment, the receptor-ligand interaction of an organelle transit peptide, such as a chloroplast transit peptide (CTP), may be employed to deliver DNA-coated MSN to organelles. For instance, synthetic ligand or transit peptide is linked to MSN and these MSN are coated with DNA molecules and/or small cargo substances encapsulated in the pores. The loaded MSN are then introduced to plant cells, and the MSN with ligand or transient peptide targets specific organelles and delivers the transgene together with the nanoparticles. Because the process is via ligand-receptor interaction and not a mechanical delivery, the DNA can then be introduced into all plastids. Optionally, a chemical (with ability to temporarily alter the membrane permeability) is included in the MSN pores to enhance the penetration of the foreign DNA into the plastid. Integrating a transgene into the plastid genome may alleviate concerns regarding transgene dissemination in the environment, as well as allowing the achievement of high yield production of the transgene product.

The invention thus provides a method for plant genetic transformation (for nuclear and non-nuclear genomes) and/or intracellular drug delivery using nanoparticles. The methods include the use of hollow nanoparticles which can be filled and/or coated with various chemicals including nucleic acids and/or drugs. The cavities in the nanoparticles may be closed using various materials linked to the nanoparticles, thus preventing the exit of the chemical from the nanoparticles cavities.

The present invention thus provides for delivery of both DNA and chemicals (or other small molecules) simultaneously, and targeting of both nuclear and non-nuclear (organelle) genomes.

BRIEF DESCRIPTION OF THE FIGURES

FIG. 14 illustrates scanning electron microscopy of IOMSN bombarded embryos. A) and B) Agglomerates of MSN are clearly visible on the tissue surface (indicated by blue arrows). C) to F), holes in the cells. C) is a magnification of the box in F) showing a hole in the cell with IOMSN in. Isolated MSN are identifiable on the cell surface in A) through F) (some are indicated by white arrows). The holes are indicated by black arrows. The bar represents 2 μm in each picture. The IOMSN have a 0.2 μm diameter in average (Giri, S. personal communication).

FIG. 19 depicts MSN for plant cell internalization. (A) Schematic representation of a series of surface-functionalized mesoporous silica nanoparticles (MSNs) for intracellular controlled release of genes and chemicals in plant cells. Type-I: fluorescein-labeled MSN; Type-II: fluorescein-labeled, triethylene glycol (TEG)-coated MSN; Type-III: fluorescein-filled MSN capped by gold nanoparticles; Type-IV: β-estradiol loaded MSN capped by gold nanoparticles. Transmission electron micrographs of Type II (B) and Type III (C) MSNs (bar: 100 nm). Arrow heads in (C) indicate gold nanoparticles.

FIG. 22 shows evaluation of Type I and Type II MSN toxicity on *Arabidopsis* mesophyll protoplasts. Isolated protoplasts ($2 \times 10^5$ per well in 6 well plates) were incubated in 2 mL W5 medium, 23° C., dark, shaking 60 rpm, with either Type I or Type II MSN at two different concentrations (10 and 100 mg/L). This represents 100 and 1000 times, respectively, higher concentrations than in FIG. 20. As a control, the same amount of protoplast was incubated in W5 without MSN of any type. Each day 0.2 mL of fresh W5 media was added to compensate liquid loss due to evaporation. Cell viability was assessed using phenosafranin as described by Widholm (1972). Each condition was evaluated in independent triplicates and each sample was counted three times at each time point.

FIG. 23 illustrates agarose electrophoresis of DNA binding on Type-II MSN. Type-II MSN materials were incubated in water with a purified circular plasmid DNA (11 Kb) at various ratios for 2 hours at 23° C. The entire incubation mix was then electrophorized in 1% agarose gel containing 100 μg/L ethidium bromide to allow DNA detection. The free DNA (thin arrow) migrates in the gel whereas the bound DNA (thick arrow) remains in the wells.

FIG. 24 shows a diagram of key relevant components in plasmids used in the experiments. (a) pFT01, a plasmid used in DNA/MSN binding and plant cell endocytosis experiments. 2×P35S, double CaMV (cauliflower mosaic virus) 35S promoter; EGFP, enhanced Green Fluorescence Protein; Tnos, 3' terminator from nopaline synthase gene; TEV, tobacco etch virus translational enhancer; bar, phosphinothricin acetyl transferase gene that confers resistant to herbicide phosphinothricin and its derivatives; Tvsp, 3' terminator from soybean vegetative storage protein gene. (b) pER8-GFP (Zuo et al, 2000, *Plant J.*, 24:265 kindly provided by N—H, Chua), a plasmid used for DNA/MSN binding and digestion experiment, generating transgenic tobacco plants expressing inducible GFP and experiments of co-delivery of DNA and chemicals to the plants. PG10-G90, a chimeric constitutive promoter containing a basal −90 CaMV35S fragment fused to a plant −10 G box tetramer fragment (Ishige et al., *The Plant Journal*, 1999, 18:443); XVE fusion protein, estrogen receptor-based transactivator (Zuo et al., supra); TrbcS, 3' poly(A) addition sequence from tobacco ribulose bisphosphate carboxylase small subunit; Pnos, promoter from nopaline synthase gene; hpt, hygromycin resistant gene; Tnos, 3' terminator from nopaline synthase gene; LexA, bacterial repressor (residues 1-37); P35S, CaMV 35s promoter; GFP, Green Fluorescence Protein; Tpea3A1 3' terminator from pea ribulose 1,6-bisphosphate carboxylase small subunit. Probe, probing segment used for Southern blot analysis. H, Hind III restriction enzyme sites. X, Xho I restriction enzyme site. Probe: $^{32}$P-labeled DNA probe for Southern blot analysis of transgenic plants. RB, right border sequence of *A. tumefaciens* T-DNA; LB, left border sequence of *A. tumefaciens* T-DNA. The diagram does not represent each fragment to scale.

DETAILED DESCRIPTION

Figure 1:
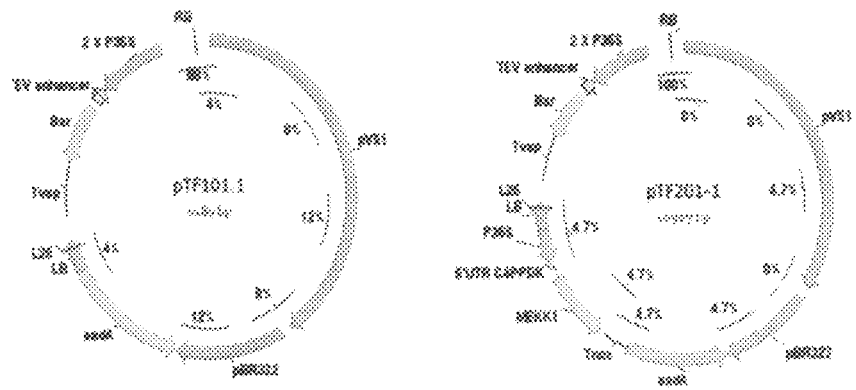
FIG. 1 illustrates vectors for plant transformation.

The term "amino acid," comprises the residues of the natural amino acids (e.g., Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g., phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g., acetyl or benzyloxycarbonyl), as well as natural and unnatural amino acids protected at the carboxy terminus (e.g., as a ($C_1$-$C_6$)alkyl, phenyl or benzyl ester or amide). Other suitable amino and carboxy protecting groups are known to those skilled in the art (See for example, T. W. Greene, *Protecting Groups In Organic Synthesis*; Wiley: New York, 1981, and references cited therein).

The term "polypeptide" describes a sequence of at least 50 amino acids (e.g., as defined hereinabove) or peptidyl residues while a peptide describes a sequence of at least 2 and up to 50 amino acid residues. The sequence may be linear or cyclic. For example, a cyclic peptide can be prepared or may result from the formation of disulfide bridges between two cysteine residues in a sequence. A polypeptide can be linked to other molecules through the carboxy terminus, the amino terminus, or through any other convenient point of attachment, such as, for example, through the sulfur of a cysteine. In one embodiment of the invention a polypeptide comprises about 50 to about 300 amino acids. In another embodiment a peptide has about 5 to about 25 amino acids Peptide and polypeptide derivatives can be prepared as disclosed in U.S. Pat. Nos. 4,612,302; 4,853,371; and 4,684,620, or as described in the Examples hereinbelow. Polypeptide sequences specifically recited herein are written with the amino terminus on the left and the carboxy terminus on the right.

The term "nucleic acid", "polynucleic acid" or "polynucleic acid segment" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 1991, 19:5081; Ohtsuka et al., *J. Biol. Chem.* 1985, 260:2605; Rossolini et al., *Mol. Cell. Probes* 1994, 8:91). An "oligonucleotide" typically includes 30 or fewer nucleotides.

As used herein, the terms "isolated and/or purified" refer to in vitro preparation, isolation and/or purification of a nucleic acid or protein (polypeptide or peptide) so that it is not associated with in vivo substances, or is substantially purified from in vitro substances. Thus, with respect to an "isolated nucleic acid molecule", which includes a polynucleotide of genomic, cDNA, or synthetic origin or some combination thereof, or an "isolated polypeptide or peptide", the "isolated nucleic acid molecule" or "isolated polypeptide or peptide" (1) is not associated with all or a portion of cell based molecules with which the "isolated nucleic acid molecule" or "isolated polypeptide or peptide" is found in nature, (2) is operably linked to a molecule which it is not linked to in nature, or (3) does not occur in nature as part of a larger sequence. An isolated nucleic acid molecule means a polymeric form of nucleotides of at least 10 bases in length, either ribonucleotides or deoxynucleotides or a modified form of either type of nucleotide. The term includes single and double stranded forms of DNA. The term "oligonucleotide" referred to herein includes naturally occurring, and modified nucleotides linked together by naturally occurring, and non-naturally occurring oligonucleotide linkages. Oligonucleotides are a polynucleotide subset with 200 bases or fewer in length. Preferably, oligonucleotides are 10 to 60 bases in length and most preferably 12, 13, 14, 15, 16, 17, 18, 19, or 20 to 40 bases in length. Oligonucleotides may be usually single or double stranded. Oligonucleotides can be either sense or antisense oligonucleotides. The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phosphoraniladate, phosphoramidate, and the like.

The term "complexed" refers to binding of a molecule to a mesoporous silicate body or pore cap, typically through means other than covalent bonding. Such binding can take to form of, e.g., ionic or electrostatic interactions, or other attractive forces.

Mesoporous Silicates

Mesoporous silicates typically may have a particle size of about 50 nm to about 1 µm. In one embodiment, the mesoporous silicates may have a particle size of at least about 100 nm. In another embodiment, the mesoporous silicates may have a particle size of less than about 750 nm. In one embodiment, the mesoporous silicates may have a particle size of about 250 nm. In other embodiments, the mesoporous silicate body may be a sphere having a diameter of about 50 to about 150 nm, about 60 to about 300 nm, or about 250 to about 1000 nm. The mesoporous silicates may be spherical or may have other shapes, such as rods. In certain embodiments, the mesoporous silicate body can be a rod having a length of about 50 to about 150 nm, about 60 to about 300 nm, or about 250 to about 1000 nm. The articles of the invention can include mesoporous silicates of any shape and size, provided the pore structure is suitable for receiving the encapsulated agent.

The mesoporous silicate pores typically have a diameter of from about 1 to about 100 nm. In one embodiment of the invention, the pores have a diameter of at least about 2 nm. In another embodiment, the pores have a diameter of about 1 nm to about 5 nm, or about 1 nm to about 3 nm. In other embodiments, the pores have diameters of greater than about 5 nm, or greater than about 10 nm. Typically, the pores have a diameter of less than about 75 nm or less than about 50 nm.

Mesoporous silicate particles may be prepared by various methods such as by co-condensing one or more tetraalkoxy-silanes and one or more organo-substituted trialkoxy-silanes to provide a population of mesoporous silicate particles having monodisperse particle sizes and preselected particle shapes, wherein the substituted trialkoxy-silane is not a co-solvent. The mesoporous silicate particles can be prepared by co-condensing one or more tetraalkoxy-silanes and one or more (3-cyanopropyl)trialkoxy-silanes to provide the mesoporous silicate particles as nanorods. Any suitable and effective tetraalkoxy-silane and alkyl-trialkoxy-silane can be employed. Many such silanes are described in, e.g., *Aldrich Handbook of Fine Chemicals*, 2003-2004 (Milwaukee, Wis.).

The mesoporous silicates may be prepared from surfactant micelles of $C_{10}$-$C_{16}$ alkyl(trialkyl)ammonium salts in water, followed by introduction into the solution of an alkyl orthosilicate, such as tetraethylorthosilicate (TEOS), and one or more functionalized silanes, such as one or more mercaptoalkyl-, chloroalkyl-, isocyanate-, aminoalkyl-, carboxyalkyl-, sulfonylalkyl-, arylalkyl-, alkynyl-, or alkenyl-silanes, wherein the $(C_2$-$C_{10})$alkyl chain is optionally interrupted by —S—S—, amido (—C(=O)NR—), —O—, ester (—C(=O)O—), and the like. For example, functionalized silanes can be, e.g., 3-mercaptopropyl-trimethoxysilane (MPTMS) or 3-isocyanatoprypyl-triethoxysilane (ICPTES). The aqueous mixture is stirred at moderate temperatures until the silicate precipitates, and it is collected and dried. The surfactant "template" is then removed from the pores of the ordered silicate matrix, for example, by refluxing the silicate in aqueous-alcoholic HCl. The remaining solvent can be removed from the pores of the silicate by placing it under high vacuum. The functional groups incorporated on the surface of the pores can be quantified and used as linker moieties to bind to the caps, or they can be further modified by attaching terminally-functionalized organic linker moieties that can be reacted with functional groups on the caps. The polarity of the interior of the pores can also be adjusted by adding other functionalized silanes to the reaction mixture, including ones comprising non-polar inert groups such as aryl, perfluoroalkyl, alkyl, arylakyl and the like. The exterior of the silicate matrix can be functionalized by grafting organic moieties comprising functional groups thereto. These groups can in turn be employed to link the particles to targeting or labeling moieties. The targeting moiety can be an antibody, a DNA or RNA aptamer, a saccharide, a protein, or a polypeptide. Other suitable and effective targeting moieties can also be employed.

Functionalized Caps

In one embodiment of the invention, the MSN includes one or more caps that serve to slow or to prevent the release of an encapsulated agent from the pores of the mesoporous silicate. Thus, as used herein, "obstructing" or "occluding" includes partially or fully blocking the opening of a pore such that the release of an encapsulated agent is slowed or prevented. The cap may be covalently bonded to the mesoporous silicate or it may be associated thereto through ionic bonding, hydrogen bonding, or other interactions. The cap may be positioned in the opening of a pore or may be located within the pore itself (e.g., bonded or linked to the interior surface of the pore). The cap may be a discrete body, such as a particle of an organic or inorganic salt, protein, or a polymer or polymeric nanosphere, or may be in the form of a polymer coating that partially or completely covers the mesoporous silicate particle. When the cap is a discrete body, such as an inorganic particle, the cap may optionally be covalently bonded to the mesoporous silicate or a pore thereof, or may be associated thereto through ionic bonding, hydrogen bonding, or other interactions.

The cap may comprise a variety of materials, which can be selected based on the intended application for the loaded particles and on the size and reactivity of the mesoporous silicate material. For example, the cap may comprise an inorganic particle or crystal, an organic polymer, such as a hyper-branched polymer, dendrimer, or a polypeptide, or a biopolymer, such a protein, an oligonucleotide, or an oligosaccharide. Inorganic particles useful as caps include, e.g., metal oxides.

As used herein, a hyper-branched polymer refers to a branched polymer wherein the structural branching is regular, irregular, or random. Typically, the hyper-branched polymer consists of a multifunctional core molecule to which branched wedge-like molecules are attached. A dendrimer is an example of a symmetrically branched hyper-branched polymer. As used herein, a dendrimer refers to a molecule consisting of a multifunctional core molecule with a dendritic wedge attached to each functional site. Each dentritic wedge has regular, highly branched monomers leading to a monodisperse, tree-like or generational structure. Synthesizing monodisperse polymers is achieved through stepwise reactions, building the dendrimer up one monomer layer, or "generation," at a time. The core molecule is referred to as "generation 0." Each successive repeat unit along all branches forms the next generation, "generation 1," "generation 2," and so on until the terminating generation. Organic polymers, such as a hyper-branched polymers, dendrimers, and polypeptides that can be used as caps are described in, e.g., WO 02/057745, WO 99/32076, WO 93/06868, U.S. Pat. Nos. 5,527,524; 5,574,142; 5,714,166; 6,020,457; 6,190,650; 6,225,352; 6,395,266; 6,426,067; and 6,464,971; and as described by Patri et al. *Polym. Mat. Sci. & Eng.* 2002, 86:130, Quintana et al. *Pharm. Res.* 2002, 19(9):1310, and Baker et al. *Biomedical Microdevices* 2001, 3:1, 61.

Inorganic crystals polymers or particles can be selected based on the size of the pores in the mesoporous silicate, the size of the metal containing particle, the reactive sites available for attaching the mesoporous silicate to the particle, and based on the chemical and physical environment where the capped particle will be delivered. One cap that may be particularly useful for facilitating the delivery of an article to the interior of a cell is a dendrimer or hyper-branched polymer, such as a biodegradable poly(amidoamine) dendrimer.

The caps can be associated (e.g., bonded, complexed, or attracted) directly with the surface of the mesoporous silicate body or the surface of the pores, or the caps can be associated with a linker group that is attached to the surface of the mesoporous silicate body or the surface of the pores. Linking groups can be selected based on their ability to bond to or be incorporated with the mesoporous silicate and on their ability to associate with a given cap. The length of the linking group is not critical, provided it allows the associated cap to obstruct the pores of the mesoporous silicate. For example, the linking group can typically be from about 5 Angstroms to about 500 Angstroms in length. For some applications, the linking group can preferably be from about 25 Angstroms.

In one embodiment of the invention, the linking group comprises labile group that can selectively react with a releasing agent to release the cap from the mesoporous silicate following delivery to a target site. The releasing agent can be an agent that is naturally present at the target site, or it can be an agent that is introduced at the target site when release of the encapsulated material is desired. For example, the labile group can be a reactive disulfide bond, a pH sensitive bond, a temperature labile bond, or a photochemically active group and the releasing agent can be a disulfide reducing agent, acid/base (local pH changes), temperature variation, or light of a preselected wavelength. Another linking group can be a biodegradable poly(amidoamine) chain.

Encapsulated and Complexed Agents

The articles of the invention are generally useful for delivering one or more agents preferably in a controlled manner to plant cells. The nature of the complexed and/or encapsulated agents is not critical The agents include genes, nutrients (vitamins, etc.), and biocidal or pesticidal agents (e.g., insecticides or herbicides). For example, the term includes but is not limited to antibacterial agents, antifungal agents, antiviral agents, polypeptides, hormones, enzymes, antibodies, and RNA or DNA molecules of any suitable length, or any combination thereof. For instance, the RNA or DNA molecules may encode herbicide resistance, drought tolerance, a polypeptide associated with enhanced nutritional value, and the like.

The encapsulated materials can be free in the mesopores of the silicate body or they can be associated (e.g., bonded or attracted) with the interior surface of the pores. When they are free in the pores, they can typically be loaded by contacting an uncapped "empty" mesoporous silicate in a solution of the agent to be encapsulated. When the encapsulated agents are associated with the interior surface of the pores, they can typically be loaded by allowing the agent to react with, or be attracted to, groups on the interior surface of the pores under conditions suitable to allow the agent to associate. In one embodiment of the invention, the mesoporous silicates can be stirred in ethanol for a period of time sufficient to load the material into the pores. Any suitable and effective solvent can be employed in this particular manner of pore loading.

In one embodiment of the invention, poly(amidoamines) can be attached to the surface of a mesoporous silica nanoparticle to facilitate endocytosis or otherwise being taken up by the cell.

Caps or dendrimers can be "associated" to the mesoporous silicates through ionic, covalent or other bonds (e.g., electrostatic interactions). For example, the caps or dendrimers can be covalently bonded to the mesoporous silicates either directly or through a linking group, such as linking groups used to bind active agents to the dendrimers.

In one embodiment, DNA molecules can be associated with particles of the invention (e.g., particles having surface associated dendrimers) through ionic, covalent or other bonds (e.g., electrostatic interactions). The polyanionic nature of plasmid DNAs or genes makes them electrostatically attractive to positively charged dendrimers, such as poly(amidoamine) (PAMAM) and poly(propylenimine) (PPI), or polyethylene glycol (PEG) or triethylene glycol (TEG), or under physiological condition (pH 7.4). Thus, introduction of DNA to coated mesoporous silicates facilitates a strong and multivalent binding between the DNA and coated silicate material.

The capped particles of the invention can be used to transform plant cells, delivering "foreign DNA" as disclosed in U.S. Pat. Nos. 6,329,574 and 5,384,253.

The invention will now be illustrated by the following non-limiting Examples.

General Reagents and Materials.

Cadmium nitrate tetrahydrate (99.99%), sodium sulfide, mercaptoacetic acid, 3-mercaptopropyltrimethoxysilane (MPTMS), N-cetyltrimethylammonium bromide (CTAB), tetraethyl orthosilicate (TEOS), 2-aminoethanethiol hydrochloride, 1-[3-(dimethylamino)propyl]-3-ethylcarbodiimide hydrochloride (EDC), dithiothreitol (DTT), and aldrithiol-2 were purchased (Aldrich) and used as received. Vancomycin hydrochloride and adenosine triphosphate disodium salt (ATP) were obtained from Sigma and used without further purification. Nanopure water (18.1 MHz) prepared from a Barnstead E-pure water purification system was employed throughout. PBS buffer (10.00 mM, pH 7.4) solutions with the total ionic strength of 0.06 M were prepared and used as the solvent for all the loading and release experiments of vancomycin and ATP.

EXAMPLES

Example 1

Drug-Loaded Mesoporous Silica Particles Capped With CdS a. Loading of Vancomycin and ATP into a Mesoporous Framework of Linker-MSN and Capping the Mesopores with Mercaptoacetic Acid-Functionalized CdS Nanoparticles Purified linker-MSN material from sub-part (b) below (100.00 mg) was incubated in a PBS buffer solution (0.60 mL, pH 7.4) of ATP or vancomycin (3.00 µmol in both cases) for 24 hours. Mercaptoacetic acid-functionalized CdS nanoparticles from sub-part (c) below (0.15 mmol) were dissolved in 2.00 mL of PBS buffer with vancomycin or ATP (0.01 mmol in both cases); 1-[3-(dimethylamino)propyl]-3-ethylcarbodiimide hydrochloride (EDC) (57.50 mg, 0.30 mmol) was added to the CdS/drug solution. The reaction mixture was allowed to stir for 24 hours, followed by centrifuging the suspension at 12,000 rpm for 3 minutes. The resulting precipitates (ATP- or vancomycin-loaded, CdS-capped MSNs) were isolated and dried under vacuum.

b. Synthesis of MCM-41-Type Mesoporous Silica Nanosphere with 2-(Propyldisulfanyl)ethylamine Functionality (Linker-MSN)

As described below in detail, a mercaptopropyl-derivatized mesoporous silica nanosphere material (thiol-MSN) was synthesized using a method similar to that described by Lin et al., *J. Am. Chem. Soc.* 2001, 123:11510; and Lin et al., *J. Am. Chem. Soc.* 2002, 124:9040. The surfactant-removed thiol-MSN material was treated with a methanol solution of 2-(pyridyldisulfanyl)ethylamine at room temperature for 24 hours under vigorous stirring to yield the MSN material with 2-(propyldisulfanyl)-ethylamine functionality (linker-MSN).

N-Cetyltrimethylammonium bromide (CTAB, 1.00 g, $2.74 \times 10^{-3}$ mol) was dissolved in 480 mL of Nanopure water. NaOH(aq) (2.00 M, 3.50 mL) was added to CTAB solution, followed by adjusting the solution temperature to 353 K. TEOS (5.00 mL, $2.57 \times 10^{-2}$ mol) was introduced dropwise to the surfactant solution, followed by the dropwise addition of MPTMS (0.97 mL, $5.13 \times 10^{-3}$ mol). The mixture was allowed to stir for 2 hours to give white precipitates (as synthesized thiol-Sphere). The solid product was filtered, washed with deionized water and methanol, and dried in air. To remove the surfactant template (CTAB), 1.50 g of as-synthesized thiol-Sphere was refluxed for 24 hours in a solution of 9.00 mL of HCl (37.4%) and 160.00 mL of methanol followed by extensive washes with deionized water and methanol. The resulting surfactant-removed thiol-MSN material was placed under high vacuum to remove the remaining solvent in the mesopores. The chemically accessible thiol group surface coverage of the thiol-MSN material was quantified to be $7.64 \times 10^{-4}$ mol/g using the method described by Lin et al., *J. Am. Chem. Soc.* 2001, 123:11510. The purified thiol-MSN material (1.00 g) was treated with a methanol solution (60.00 mL) of 2-(pyridyldisulfanyl)-ethylamine (PDEA) ($9.12 \times 10^{-4}$ mol, prepared as described by Ebright et al., *Bioconjugate Chem.* 1996, 7:380) at room temperature for 24 hours under vigorous stirring to undergo the desired disulfide bond exchange reaction. The resulting MSN material with 2-(propyldisulfanyl) ethylamine functionality was filtered and washed with methanol and dried in air.

c. Synthesis of Mercaptoacetic Acid-Derivatized Cadmium Sulfide (CdS) Nanoparticles The synthetic procedures were modified from those reported by Colvin et al., *J. Chem. Soc.* 1992, 114:5221. Mercaptoacetic acid ($2.15 \times 10^{-3}$ mol, 150.00 µL) was added to an aqueous solution (270.00 mL) of cadmium nitrate tetrahydrate ($3.00 \times 10^{-4}$ mol), forming a turbid blue solution. The pH was adjusted to 11 with 0.01 M NaOH. Sodium sulfide ($1.50 \times 10^{-4}$ mol) was dissolved in 10.0 mL of $H_2O$ and rapidly added to the cadmium nitrate solution with vigorous stirring. The reaction mixture was protected from light, stirred for 10 minutes, and concentrated to about one-tenth of its original volume with a rotary evaporator. Anhydrous methanol was added to provide the mercaptoacetic acid-capped water-soluble cadmium sulfide nanoparticles (CdS) as a precipitate.

d. Instrumental Methods, Conditions, and Parameters for the Structure Characterizations of Linker-MSN and CdS-Capped MSN Materials Powder XRD diffraction data were collected on a Scintag XRD 2000 X-ray diffractometer using Cu Kα radiation. Nitrogen adsorption and desorption isotherm, surface area (SA), and median pore diameter (MPD) were measured using a Micromeritics ASAP2000 sorptometer. Sample preparation included degassing at 130° C. for 1 hour. Nitrogen adsorption and desorption isotherms of these materials were obtained at −196° C. Specific surface areas and pore size distributions were calculated using the Brunauer-Emmett-Teller (BET) and Barrett-Joyner-Halenda (BJH) method, respectively. Particle morphology of these materials was determined by scanning electron microscopy (SEM) using a JEOL 840A scanning electron microscope with 10 kV accelerating voltage and 0.005 nA of beam current for imaging. For transmission electron microscopy (TEM) studies, a small aliquot was removed and placed between two clean glass slides. Slides were squeezed between fingers and rubbed back and forth to break up larger clumps. The resulting powder was washed into a Petri dish with acetone. The mixture was stirred and ultrasonically agitated. While still in suspension a lacey carbon-coated TEM grid was pulled through the suspension. The grid was allowed to dry in air and then examined in an Amray 1845 FE-SEM followed by examination with a Philips model CM-30 TEM operated at 300 kV. The specimen was given no further treatment, as it appeared stable under beam bombardment. The preparation for the microtomed samples included embedding into a derivation of EPON epoxy resin using EmBed 812. This mixture was centrifuged and cured for 24 hours at 60° C. The embedded block was microtomed to obtain thin sections of 60-80 nm thickness by using a Reichert Ultracut S ultramicrotome with a diamond knife (Diatome). The floated sections were mounted on a 400 mesh Pd-coated Cu grid. The TEM images of these microtomed samples were recorded using a Philips model CM-30 TEM operated at 300 kV at 69 000 to 340 000 electron optical magnification.

e. Results

The spherical particle shape and the MCM-41 type of hexagonally packed mesoporous structure of the linker-MSN material were confirmed by scanning and transmission electron microscopy (SEM and TEM, respectively). The $N_2$ adsorption/desorption isotherms of the material further revealed a BET isotherm typical of MCM-41 structure (type IV) with a surface area of 941.0 $m^2/g$ and a narrow BJH pore size distribution (average pore diameter=2.3 nm). The linker-MSN (100.0 mg) was used as a chemically inert host to soak up the aqueous solutions of vancomycin (3.0 plop and ATP (15.5 μmol).

The water-soluble CdS nanocrystals (average particle diameter of 2.0 nm) with mercaptoacetic acid groups were covalently captured and formed amide bonds by reacting with the mesopore surface-bound 2-(propyldisulfanyl)ethylamine linkers of the MSN/drug composite material in aqueous solutions. The resulting reaction suspensions were centrifuged, and the CdS-capped MSN/drug composite materials along with the unreacted CdS nanoparticles were filtered. The concentrations of the free vancomycin and ATP molecules in the filtrate were then determined by HPLC. The calculated concentration decreases of solution vancomycin and ATP were attributed to the amounts of mesopore-encapsulated vancomycin (2.5 μmol) and ATP (4.7 μmol) per 100.0 mg of linker-MSN material. These numbers correspond to ca. 83.9 and 30.3 mol % loading efficiency, respectively.

The successful incorporation of CdS nanoparticles to the MSN matrix was confirmed by various spectroscopy methods. The covalent immobilization of the surface-functionalized CdS nanoparticles to the linker-MSN material reduced the intensity of the powder X-ray diffraction (XRD) peaks. Such a reduction of scattering contrast between the pores and the framework of the MCM-41 materials due to the pore-filling effect has been reported previously in the literature by Marler et al., *Microporous Mater.* 1996, 6:375; Winkler et al., *Adv. Mater.* (*Weinheim, Ger.*) 1999, 11:1444; Zhang et al., *Chem. Mater.* 2000, 12:1408; and Zhang et al., *Chem. Mater.* 2001, 13:648. Compared with the $d_{100}$ value of the linker-MSN material, a small increase in that of CdS-capped MSN was observed. The increase of the $d_{100}$ values may be attributed to the covalent linkage induced pore-filling effect between the CdS nanoparticles and the mesoporous silica matrix.

In contrast to the low-intensity diffuse peak of noncrystalline silica observed in the linker-MSN material, the high-angle XRD diffraction patterns of the linker-MSN and the CdS-capped MSN materials within the 20 range of 10°-70° showed two additional peaks in the CdS-capped MSN sample. These two peaks were attributed to the diffraction of (111) and (220) lattice planes of the CdS nanoparticles attached to the mesoporous silica. See Kumar et al., *Langmuir* 2000, 16:9299; Diaz et al., *J. Phys. Chem. B* 1999, 103:9854; Weller et al., *Chem. Phys. Lett.* 1986, 124:557; and Yang et al., *Chem. Mater.* 2000, 12:3259. To further confirm that these CdS nanoparticle "caps" were indeed covalently linked to the mesopore surface-bound linker groups, the $^{13}C$ solid-state CP-MAS NMR spectra of both the CdS-capped MSN and the linker-MSN were carefully compared and the existence of the covalent linkage between the CdS and MSN materials was clearly observed.

TEM investigations of the CdS-capped MSN also provided direct evidence of the CdS distribution both on and in the organically functionalized MSN material. The CdS nanoparticles were clearly visible on the outside edge and inside the mesopores of the MSN depicted by the lighter areas (indicated by the arrowheads). As opposed to these features observed in the case of CdS-capped MSN, the TEM micrograph of the linker-MSN prior to the CdS "capping" showed smooth edges and nice contrasts between the mesoporous channels and the silica matrix. Furthermore, compared with the periodically well-organized hexagonal array of mesopores represented by the bright dots shown on the TEM micrograph of the linker-MSN orientated along the pore axis, an additional layer of CdS nanoparticles on the outside of the MSN material and a large area of disordered hexagonal array of mesopores were observed in the case of CdS-capped MSN material. In contrast to the "disordered" area, a small area with mesopores that are packed with a hexagonal symmetry was also noticed on the micrograph. These different areas could be attributed to the fact that most, but not all, mesopores are capped with the CdS nanoparticles.

Example 2

DTT-Induced Drug/Neurotransmitter Release Study

CdS-capped MSN with vancomycin or ATP (10.00 mg) material was dispersed in 1.50 mL of PBS buffer (pH 7.4), followed by repeating wash/sonication/centrifugation cycles for five times to remove physisorbed, uncapped vancomycin or ATP molecules on the exterior surface of the material. The purified MSN/drug composite was redispersed in 3.50 mL of PBS buffer (pH 7.4). Aliquots were taken every 4 hours over a time period of 12 hours from the MSN/water suspension and injected to an analytical HPLC system (Hitachi LC/3DQMS with a reverse phase C18 column (Vydac), 0.4 cm×25 cm) to monitor the leaching of the mesoporous channel encapsulated vancomycin or ATP molecules. After 12 hours, dithiothreitol (DTT, 18.50 mM) was added to the suspension to cleave the disulfide linkage between the CdS nanoparticle and the MSN. The kinetic profiles of the DTT-induced release of vancomycin and ATP were monitored by following two literature-reported HPLC separation conditions. The peaks/areas at 280 and 258 nm were monitored/integrated for the quantitative analysis of amounts of released vancomycin and ATP, respectively. See Farin et al., *J. Pharm. Biomed. Anal.* 1998, 18:367; and Veciana-Nogues et al., *Food Chem.* 1997, 59:467.

Results

Figure 5:
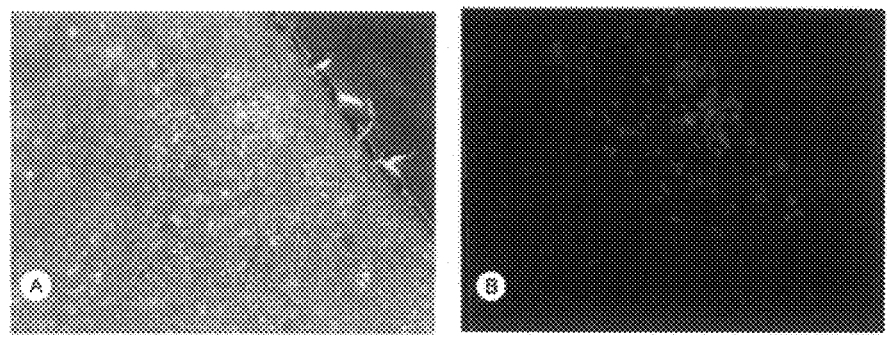
FIG. 5 illustrates pLMNC95 coated PAMAM-IOMSN (1/5 ratio) induced fluorescence. Shooting paramters=6 cm 900 psi. Discreate spots are visible under UV light that may be due to GFP expression.

The CdS-capped MSN drug/neurotransmitter delivery system exhibited less than 1.0% of drug release in 10 mM PBS buffer solutions (pH 7.4) over a period of 12 hours. The result suggested a good capping efficiency of the CdS nanoparticles for encapsulation of the vancomycin and ATP molecules against the undesired leaching problem. Addition of disulfide-reducing molecules, such as DTT and ME, to the aqueous suspension of CdS-capped MSNs triggered a rapid release of the mesopore-entrapped drug/neurotransmitter. Within 24 hours, the release reached 85% of the total release seen in 3 days of vancomycin and ATP after the introduction of 18.5 mM DTT. Interestingly, the rates of release of vancomycin and ATP showed similar diffusional kinetic profiles, indicating the lack of interaction between these released molecules and the mesoporous silica matrix. However, 53.8% (1.6 μmol) of the encapsulated vancomycin was released after 3 days of the DTT-induced uncapping of the mesopores, while only 28.2% (1.3 μmol) of the entrapped ATP molecules was able to diffuse away. Such a large difference between the portion of vancomycin and ATP released from the MSN material implied that ATP molecules were more strongly physisorbed to the organically functionalized mesoporous channels than the vancomycin molecules. On the basis of several reports in the literature (Takacs-Novak et al., *Int. J. Pharm.* 1993, 89:261) vancomycin has an isoelectric point (pI) of 8.3 and therefore is cationically charged under our experimental condition (pH 7.4). Conversely, ATP is anionic in pH 7.4 aqueous solutions. Given that the surface of the linker-MSN material is decorated with the 2-(propyldisulfanyl)ethylamine functionality, which is cationic (ammonium cation) at pH 7.4, the attractive electrostatic interaction between the ATP molecules and the linker-functionalized mesopores could be attributed to the stronger physisorption of ATP, whereas the repulsive electrostatic interaction between vancomycin molecules and the linker-derivatized mesopores disfavor the surface adsorption of vancomycin. These results suggested that perhaps only those molecules that are not in direct contact with the pore surface, i.e., nonphysisorbed molecules, could be released under our experimental conditions. Furthermore, in both vancomycin and ATP cases, the amount of drug release after 24 hours of the addition of DTT showed similar DTT concentration dependencies (FIG. 5b), indicating the rate of release is dictated by the rate of removing the CdS caps.

Example 3

Controlled-Release Studies of CdS-Capped, ATP-Encapsulated MSN with Neuroglia Cells (Astrocytes) In Vitro a. Methods
(i) Animals Wistar rats, raised at Iowa State University, were used for these experiments. Animal care and experimental protocols were in accordance with the guidelines and approval of the Iowa State University Committee on Animal Care.
(ii) Cell Cultures Enriched primary astrocyte cultures from neonatal ($P_0$ to $P_3$) rat cerebral cortex were prepared as previously described by Jeremic et al., *J. Neurochem.* 2001, 77:664. Briefly, freshly dissected cortical tissues from three animals were incubated 50 minutes at 37° C. in 2.00 mL of Earle's balanced salt solution (EBSS; Gibco-Invitrogen Co.) containing papain (1.54 mg/mL; Sigma-Aldrich Co.). After incubation, tissue was rinsed with EBSS solution and incubated for 5 minutes in trypsin-inhibitor solution (1 mg/mL; Gibco-Invitrogen Co.). After being rinsed, once with EBSS solution and once with culture medium (consisting of α-minimum essential medium (α-MEM; Gibco-Invitrogen Co.) supplemented with 10% heat-inactivated fetal bovine serum (FBS; Gibco-Invitrogen Co.) and 1.00 mL of penicillin-streptomycin solution (Sigma-Aldrich Co.) per 100 mL), the tissue was mechanically dispersed in culture medium by triturating through a fire-polished glass pipet. The cell suspension was transferred to sterile 15-mL centrifuge tubes and spun at 1000 g for 10 minutes. Cell pellets were resuspended in culture medium (α-MEM supplemented with 10% heat-inactivated FBS and 1.00 mL of penicillin-streptomycin solution per 100.00 mL) and plated in culture flasks. Cells were maintained at 37° C. in a humidified 5% $CO_2$/95% air atmosphere. Culture medium was changed every 2 to 3 days. When mixed cultures reached confluence (9-12 days), the flasks were shaken (260 rpm) for 90 minutes to remove microglia and dividing type I astroglia. After shaking the cells, medium was replaced, and the flasks were incubated for 1 hour to equilibrate with $CO_2$ in the fresh medium. Cultures were then shaken overnight (12-18 hours) at 260 rpm at 37° C. Cultures enriched in type I astroglia were obtained by trypsinizing (0.25%; Sigma-Aldrich Co.) attached cells for 5 minutes. Trypsin was inactivated by adding α-MEM supplemented with the 10% heat-inactivated FBS (serum contains protease inhibitors). Cells were plated on poly-L-lysine-coated coverslips (10.00 μg/mL; MW 100 000; Sigma-Aldrich Co.) at a density of $3.00 \times 10^4$ cells/$cm^2$. All experiments were performed on cells that had been in culture for 2-4 days after replating.
(iii) Characterization of Glial Cultures An antibody against glial fibrillary acidic protein (GFAP) was used to identify astrocytes following the procedure described in the subsequent Immunocytochemistry section. It was confirmed that glial cultures were neuron-free by using antibodies against the tubular protein MAP-2. In astrocyte-enriched cultures immunoreactivity for MAP-2 was absent, while neurons were immunopositive in parallel cultures that contained neurons.
(iv) Immunocytochemistry After fixation with 4% paraformaldehyde (Fisher Chemical) for 30 minutes at room temperature, cells were incubated for 30 minutes in a 50% goat serum solution containing 1% bovine serum albumin (BSA; Sigma-Aldrich Co.) and 100.00 mM L-lysine (Sigma-Aldrich Co.), to block nonspecific binding, and 0.4% Triton X-100 to permeabilize the membrane. Immunocytochemistry was performed using antibodies raised against glial fibrillary acidic protein (GFAP; 1:5000; Sigma-Aldrich Co.) and microtubule associated protein (MAP-2; 1:2000; Sigma-Aldrich Co.). Positive controls were established with these antibodies using cortical glia and neurons. Negative controls were established by omitting the specific antiserum. Antibody visualization was accomplished by the employment of the biotinylated secondary antibody, the Vectastain ABC kit (Vector) and the nickel-enhanced 3-3'-diaminobenzidine method. See Jeftinija et al., *Regul. Pept.* 1992, 39:123. Cells were dehydrated in graded alcohol, cleaned in xylene, and sealed with acrytol on glass slides.
(v) Intracellular Calcium Imaging The effect of experimental manipulation on the intracellular calcium concentration ($[Ca^{2+}]_i$) of cultured cells was evaluated by ratiometric imaging techniques. See Jeftinija et al., *J. Neurochem.* 1996, 66:676. Cells were loaded with Fura 2-AM (5.00 µM; Molecular Probes) for 40-60 minutes at 37° C.; 1.004 of 25% (w/w) of Pluronic F-127 (Molecular Probes) was mixed with every 4.00 nM of AM ester to aid solubilization of the ester into aqueous medium. Coverslips containing glial cells were washed with normal Hepes-saline solution and further incubated for 10 minutes at 37° C. to allowed de-esterification of Fura 2-AM. Normal Hepes-saline solution contains (in mM): NaCl 140.00, KCl 5.00, $MgCl_2$ 2.00, $CaCl_2$ 2.00, and HEPES (Sigma-Aldrich Co.) 10 (pH 7.4). All image processing and analysis were performed using an Attofluor system with Zeiss microscope. Background subtracted, rationed images (340/380 nm) were used to calculate the $[Ca^{2+}]_i$ according to a literature-reported method. See Grynkiewicz et al., *J. Biol. Chem.* 1985, 260:3440. Calibration was performed in situ according to the procedure provided by the Attofluor, using the Fura-2 Penta $K^+$ salt (Molecular Probes) as a standard. Using wavelengths of 340 and 380 nm, Fura 2-AM was excited, and the emitted light was collected at 520 nm.

b. Results

To demonstrate the biocompatibility and utility of the mesoporous silica particles of the invention for selective stimulation of certain cell types, ATP-loaded MSNs were introduced into an established astrocyte culture. It has been previously shown that ATP molecules evoke a receptor-mediated increase in intracellular calcium in astrocytes (Jeremic et al., *J. Neurochem.* 2001, 77:664; Neary et al., *Brain Res.* 1991, 566:89; and Zhu and Kimelberg, *J. Neurochem.* 2001, 77:530), which is an important regulatory mechanism for many intercellular communications and cooperative cell activities (Wang et al., *Anal. Chem.* 2000, 72:2001; and Newman and Zahs, *Science* (Washington, D.C.) 1997, 275:844). Astrocyte type-1 cultures were obtained from neonatal rats by following previously published protocol (Jeftinija et al., *J. Neurochem.* 1996, 66:676) to ensure the absence of neurons that complicate experimental interpretation. Phase-contrast microscopy indicated that cultures were indeed enriched in type-1 astrocytes and devoid of neurons. Immunocytochemistry experiments on these cells demonstrated that all the cultures are more than 95.0% immunopositive for glial fibrillary acidic protein (GFAP) and lacked MAP-2 immunoreactivity. The observed results further confirmed that these cultures are indeed type-1 astrocytes and not neurons. To determine the effect of ATP on cultured astrocytes, a ratiometric-imaging techniques (Jeftinija et al., *J. Neurochem.* 1996, 66:676; and Grynkiewicz et al., *J. Biol. Chem.* 1985, 260:3440) was used to monitor the glial calcium levels. Cells were loaded with the membrane-permeant $Ca^{2+}$-chelating fluorescent dye (Fura-2 AM; see Grynkiewicz et al., *J. Biol. Chem.* 1985, 260:3440), which is a widely used and highly sensitive indicator of intracellular calcium concentration ($[Ca^{2+}]_i$). The ATP-induced increases of $[Ca^{2+}]_i$ (calcium transients; see Grynkiewicz et al., *J. Biol. Chem.* 1985, 260:3440) represented by the color changes (increases of fluorescence) of the pseudocolor images of the cells were detected using an Attofluor system with Zeiss microscope.

To measure the effect of ATP released from the MSN system, astrocytes cultured in the presence of surface immobilized, CdS-capped MSNs with ATP molecules encapsulated inside of the mesoporous channels were first loaded with Fura-2 AM and then placed in a flow cell with a volume of 50.0 µL and a flow rate of 200.0 µL/minute. Perfusion application of ME (1 mM for 5 minutes) resulted in a drastic decrease in the fluorescence intensity of CdS at the areas of the ATP-loaded MSN piles (MSN-1 and MSN-2) indicating the CdS caps have been released and diffused away from the surface-bound MSNs. Furthermore, a pronounced increase in intracellular $[Ca^{2+}]_i$ represented by the color change of the pseudocolor images of Cell-1 and -2 and the corresponding upward shift of the red and blue curves of those two cells in the time course plot was observed. The observations suggested that the ATP molecules released from the mesoporous silica nanospheres located at the MSN-1 pile have reached their receptors on the cell surface of those astrocytes (for example, Cell-1 and -2) located at the downstream areas of the flow and thereby triggered the corresponding ATP receptor-mediated increase in intracellular calcium concentration. It is interesting to note that only the cells that were situated at the downstream areas relative to the MSN-1 pile are stimulated by the perfusion application of ME. Throughout the whole period of ME application, no obvious color changes could be observed in the pseudocolor images of those astrocytes that were located at the upstream areas, such as Cell-5. The result indicated that the intracellular calcium concentrations of those "upstream" astrocytes relative to the MSN-1 pile were not affected by the perfusional introduction of ME. Given that the flow direction is from the top to the bottom of these images, such a phenomenon could be attributed to the fact that the ATP molecules released from the immobilized piles of MSNs by the perfusion application of ME could not diffuse against the flow to reach and stimulate the "upstream" astrocytes (Cell-5).

To confirm that the increase of $[Ca^{2+}]_i$ was not induced by the ME or the CdS released from the MSNs, two control experiments were performed. First, an enriched astrocyte type-1 culture via the same protocol but without the presence of MSNs was obtained. The perfusion application of ME (1.0 mM for 5 minutes) to these cells showed no increase in $[Ca^{2+}]_i$. A high concentration of ATP (100.0 µM) was later introduced to these ME-treated astrocytes. All cells responded to the ATP application with obvious increases in $[Ca^{2+}]_i$. Clearly, the ME application did not stimulate the calcium channel activity of these astrocytes to create any noticeable increase in $[Ca^{2+}]_i$. Also, such ME treatments did not cause any obvious damage to these cells and they could still respond normally to ATP stimulation.

To determine the effect of the mesoporous silica particles of the invention on the $[Ca^{2+}]_i$ of astrocytes, enriched type-1 astrocytes were cultured in the presence of the capped mesoporous silica particles without ATP encapsulation. Perfusion application of 100.0 µM ATP only increased the fluorescence intensity ($[Ca^{2+}]_i$ increased) of the areas where the astrocytes are located, whereas the fluorescence intensity of those of capped mesoporous silica particles stayed constant before and after the ATP application. This result showed that apparently the astrocytes responded normally to ATP stimulation in the presence of the capped mesoporous silica particles. The culture of astrocytes and the capped mesoporous silica particles was then subjected to the same ME application. No detectable changes in $[Ca^{2+}]_i$ were observed in the areas of astrocytes, but drastic decreases of fluorescence could be noticed easily in those areas of the capped mesoporous silica particles indicating the release of CdS caps upon ME application.

Example 4

Gene Transfection a. Cell Cultures

Cortical and hippocampal neuronal cultures were prepared as described by Jeremic, A., et al., *J. Neurochem.* 2001, 77:664.

b. Cationic Dendrimer-Capped Mesoporous Silicate

Gene transfection was accomplished using a poly(amidoamine) dendrimer-capped mesoporous silicate (G2-PAMAM-MSN) carrier system, which was synthesized by the following procedures. A mercaptopropyl-derivatized mesoporous silica nanosphere material (thiol-MSN) was synthesized using a method similar to that described by Lin et al., *J. Am. Chem. Soc.* 2001, 123:11510; and Lin et al., *J. Am. Chem. Soc.* 2002, 124:9040. The thiol-MSN's (1.0 g) were dispersed in toluene with another layer of 3-mercaptopropyl group grafted on their exterior surface by introducing 0.189 mL of 3-mercaptopropyl-trimethoxysilane (MPTMS) at a ratio of 1 mmol MPTMS per gram of MSN. The resulting material was extensively washed with methanol. The surfactant template was further removed by acidic extraction in a solution of 7.5% v/v of HCl in methanol. The material was further functionalized with cysteine groups via a disulfide exchange of the thiol-MSN by reaction with 2-thiopyridyl-cystine hydrochloride ($5\times10^{-4}$ mol) in methanol. The surface coverage was determined to be $3.6\times10^{-4}$ mol cysteine per gram of MSN material. The cysteine-MSN (0.1 g) was first dispersed in a 0.7 mL phosphate buffer solution and added to a solution of G2-PAMAM dendrimer (0.69 mL) in 5% $NaHCO_3$ with 15 mg of EDC ($7.2\times10^{-5}$ mol) to obtain the desired G2-PAMAM-MSN. The product was washed with water and methanol and dried under high vacuum.

c. Plasmid DNA Vector for Gene Transfection

The pEGFP-C1 vector, an enhanced Green Fluorescent Protein (EGFP) vector for mammalian expression, was purchased from BD Biosciences, inc. The concentration of this plasmid DNA was determined by UV spectroscopy.

d. Methods

A typical complexation experiment of pEGFP-C1 with PAMAM-MSN was performed by the following procedures. First, an aqueous suspension of G2-PAMAM-MSN was prepared by dispersing the MSN particles in neurobasal media (1.5 mg MSN in 0.430 mL media) through several cycles of sonication/vortexing until a fine milky suspension was obtained. Aliquots of 18 μL of the suspension were incubated with different amounts of pEGFP-C1 vector to study the optimum ratio of complexation. The complexation extent was assessed by measuring the amount of DNA in the supernatant after 12 hours incubation by monitoring the fluorescence of EtBr after intercalation with the DNA in the supernatant. Only combinations that did not show any fluorescence increase vis-á-vis EtBr background fluorescence were used for cell transfection. These combinations were electrophoresed to ensure that the complexes are maintaining the excess positive charge necessary for approaching the membrane of cells and further internalization. Final DNA amount that were used in transfection experiments were 1, 2, 3 and 4 μg of pEGFP-C1 complexed with 18 μL of PAMAM-MSN suspension. The combinations correspond to an estimated N/P ratio (positive/negative charge ratio) of 75.5, 37.75, 25.16 and 18.87, respectively. The complex suspension was diluted in neurobasal media to a volume of 100 μL and deposit onto the cells cultures. Intracellular localization of Green Fluorescent Protein in living cells as well as in death cells was performed on a Leica confocal microscopic imaging system. Detection of GFP was carried out using an argon laser having standard FITC filter sets. The cells were imaged using a 60 plan oil immersion objective.

e. Results

Neurons emitting strong green fluorescence were observed upon photo-excitation (excitation wavelength=488 nm) of the cell cultures after 48 hours of gene transfection. The result indicated that the neurons were transfected by the DNA-associated PAMAM-MSN gene transfer system. Utilizing MSN as structural template to assemble a large quantity of the G2-PAMAM with low cytotoxicity on a mesoporous silicate surface for DNA complexation circumvents the difficulty of electrostatically recruiting enough G2-PAMAM to bind to one plasmid DNA molecule in homogeneous solution due to the entropy penalty. In addition, this method provides an important alternative to avoid using the conventional high generation cationic dendrimer which are often cytotoxic and cause damages to the targeted cells.

Examples 5 and 6

Examples 5 and 6 illustrate the synthesis of intermediate mesoporous silicates that can be capped to provide articles. In one embodiment, intermediate mesoporous silicates are described herein. In another embodiment, synthetic methods are described herein for preparing mesoporous silicates. In a particular embodiment, synthetic methods for controlling mesoporous silicate particle shape and size are described in Examples 5 and 6.

Example 5

Organic Functionalization and Morphology Control of Mesoporous Silicas via a Co-condensation Synthesis Method Since the discovery of surfactant micelle-templated synthesis of mesoporous silica materials, such as MCM-41/48 (Beck et al., *J. Am. Chem. Soc.* 1992, 114:10834; Kresge et al., *Nature* 1992, 359:710), SBA-15 (Zhao et al., *Science* 1998, 279:548), MSU-n (Bagshaw et al., *Science* 1995, 269:1242), KIT-1 (Ryoo et al., *J. Phys. Chem.* 1996, 100:17718), and FSM-16 (Inagaki et al., *Bull. Chem. Soc. Jpn.* 1996, 69:1449), many research efforts have focused on (i) preparing the organic/inorganic hybrids through functionalization of the exterior and/or interior surfaces and (ii) controlling the particle morphology. The success of such investigations will prompt the utilization of these materials in separation (Dai et al., *Angew. Chem., Int. Ed. Engl.* 1999, 38:1235); Lin et al., *Environ. Sci. Technol.* 2001, 35:3962); Yoshitake et al.; *Chem. Mater.* 2003, 15:1713; Yoshitake et al., *Bull. Chem. Soc. Jpn.* 2003, 76:847; Hossain and Mercier, *Adv. Mater.* 2002, 14:1053), sensor design (Lin et al., *J. Am. Chem. Soc.* 2001, 123:11510; Burleigh et al., *Chem. Mater.* 2001, 13:2537), catalysis (Soler-Illia Galo et al., *Chem. Rev.* 2002, 102:4093); Stein, *Adv. Mater.* 2003, 15:763; Davis *Nature*, 2002, 417:813; Corma, Chem. Rev. 1997, 97:2373; Price et al., *Dalton* 2000, 101-110; Ying et al., *Angew. Chem., Int. Ed. Engl.* 1999, 38:56; Sayari, *Chem. Mater.* 1996, 8:1840; Moller and Bein, *Chem. Mater.* 1998, 10:2950), and drug delivery (Lai et al., *J. Am. Chem. Soc.* 2003, 125:4451).

Although numerous synthetic approaches have been pursued and significant progress has been made in functionalization of MCM silicas with various organic groups, the current state-of-the-art methods, such as post synthesis grafting (Liu et al., *J. Phys. Chem. A* 2000, 104:8328) and organosiloxane/siloxane co-condensation (Stein et al. *Adv. Mater.,* 2000, 12:1403), need to be improved in order to control the amount and location of the incorporated functional groups. For example, the post synthesis grafting method typically results in inhomogeneous surface coverage because the introduced organic moieties congregate near the entries to the mesoporous channels and on the exterior surfaces (Lim and Stein, *Chem. Mater.* 1999, 11, 3285). While many organically functionalized mesoporous materials have been prepared via co-condensation (Lim and Stein, *Chem. Mater.* 1999, 11:3285; Fowler et al., *Adv. Mater.* 2001, 13:649; MacLachlan et al., *Chem.-Eur. J.* 2000, 6:2507; Fowler et al., *Chem. Commun.* 1997, 1769; Fowler et al., *Chem. Commun.* 1998, 1825; Hall et al., *Chem. Commun.* 1999, 201; Zub et al., *Mendeleev Commun.* 2001, 208; Lim et al., *Chem. Mater.* 1998, 10, 467; Lim et al., *J. Am. Chem. Soc.* 1997, 119:4090; Babonneau et al., *J. Mater. Chem.* 1999, 9:175 (1999); Moller et al., *Chem. Mater.* 1999, 11:665; Sayari and Hamoudi, *Chem. Mater.* 2001, 13:3151; Inagaki et al., *Nature* 2002, 416:304; Burleigh et al., *J. Phys. Chem. B,* 2001 105:9935; Burleigh et al., *Chem. Mater.* 2001, 13:4760, only few very recent investigations reported that spherical or tubular MCM-41 type silicas could be synthesized via incorporation of either mercaptopropyl, allyl, or aminopropyl functional groups (Sadasivan et al., *J. Mater. Chem.* 2003, 13:1023). Also, the previously reported co-condensation methods usually result in breakup of the structural integrity and long-range periodicity at surface coverages exceeding 25%.

A new synthetic method has been discovered that combines efficient organic functionalization of mesoporous silicas with control of particle morphology. The degree of functionalization and particle morphology are dictated by the concentration, molecular size and hydrophilicity/hydrophobicity of the organoalkoxysilane precursors. Mesoporous silicates were prepared using a co-condensation method based on sodium hydroxide-catalyzed reactions of tetraethoxysilane (TEOS) with various organoalkoxysilanes in the presence of a low concentration of cetyltrimethylammonium bromide (CTAB) surfactant. The organoalkoxysilanes included 3-aminopropyltrimethoxysilane (APTMS), N-(2-aminoethyl)-3-aminopropyltrimethoxysilane (AAPTMS), 3-[2-(2-aminoethylamino)ethylamino]propyl-trimethoxysilane (AEPTMS), ureidopropyltrimethoxysilane (UDPTMS), 3-isocyanatopropyltriethoxy-silane (ICPTES), 3-cyanopropyltriethoxysilane (CPTES), and allyltrimethoxysilane (ALTMS). In contrast to the Stöber process (Stoeber et al., *J. Colloid Interface Sci.* 1968, 26:62) or the recently reported controlled quenching method (Sadasivan et al., *J. Mater. Chem.* 2003, 13:1023), no organic co-solvents or instantaneous neutralization of alkaline solutions were required during the co-condensation reactions. By systematically varying the type and the amount of organoalkoxysilanes, a series of nanoparticles was obtained in form of spheres, rods, and hexagonal tubes. Hereinbelow, these materials are referred to as X-MP, where X describes the organoalkoxysilane precursor and MP stands for mesoporous particle. To examine the different mechanistic effects of the organoalkoxysilane-induced shape transformation, the structures of these mesoporous organic/inorganic hybrid materials were examined by powder X-ray diffraction (XRD) spectroscopy, field-emission scanning electron microscopy (FE-SEM), nitrogen adsorption-desorption surface analysis (BET isotherms and BJH pore size distributions), and thermogravimetric analysis (TGA). The incorporation of the organic functional groups was quantitatively studied by solid state NMR spectroscopy of $^{13}C$ and $^{29}Si$. Based on the observations of the morphological structures and the degree of organic functionalization, it appears that the formation of the mesoporous silica nanoparticles depends on the interaction between organoalkoxysilanes and CTAB micelles.

EXPERIMENTAL

The organoalkoxysilane precursors used for our co-condensation reactions contain a common trimethoxysilyl or triethoxysilyl terminal group and different organic functional groups, as depicted in Scheme 1. APTMS, AAPTMS, AEPTMS, UDPTMS, ICPTES, CPTES, ALTMS, TEOS and CTAB were purchased from Aldrich and used as received. The reaction mixture contained 1.0 CTAB: 8.16 TEOS: 1.05 organotrialkoxysilane of choice (unless specified otherwise): 2.55 NaOH: 4857 $H_2O$ based on the molar ratio. For example, in the case of AP-MP, the mixture of CTAB (2.0 g, 5.49 mmol), 2.0 M of NaOH(aq) (7.0 mL, 14.0 mmol) and $H_2O$ (480 g, 26.67 mol) was heated at 80° C. for 30 minutes to reach pH 12.3. To this clear solution, TEOS (9.34 g, 44.8 mmol) and APTMS (1.03 g, 5.75 mmol) were added sequentially and rapidly via injection. Following the injection, a white precipitation was observed after 3 minutes of stirring at about 550 rpm. The reaction temperature was maintained at 80° C. for 2 hours, then quenched by cooling the solution to room temperature. The products were isolated by filtration, washed with copious amount of water and methanol and dried under vacuum. The reaction yields of as-made products varied with respect to the choice of organoalkoxysilane and ranged from 38% to 65% of the starting weight of TEOS. An acid extraction was performed in methanol (100 mL) mixture of concentrated hydrochloric acid (1.0 mL) and as-made materials (1.0 g) at 60° C. for 6 hours. Resulting surfactant-removed solid products were filtered and washed with water and methanol and then dried under vacuum. Pure MCM-41 samples were prepared as reference using the same experimental conditions. The as-synthesized sample containing the surfactant is referred to as s-MCM-41, while the sample with CTAB removed is denoted as MCM-41.

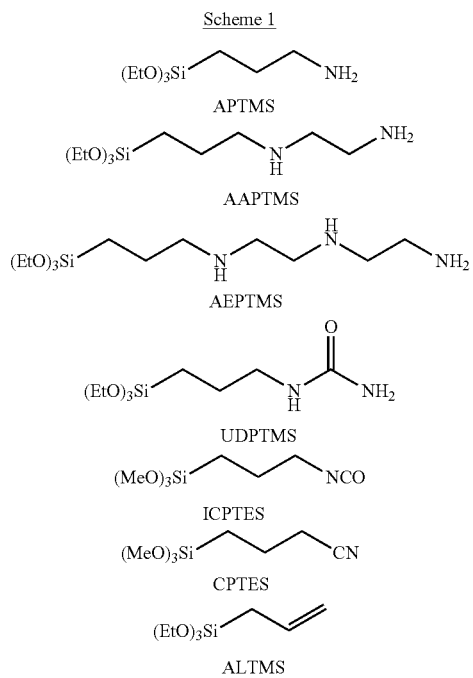

Scheme 1

Particle morphology was determined by scanning electron microscopy (SEM) using a Hitachi S4700 FE-SEM system with 10 kV accelerating voltage and 0.005 nA of beam current for imaging. For transmission electron microscopy (TEM) studies, a small aliquot was taken from a suspension of methanol and placed in a lacey carbon coat TEM grid, which was pulled through the suspension and allowed to dry in air. Thin sections of samples embedded in epoxide were obtained with ultramicrotomy (60-80 nm). The resulting sample was examined with a Philips model CM-30 TEM operated at 300 kV. The specimen was given no further treatment, as it appeared stable under beam bombardment.

Powder XRD experiments were performed on a Scintag XDS 2000 diffractometer using a Cu Kα radiation source. Low angle diffraction with a 2θ range of 1.0-10° was used to investigate the long-range order of the materials. The surface area and median pore diameter were measured using $N_2$ adsorption/-desorption measurements in a Micromeritics ASAP 2000 BET surface analyzer system. The data were evaluated using the Brunauer-Emmett-Teller (BET) and Barrett-Joyner-Halenda (BJH) methods to calculate the surface area and pore volumes/pore size distributions, respectively. Samples were prepared by degassing at 90° C. for 1 hour and then at 150° C. for 4 hours. TGA curves were recorded using a TA Instruments TGA 2950 thermogravimetric analyzer with a temperature ramp of 5° C./min under continuous flow of nitrogen (100 mL/min).

Solid-state nuclear magnetic resonance (NMR) experiments were performed on a Varian/Chemagnetics Infinity spectrometer at the frequencies of 79.5, 100.6 and 400.0 MHz for $^{29}Si$, $^{13}C$ and $^1H$ nuclei, respectively. $^{13}C$ and $^{29}S1$ nuclei were observed using direct polarization (DP) or by cross polarization (Pines et al., *J. Chem. Phys.* 1973, 59:569) (CP) from the neighboring $^1H$ nuclei. The samples were placed in 5 mm zirconia rotors and spun at 10 kHz in a doubly tuned Chemagnetics probe. The saturation recovery experiment, carried out for AL-MP and ICP-MP samples, yielded the $^{29}Si$ longitudinal relaxation times in the range 30 to about 65 s. In spite of slow relaxation, $^{29}Si$ DPMAS measurements were performed to obtain quantitative spectra for all samples. These experiments used excitation with a single 90° pulse of 2.1 μs followed by data acquisition under continuous wave (CW) $^1H$ decoupling at 65 kHz. Typically 270 scans were completed using pulse delay of 300 s.

The variable amplitude CPMAS scheme (Peersen et al., *J. Magn. Reson. A* 1993, 104:334) was used to enhance the polarization of observed nuclei and increase the repetition rate of data acquisition. During each cross polarization period, the rf field was ramped between 16 and 40 kHz using 2.4 kHz increments, whereas the $^{29}Si$ (or $^{13}C$) rf field was maintained at a constant level of approximately 36 kHz. The maximum $^1H \rightarrow {}^{29}Si$ polarization transfer was achieved using a contact time of approximately 10 ms, which is in agreement with previous studies performed for silicas (Maciel and Sindorf, *J. Am. Chem. Soc.* 1980, 102:7606). For $^{13}C$ nuclei, shorter contact times of 0.4 to about 1.5 ms were used. The $^1H$ rf magnetic fields of 90 kHz and 65 kHz were used for initial excitation and decoupling, respectively. The values of $^1H$ longitudinal relaxation time encountered in all mesoporous samples examined in this study did not exceed 1 s, which allowed for repetition time of 1.2 s to be used in the CPMAS experiments. Typically, 4K scans were accumulated for $^1H \rightarrow {}^{29}Si$ CPMAS, whereas $^1H \rightarrow {}^{13}C$ experiments required between 1K and 10K scans per spectrum. All chemical shifts were referenced to $SiMe_4$.

Results and Discussion

Organic Functionalization.

To simplify the analysis, a series of samples was prepared in which the amount of organoalkoxysilane used for the preparation was fixed at 12.8 mol % of the amount of TEOS. The $^1H \rightarrow {}^{13}C$ CPMAS spectra of these samples provide clear evidence that they were indeed functionalized as intended. The observed chemical shifts, listed in Table 1, agree well with those observed in homogeneous solutions of the corresponding precursors.

TABLE 1

$^{13}C$ chemical shifts (δc, in ppm from TMS) of organic groups obtained from $^1H \rightarrow {}^{13}C$ CPMAS spectra.

| AP-MP | | AAP-MP | | AEP-MP | | UDP-MP | | ICP-MP | | CP-MP | | AL-MP | | s-MCM-41 | |
|---|---|---|---|---|---|---|---|---|---|---|---|---|---|---|---|
| | $δ_C$ | | $δ_C$ | | $δ_C$ | | $δ_C$ | | $δ_C$ | | $δ_C$ | | $δ_C$ | | $δ_C$ |
| C1 | 9.1 | C1 | 8.5 | C1 | 8.7 | C1 | 9.0 | C1 | 8.8 | C1 | 10.5 | C1 | 18.8 | C16 | 22.7 |
| C2 | 20.6 | C2 | 19.8 | C2 | 19.4 | C2 | 23.1 | C2 | 20.7 | C2 | 18.3 | C2 | 130.8 | C15 | 26.1 |
| C3 | 42.3 | C3 | 37.2 | C3 | 38.5 | C3 | 42.9 | C3 | 42.2 | C3 | 18.3 | C3 | 114.2 | C3-14 | 29.8 |
| | | C5[a] | 49.8 | C5[b] | 49.1 | C5 | 162.2 | C5 | 160.4 | C4 | 118.4 | | | C2 | 31.8 |
| | | C6[a] | 45.0 | C6[b] | 44.5 | | | | | | | | | C1 | 66.4 |
| | | | | C8[c] | 56.1 | | | | | | | | | $NCH_3$ | 53.4 |
| | | | | C9[c] | 52.2 | | | | | | | | | | |

[a], [b], [c] The assignments are somewhat ambiguous for these three pairs of carbons (they may be reversed).

For example, the resonances at 6.5, and 45.3 ppm in the spectrum of APTMS dissolved in $CDCl_3$ (not shown) corresponded to those at 9.1 ppm (C1) and 42.3 ppm (C3) observed in AP-MP. The resonance at 28 ppm representing C2 exhibited a larger shift change toward higher field relative to the liquid state (20.6 ppm). The CPMAS spectrum of s-MCM-41 sample (FIG. 10h) consisted of several resonances due to CTAB, among which the peak at around 30 ppm, corresponding to carbons C3 through C14, is most intense. Two samples, CP-MP and AL-MP, contained detectable resonances from CTAB (marked with asterisks in spectra f and g), which comprised just a few % of the total $^{13}C$ intensity. The functionalization of silicas was further studied by TGA and solid state NMR of $^{29}Si$ (Table 2). In general, three or four distinct weight loss TGA profiles were found, including methanol, organic functional groups, and a small weight loss due to the dehydration of the surface hydroxyl groups. While the TGA data provided evidence of the existence of organic functional groups inside the pores, a direct, quantitative measure of the organic functionalization was provided by $^{29}Si$ DPMAS spectra. The resonances at around -59 and -68 ppm represented silicon atoms in positions ($\equiv SiO)_2Si(OH)R$ and ($\equiv SiO)_3SiR$, which are denoted $T^2$ and $T^3$, respectively (Maciel et al., *Encyclopedia of Nuclear Magnetic Resonance* 1996, 7:4370; Engelhardt and Michel, *High-Resolution Solid-State NMR of Silicates and Zeolites*, John Wiley & Sons: Chichester 1987; Lindner et al., *Angew. Chem., Int. Ed. Engl.* 1999, 38:2155). These silicon species were better observed using the $^{29}Si$ CP-MAS NMR method, which detected only the nuclei located within 2-3 bond lengths from the nearest hydrogen atoms. Note that the presence of $T^3$ and $T^2$ functionalities confirmed the existence of the covalent linkage between the organic groups and the silica surface. The resonance lines representing $Q^4$ (siloxane, ($\equiv SiO)_4Si$), $Q^3$ (single silanol, (≡SiO)$_2$SiOH) and Q$^2$ (geminal silanol, (≡SiO)$_2$Si(OH)$_2$) silicons were also observed in their usual spectral positions (Maciel et al., *Encyclopedia of Nuclear Magnetic Resonance* 1996, 7:4370; Engelhardt and Michel, *High-Resolution Solid-State NMR of Silicates and Zeolites*, John Wiley & Sons: Chichester 1987; Lindner et al., *Angew. Chem., Int. Ed. Engl.* 1999, 38:2155). The relative concentrations of all silicon sites were obtained by deconvolution of DPMAS spectra (Table 2). Assuming that all Q$^3$ and Q$^2$ sites decorated the interior walls of mesoporous silicas, the surface coverage (SC) of the mesopores with organic moieties could be estimated as SC=(T$^2$+T$^3$)/(Q$^2$+Q$^3$+T$^2$+T$^3$). As shown in Table 2, the SC values varied between 13% for UDP-MP and 33% for AL-MP. The measured loading efficiencies of the MP's synthesized with the organoalkoxysilanes containing hydrophobic functional groups, such as CPTES and ALTMS, were higher than those that contained the hydrophilic precursors, such as AAPTMS and AEPTMS. These results suggested that the organoalkoxysilanes with hydrophobic functional groups could better orient themselves around the water/micelle interface and intercalate these groups to the hydrophobic regions of the CTAB micelles during the co-condensation reactions.

droxysilyl group, which is hydrophilic. The other end of the molecule can be either hydrophilic or hydrophobic depending on the water solubility of the organic functional group involved.

The surface areas, pore volumes and pore size distributions of the MP materials were analyzed by the nitrogen adsorption-desorption techniques. All silicas exhibited characteristic Type IV BET isotherms consistent with the presence of cylindrical meso-scale pores. However, as outlined in Table 3, the BJH average pore diameters were different depending on the types of the incorporated organic functional groups. Again, utilization of the hydrophobic precursors yielded smaller pores. The powder XRD spectra of these materials featured an intense (100) reflection peak corresponding to lattice spacings in the range of 33.7 to 43.7 Å. Even though (210) peaks were not observed, the well resolved diffraction patterns characteristic of hexagonal MCM-41 silicas (Gulik et al., *J. de Physique II* 1995, 5:445), including (100), (110), and (200) peaks with the spacing ratio of 1:√3:√4, were observed in AP-MP, AAP-MP, CP-MP, ICP-MP and AL-MP. On the other hand, AEP-MP and UDP-MP (FIG. 14c, d) appeared to be disordered as evidenced by a broad peak at 4.52° and 4.10°, respectively, representing superimposed

TABLE 2

$^{29}$Si chemical shifts ($\delta_{Si}$, in ppm from TMS) and relative concentrations of T$^n$ and Q$^n$ groups obtained from $^{29}$Si DPMAS spectra.

| | AP-MP | | AAP-MP | | AEP-MP | | UDP-MP | | ICP-MP | | CP-MP | | AL-MP | | s-MCM-41 | | MCM-41 | |
|---|---|---|---|---|---|---|---|---|---|---|---|---|---|---|---|---|---|---|
| | $\delta_{Si}$ | % | $\delta_{Si}$ | % | $\delta_{Si}$ | % | $\delta_{Si}$ | % | $\delta_{Si}$ | % | $\delta_{Si}$ | % | $\delta_{Si}$ | % | $\delta_{Si}$ | % | $\delta_{Si}$ | % |
| T$^2$ | −59 | 4 | −65 | 4 | −56 | 1 | −62 | 2 | −57 | 1 | −58 | 2 | −64 | 3 | | | | |
| T$^3$ | −68 | 8 | −69 | 1 | −67 | 6 | −66 | 4 | −66 | 13 | −67 | 8 | −71 | 8 | | | | |
| Q$^2$ | −93 | 3 | −94 | 3 | −91 | 3 | −91 | 4 | −92 | 3 | −92 | 2 | −97 | 1 | −93 | 2 | −92 | 3 |
| Q$^3$ | −102 | 26 | −101 | 28 | −101 | 35 | −101 | 38 | −102 | 29 | −101 | 29 | −101 | 24 | −99 | 34 | −101 | 37 |
| Q$^4$ | −111 | 59 | −111 | 64 | −110 | 55 | −110 | 52 | −111 | 54 | −111 | 59 | −111 | 64 | −110 | 64 | −110 | 60 |
| T$_{surf}$ | | 29 | | 14 | | 16 | | 13 | | 30 | | 24 | | 33 | | | | |

Morphology Control.

The morphology and mesoporous structure of the organically functionalized MP materials were studied using FE-SEM and powder X-ray diffraction. The FE-SEM micrographs demonstrated a variety of particle shapes and sizes. For example, the AP-MP material showed a curved hexagonal shaped tubular morphology. Interestingly, upon replacing the APTMS with other structurally similar organoalkoxysilanes, such as AAPTMS and AEPTMS, the shapes transformed into twisted columns and micrometer-sized spheres, respectively. In contrast to smooth particle surface of AEP-MP, UDP-MP exhibited micron-sized spherical particles with raspberry-like bumpy rough surfaces. The ICP-MP material consisted of smallest spherical particles with diameters ranging from 100 to 500 nm. In the synthesis of CP-MP and AL-MP materials, hexagonal rod-shaped particles of different lengths and diameters were observed. The average particle size of CP-MP (1 μm in length and 500 nm in diameter) is larger than that of AL-MP (500 nm and 50 nm, respectively). As a rule, the particle sizes of materials prepared with the hydrophobic organoalkoxysilane precursors, such as ICPTES, CPTES, and ALTMS, appear significantly smaller than pure MCM-41, whereas the materials synthesized using more hydrophilic organoalkoxysilanes, such as AAPTMS, AEPTMS, and UDPTMS, yielded larger particles. Note that the co-condensation reactions took place in a basic aqueous solution (pH=12.3), therefore the trialkoxysilyl groups of these organoalkoxysilanes were hydrolyzed and converted to the trihy- (110), and (200) patterns. The TEM micrographs were consistent with this observation. In contrast, the TEM micrographs of materials prepared with hydrophobic organoalkoxysilanes, such as CPTES, showed well-organized mesopores packed in hexagonal symmetry.

TABLE 3

Structural properties of the organically functionalized mesoporous silica materials.

| Sample | D$_{100}$ (Å)[a] | a$_0$ (Å)[a] | S$_{BET}$ (m$^2$/g)[a] | V$_P$ (cm$^3$/g)[a] | W$_{BJH}$ (Å)[a] | d$_{pore\,wall}$ (Å)[a] | Amount of Organic groups (mmol/g) [b] |
|---|---|---|---|---|---|---|---|
| AP-MP | 39.8 | 46.0 | 721.7 | 0.45 | 23.7 | 22.3 | 1.7 |
| AAP-MP | 41.3 | 47.7 | 664.6 | 0.48 | 25.9 | 21.8 | 0.7 |
| AEP-MP | 38.4 | 44.4 | 805.8 | 0.57 | 26.0 | 18.4 | 1.0 |
| UDP-MP | 43.7 | 50.5 | 1022.4 | 0.78 | 28.6 | 21.9 | 0.9 |
| ICP-MP | 39.8 | 46.0 | 840.1 | 0.66 | 25.8 | 20.2 | 1.5 |
| CP-MP | 39.4 | 45.5 | 1012.5 | 0.68 | 23.5 | 22.0 | 1.4 |
| AL-MP | 33.7 | 38.9 | 1080.5 | 0.65 | 19.7 | 19.2 | 1.7 |
| MCM-41 | 38.1 | 44.0 | 767.1 | 0.55 | 25.5 | 18.5 | — |

[a] The BET surface area (S$_{BET}$), the mesopore volume (V$_p$), and the mean mesopore width (W$_{BJH}$) were obtained from the nitrogen adsorption/desorption data. The d$_{100}$ numbers represent the d-spacing corresponding to the main (100) XRD peak. The unit cell size (a$_0$) is calculated from the d$_{100}$ data using the formula a$_0$ = 2d$_{100}$/3$^{1/2}$. The pore wall thickness d$_{pore\,wall}$ = a$_0$ − W$_{BJH}$.
[b] The amounts of organic functional groups incorporated to the silica materials were estimated from the $^{29}$Si DPMAS.

Mechanism for the Shape Formation.

Similar organic precursors can yield very different particle morphologies, e.g., AAP-MP showed tubular-shaped particles while the AEP-MP exhibited exclusively spherical particles. Clearly, several different interactions, such as electrostatic attraction/repulsion, hydrogen bonding, and hydrophobic interaction, between the organoalkoxysilanes and surfactant molecules at the micelle/water interface contribute cooperatively to the observed drastic changes in particle morphology. In order to deconvolute some of these factors, the effect of the concentration of a selected organoalkoxysilane (AEPTMS) on the resulting particle shape and size was investigated.

The molar ratio of AEPTMS/TEOS was systematically varied from 1.28 to 12.8 mol %, while the concentrations of all the other chemicals introduced to the co-condensation reaction were fixed at the previously described levels. The incorporation of AEP was quantitatively determined by DPMAS and CPMAS$^{29}$Si NMR. As discussed earlier, the DPMAS spectra provided quantitative measure of the relative concentrations of $Q^n$ and $T^n$ functionalities. However, due to low concentration of $T^n$ species the SC values were not directly measured in this series of samples. Instead, we used the CPMAS spectra to evaluate the relative change of $T^n$ intensities versus the concentration of AEPTMS. The results showed that the concentration of AEP increased almost linearly as the initial AEPTMS/TEOS molar ratio changed from 1.28 to 12.8 mol %. The particle morphology and mesoporous structure of the resulting materials were analyzed by FE-SEM and TEM. The FE-SEM micrographs showed a concurrent transformation of the particle morphology from small kidney bean shaped rods to spheres, with elongated rods and ellipsoidal particles being observed at intermediate concentrations of AEPTMS. Furthermore, a noticeable increase of the average particle sizes of these materials could be observed at higher concentrations of AEPTMS. The TEM micrographs of the AEP-MP materials with low degrees of functionalization (1.28 and 6.43 mol %, respectively) revealed that the mesopores are uniformly aligned along the long axes of MP's despite of their different particle sizes. This is in contrast to the randomly oriented mesopores observed in the spherical AEP-MP's with the higher degree of functionalization.

In one embodiment, the invention provides a mesoporous silicate derived from APTMS, AAPTMS, AEPTMS, UDPTMS, ICPTES, CPTES, ALTMS, TEOS or CTAB, or a combination thereof.

Example 6

Tuning of Particle Morphology and Pore Properties in Mesoporous Silicas with Multiple Organic Functional Groups Example 6 illustrates a synthetic method that can control both multifunctionalization and morphology of mesoporous organic/inorganic hybrid materials by introducing different molar ratios of organoalkoxysilane precursors to base-catalyzed co-condensation reactions.

Recent advances in synthesizing organically functionalized mesoporous silica materials (Lim et al., *J. Am. Chem. Soc.* 1997, 119:4090; Stein et al., *Adv. Mater.* 2000, 12:1403; Fowler et al., *Chem. Commun.* 1997, 1769; Hall et al., *Chem. Commun.* 1999, 201; Fowler et al., *Chem. Commun.* 1998, 1825; Yang et al., *J. Am. Chem. Soc.* 2002, 124:9694; Inagaki et al., *Nature* 2002, 416:304; Fan et al., *Nature* 2000, 405:56) have highlighted the promising potential of utilizing these materials as building blocks to construct multifunctional microdevices for selective catalysis (Stein et al., *Adv. Mater.* 2000, 12:1403; Lin et al., *J. Am. Chem. Soc.* 2002, 124:9040; Ying et al., *Angew. Chem. Int. Ed.* 1999, 38:56; Sayari, *Chem. Mater.* 1996, 8:1840; Moller and Bein, *Chem. Mater.* 1998, 10:2950; He and Antonelli, *Angew. Chem., Int. Ed.* 2002, 41:214; Kageyama et al., *Science* 1999, 285:2113; Davis, *Nature* 2002, 417:813), adsorption (Dai et al., *Angew. Chem., Int. Ed.* 1999, 38:1235; Brown et al., *Chem. Commun.* 1999, 69; Feng et al., *Science* 1997, 276:923), and sensor (Lin et al., *J. Am. Chem. Soc.* 2001, 123:11510; Wirnsberger et al., *Chem. Commun.* 2001, 119; Descalzo et al., *Adv. Mater.* 2002, 14:966) applications. Further progress in such applications will rely on the ability to tune the extent of functionalization with multiple organic moieties and to control the particle morphology in order to direct the mass-transport properties of the resulting organic/inorganic hybrid materials. Morphology control of inorganic mesoporous silicas has been studied intensively ever since the first report of MCMs family a decade ago. Desired particle shapes have been obtained via pH control (Lin and Mou, *Acc. Chem. Res.* 2002, 35:927; Huo et al., *Adv. Mater.* 1997, 9:974; Ozin, *Chem. Commun.* 2000, 419), utilization of base catalysts (Cai et al., *Chem. Mater.* 2001, 13:258), and by the use of co-solvents (Anderson et al., *Chem. Mater.* 1998, 10:1490; Zhao et al., *Chem. Mater.* 2000, 12:275; Etienne et al., *New J. Chem.* 2002, 26:384; Schumacher et al., *Adv. Mater.* 1999, 11:1194), e.g., in a modified Stoeber process (Etienne et al., *New J. Chem.* 2002, 26:384; Schumacher et al., *Adv. Mater.* 1999, 11:1194).

Example 6 describes a novel synthetic process of the invention, in which various organoalkoxy-silane precursors introduced during the co-condensation reactions, rather than as co-solvents, are used for morphology control. An added advantage of this method is that it results in simultaneous anchoring of multiple functional groups to the mesopores (multifunctionalization). The roles and quantities of these moieties may be tailored independently and/or cooperatively for various applications, such as gatekeeping.

The FE-SEM images of two mesoporous silicas functionalized through the introduction of 3-[2-(2-aminoethylamino) ethylamino]propyl (AEP) and 3-cyanopropyl (CP) as organoalkoxysilane precursors showed that monofunctionalization with AEP or CP resulted in different particle shapes and sizes, i.e., spheres with an average particle diameter=3 µm and rods with an average particle size: L×W=1×0.2 µm. These materials were prepared by sodium hydroxide-catalyzed condensation reactions of tetraethoxysilane (TEOS) with AEP-trimethoxysilane (AEPTMS) or CP-triethoxysilane (CPTES), in the presence of a low concentration of cetyltrimethylammonium bromide (CTAB) surfactant.

A series of bifunctional materials in which the molar ratio between the AEPTMS and CPTES was varied systematically from 100% AEPTMS to 100% CPTES was also synthesized. The total amount of the organoalkoxysilanes (AEPTMS+CPTES) relative to TEOS was fixed at the level of 12.8 mol % in all samples. Herein, the monofunctionalized microparticles are referred to as AEP-MP (CP-MP) and the bifunctionalized materials are referred to as AEP/CP-MP.

The FE-SEM micrographs of the bifunctional AEP/CP-MP materials synthesized with different molar ratios of AEPTMS/CPTES showed only spherical particles. In contrast to the micron-sized AEP-MP, the average particle diameters of the bifunctional AEP/CP-MP spheres decreased as the relative ratio of AEPTMS/CPTES changed from 5/5 to 1/9. It is interesting to note that even in the 1/9 case (1.28 mol % of AEPTMS and 11.52 mol % of CPTES), no rod-like particles were observed, which is in stark contrast with CP-MP sample (12.8 mol % of CPTES). The presence of AEPTMS precursor in the co-condensation reaction played a crucial role in governing the particle shape of the resulting bifunctional materials.

To investigate the influence of the organoalkoxysilanes on the pore property and structure, the powder XRD diffraction patterns of the bifunctional samples were measured. The observed patterns exhibited a strong $d_{100}$ peak and a broad peak derived from the combination of $d_{110}$ and $d_{200}$ diffractions, most likely due to a disordered wormhole-like porous structure. This observed diffraction pattern is very similar to that of the AEP-MP material. Also, TEM micrographs revealed the disordered, wormhole pore structure in both AEP-MP and AEP/CP-MP.

Interestingly, the XRD and TEM measurements of the CP-MP rods showed a typical MCM-41 type of hexagonal symmetry of the mesopores packed in a parallel fashion along the long axis of the rod-shaped particles. These observations provided further evidence that the sample morphology is sensitive to the presence of AEPTMS during co-condensation.

$^{13}$C solid-state NMR was used to (i) obtain spectroscopic evidence for the presence of the organic functional moieties in the mesopores, (ii) confirm their chemical structure, and (iii) measure their relative concentration in bifunctionalized samples. The spectra were obtained at 9.4 T on a Varian/Chemagnetics Infinity spectrometer, using $^{1}$H-$^{13}$C cross polarization with magic angle spinning (CPMAS) (Pines et al., *J. Chem. Phys.* 1973, 59:569). The spectra demonstrated that the mesopores were indeed functionalized as intended Measurements of the "build-up" of carbon magnetization during cross-polarization revealed details about the molecular motions of both functional groups and allowed to measure their relative concentration in all samples. In AEP-MP, all $CH_2$ carbons were polarized with a time constant $\tau_{CH}$ on the order of 60 μs, which is typical for such functional groups in rigid molecules. A similar time constant has been found for the C1 carbon in CP-MP. However, the evolution of resonance at 19 ppm in this sample involved two time constants of approximately 100 and 700 μs. This result showed that the C2-$H_2$ and C3-$H_2$ groups in CP-MP experienced increasing mobility, which weakened the $^{1}$H-$^{13}$C dipolar coupling and inhibited the cross polarization process. The $\tau_{CH}$ value of 5 ms observed for carbon C4 was consistent with the nitrile end of CP-MP being the most mobile.

Measurements also showed that in the AEP/CP-MP samples the cross polarization dynamics was the same, within the experimental error, as for the corresponding carbon species in AEP-MP and CP-MP. This allowed the physical mixture of AEP-MP with CP-MP in a known molar ratio to be used as the intensity standard for quantitative analysis of the spectra of bifunctionalized samples. Two unique resonances, at around 48 ppm in AEP (carbons C4-C7) and at 120 ppm in CP (carbon C4), offered best indicators of both functionalities.

In order to investigate the chemical accessibility of the organic functional groups, the $Cu^{2+}$ adsorption capacity of representative samples was examined (Burleigh et al., *Chem. Mater.* 2001, 13:4760). Because of the chelate effect of the diethylene triamine moiety of the AEP group, significantly higher $Cu^{2+}$ adsorption capacities for the materials with higher amount of AEP were anticipated. Indeed, the results indicated that the AEP-MP and CP-MP materials showed adsorptivities of 0.284 and 0.017 mmol/m$^2$, respectively. The corresponding values for bifunctional 5/5 and 1/9 AEP/CP-MP silicas were 0.073 and 0.028 mmol/m$^2$. However, the $Cu^{2+}$ adsorption capacity increased by a factor of only 2.6 between the 1/9 to 5/5 AEP/CP-MP samples, whereas solid state NMR showed an 8-fold increase of the relative AEP/CP ratio in these materials. Given that the total loading of both organic groups was fixed at 12.8 mol %, these results indicated that the chemical accessibility of organic functional groups did not increase linearly with the amount of AEP groups in bifunctional silicas. The CP functionality, which is hydrophobic in nature, might have played an active role in decreasing the adsorption capacity per AEP group.

Example 7

Gene Transfection Via Polyamidoamine Dendrimer-Capped Mesoporous Silicates

A novel gene transfection system is provided, where second generation (G2) PAMAMs are covalently attached to the surface of an MCM-41 type mesoporous silica nanosphere (MSN) material. The G2-PAMAM-capped MSN material (G2-MSN) was used to complex with a plasmid DNA (pEGFP-C1) that encodes for an enhanced green fluorescence protein. The gene transfection efficacy, uptake mechanism, and biocompatibility of the G2-MSN system with various cell types, such as neural glia (astrocytes), human cervical cancer (HeLa), and Chinese hamster ovarian (CHO) cells were investigated.

Recent reports in the literature have demonstrated that polyamidoamine (PAMAM) dendrimers can serve as non-viral gene transfection reagents (Dennig and Duncan, *Rev. Mol. Biotechnol.* 2002, 90:339-347, and the references therein; Esfand and Tomalia, *Drug Discovery Today* 2001, 6:427). However, only those PAMAMs of high generations (G>5) have been shown to be efficient in gene transfection. The required procedures for the synthesis and purification of these high G PAMAMs are usually tedious and low-yielding. In contrast, the low G PAMAMs (G<3) are typically nontoxic and easily synthesized. Despite these benefits, the smaller molecular sizes and the limited surface charges of the low G PAMAMs prohibit efficient complexation with plasmid DNAs in solution due to the entropy penalty.

The G2-PAMAM-capped MSN material (G2-MSN) was used to complex with a plasmid DNA (pEGFP-C1) that is encoding for an enhanced green fluorescence protein (Subramanian and Srienc, *J. Biotechnol.* 1996, 49:137). The gene transfection efficacy was investigated, as well as the uptake mechanism, and biocompatibility of the G2-MSN system with various cell types, such as neural glia (astrocytes), human cervical cancer (HeLa), and Chinese hamster ovarian (CHO) cells.

In contrast to other recently reported silica nanoparticle-based gene transfer systems (Luo and Saltzman, W. M. *Nat. Biotechnol.* 2000, 18:893; Kneuer et al., *Bioconjugate Chem.* 2000, 11:926; He et al., *J. Am. Chem. Soc.* 2003, 125:7168; Luo et al., *J. Controlled Release* 2004, 95:333), the mesoporous structure of the MSN material allows membrane impermeable molecules, such as pharmaceutical drugs, nucleic acids, and fluorescent dyes, to be encapsulated inside the MSN channels (Lai et al., *J. Am. Chem. Soc.* 2003, 125:4451; Mal et al., *Nature (London)* 2003, 421:350). The system renders possible a universal transmembrane carrier for intracellular drug delivery and imaging applications. Experimental 1. Preparation of G2 PAMAM MSN.

To construct the G2-MSN gene transfer system, an MSN material with an average particle size of 250 nm (avg. pore diameter=2.7 nm) was synthesized. The MCM-41 type mesoporous silica nanosphere (MSN) material was prepared by the methods disclosed by Lai, et al. (Lai et al., *J. Am. Chem. Soc.* 2003, 125:4451). 3-Isocyanatopropyltriethoxysilane (0.25 mL, 1 mmol) was grafted onto the pore surface of the MSN (1 g) in 80 mL of refluxing toluene for 20 hours to yield the isocyanatopropyl-functionalized MSN (ICP-MSN) material.

1a. Synthesis of ICP-MSN.

N-Cetyltrimethylammonium bromide (CTAB, 1.00 g, 2.74 mmol) was dissolved in 480 mL of nanopure water. Sodium hydroxide aqueous solution (2.00 M, 3.50 mL) was introduced to the CTAB solution and the temperature of the mixture was adjusted to 353 K. Tetraethoxysilane (TEOS, 5.00 mL, 22.4 mmol) was added dropwise to the surfactant solution under vigorous stirring. The mixture was allowed to react for 2 hours to give rise to a white precipitate. This solid crude product was filtered, washed with deionized water and methanol, and dried in air to yield the as-synthesized MSN. To remove the surfactant template (CTAB), 1.50 g of the as-synthesized MSN was refluxed for 24 hours in a methanolic solution of 9.00 mL of HCl (37.4%) in 160.00 mL methanol. The resulting material was filtered and extensively washed with deionized water and methanol. The surfactant-free MSN material was placed under high vacuum to remove the remaining solvent from the mesopores. MSN (1.00 g) was refluxed for 20 hours in 80.00 mL of anhydrous toluene with 0.25 mL (1.00 mmol) of 3-isocyanatopropyltriethoxysilane to yield the 3-isocyanatopropyl-functionalized MSN (ICP-MSN) material.

1b. Synthesis of G2-MSN without Texas Red.

The purified ICP-MSN (0.15 g) was added to anhydrous ethanol (3.00 mL). A second-generation (G2) polyamidoamine dendrimer (PAMAM, 2.00 mL, 0.11 mmol) was then added to the ICP-MSN ethanol solution. The amino groups of the G2-PAMAM were allowed to react with the ICP functional groups present on the surface of MSN for 20 hours at room temperature to yield the G2-PAMAM-capped MSN material (G2-MSN). The resulting G2-MSN material was filtered and washed thoroughly with ethanol, methanol and acetone and dried under high vacuum.

1c. Synthesis of Texas Red-loaded G2-MSN.

To visualize the interaction of MSNs and cells, a G2-MSN material loaded with a fluorescent dye (Texas Red™) was prepared. ICP-MSN (0.15 g) was added to an anhydrous ethanol solution of Texas Red™ (5 mM), and stirred for 20 hours. The amine-terminated G2-PAMAMs were used as caps to encapsulate Texas Red molecules inside the porous channels of ICP-MSN. An ethanol solution of G2-PAMAM (0.11 mmol) was added to the MSN/Texas Red solution for 20 hours to form urea linkage between amines of PAMAM and ICP groups of MSN. The structure of G2-PAMAM-capped, Texas Red-encapsulated MSN were scrutinized by XRD, SEM, TEM, $N_2$ sorption isotherms, and $^{13}C$ CP-MAS NMR spectroscopy.

A typical synthesis of Texas Red-loaded G2-MSN is as follows. The purified ICP-MSN (0.15 g) was added to an anhydrous ethanol solution (3.00 mL) of Texas Red™ (5.00 mM, Molecular Probe). The solution mixture was stirred at room temperature for 20 hours to allow the Texas Red to be encapsulated by the ICP-MSN. A second-generation (G2) polyamidoamine dendrimer (PAMAM, 2.00 mL, 0.11 mmol) was then added to the ICP-MSN/Texas Red solution. The amino groups of the G2-PAMAM were allowed to react with the ICP functional groups present on the surface of MSN for 20 hours at room temperature to yield the Texas Red-loaded, G2-PAMAM-capped MSN material (Texas Red-loaded G2-MSN). The resulting G2-MSN material was filtered and washed thoroughly with ethanol, methanol and acetone and dried under high vacuum. To ensure the complete removal of Texas Red molecules physisorbed on the exterior surface of the G2-MSN, a Soxhlet extraction in ethanol was performed for 20 hours. The resulting solid was filtered and dried in air.

2. Characterization of ICP-MSN and G2-MSN.

2.1. Powder X-Ray Diffraction

Powder X-Ray diffraction patterns of purified ICP-MSN, G2-MSN, and Texas Red-loaded G2-MSN materials showed that both ICP-MSN and G2-MSN materials exhibit the typical diffraction patterns of MCM-41 type mesoporous silica with hexagonal symmetry. The changes in the Tex Red-loaded G2-MSN diffraction pattern might be caused by pore filling effects.

Table 4 summarizes the powder X-ray diffraction patter data of the ICP-MSN, G2-MSN, and Texas Red-loaded G2-MSN samples.

TABLE 4

Powder X-Ray diffraction patterns

| Sample | Powder XRD Diffraction | | |
|---|---|---|---|
|  | $d_{100}$ (Å) | $d_{110}$ (Å) | $d_{200}$ (Å) |
| ICP-MSN | 40.88 | 23.61 | 21.05 |
| G2-MSN | 40.88 | 23.48 | 21.05 |
| Tex Red-loaded G2-MSN | 39.41 | — | — |

2.2. Nitrogen Adsorption/Desorption Isotherms

BET nitrogen adsorption/desorption isotherms (a), and BJH pore size distributions (b) of MSN, ICP-MSN, G2-MSN, and Texas Red-loaded G2-MSN materials showed that ICP-MSN and G2-MSN materials did not exhibit any hysteresis, indicating there was no xerogel formation on the exterior surface of the MSN upon surface functionalization.

Table 5 summarizes the BET and BJH data obtained from MSN, ICP-MSN, G2-MSN, and Texas Red-loaded G2-MSN samples.

TABLE 5

BET and BJH parameters

| Sample | Nitrogen Sorption Isotherms | | |
|---|---|---|---|
|  | BET Surface Area ($m^2/g$) | BET Pore Volume (mL/g) | BJH Pore diameter (Å) |
| MSN | 959 | 0.865 | 27.3 |
| ICP-MSN | 842 | 0.755 | 27.2 |
| G2-MSN | 568 | 0.481 | 22.6 |
| Texas Red-loaded G2-MSN | 167 | 0.190 | 18.8 |

2.3. Solid-State $^{13}C$ CP-MAS NMR $^{13}C$ solid state CP-MAS NMR spectra of the ICP-MSN and G2-MSN materials showed that propyl-carbamic acid impurity from the hydrolyzed isocyanopropyl groups of the ICP-MSN was observed in the spectrum of ICP-MSN. Solid-state $^{13}C$ CP-MAS NMR spectra were obtained at 75.47 MHz on a Bruker MSL300 spectrometer equipped with Bruker 4 mm rotor MAS probe. Magic-angle sample spinning rate was maintained at 10 KHz for $^{13}C$ in order to minimize the spin band due to the high anisotropic chemical shifts of aromatic carbons. The NMR spectra consisted of 5,000 to 20,000 acquisitions with cross polarization times of 3 ms ($^{13}C$) and pulse repetition times of 15 s ($^{13}C$). All chemical shifts reported are referenced to internal liquid $Me_4Si$ (TMS).

2.4. Scanning and Transmission Electron Micrographs (SEM and TEM) of G2-MSN

SEM and TEM (300 kV) micrographs of the G2-MSN showed the spherical shape of the silica particles and the mesoporous channel structure of the G2-MSN, respectively.

3. G2 MSN and pEGFP-C1 DNA Complexation.

To study the complexation between the pEGFP-C1 DNA and G2-MSN in different weight ratios at physiological pH, agarose gel electrophoresis (0.8%, 45 mM TBE buffer) of pEGFP-C1 in the presence of G2-MSNs was performed for 3.5 hours at 155 V. The electrophoretic shifts for pEGFP-C1 in the absence of G2-MSN and presence of increasing amounts of G2-MSN demonstrated that the G2-MSN could bind with plasmid DNA to form stable DNA-MSN complexes at weight ratios larger than 1:5, as illustrated by the retention of pEGFP-C1 around the sample wells. To examine whether the G2-MSN are efficient in protecting pEGFP-C1 DNA against enzymatic cleavage, a restriction endonuclease (BamHI, 20 units) was introduced to the DNA as well as the stable DNA-MSN complexes containing 1 μg of DNA. The samples were incubated for 12 hours at 37° C., followed by deactivation of enzyme at 70° C. for 15 minutes. Free pEGFP-C1 was digested and cleaved by BamHI, whereas the DNAs when complexed with MSNs were not cleaved by the enzyme under the same condition. Interestingly, pEGFP-C1 DNA was digested by BamHI in the presence of MSN without PAMAM caps. The results suggested that the abundant positive charges on the PAMAM-capped G2-MSN were essential for stabilizing the DNA-MSN complexes against enzymatic digestion.

4. Gene Transfection Experiments of DNA-Coated G2-MSNs.

To investigate the transfection efficacy of the system, G2-MSNs without Texas Red (10 μg) were mixed with 1 μg of pEGFP-C1 DNA, as described in section 4.1, below. The MSN/DNA suspension (60 μL/well) was further added to the cells on 24-well plates ($6 \times 10^4$ cells per well, in 0.6 mL growth medium) and incubated for 4 hours at 37° C. The cells were then washed with PBS buffer and cultured with DMEM+10% calf serum (CS) medium and antibiotics for 2 days. The transfected cells were trypsinized and resuspended in 0.5 ml of PBS for direct flow cytometric analysis to evaluate the expression of GFP (see Subramanian and Srienc, *J. Biotechnol.* 1996, 49:137). Control experiments utilizing cultures of untransfected cells and "mock"-transfected cells (cells incubated with MSNs without pEGFP-C1) were measured with an EPICS-ALTRA flow cytometer, using a 488 nm laser for GFP excitation. Significant GFP-expression was observed.

4.1. Materials and Methods

Human cervical cancer (HeLa) and Chinese Hamster Ovarian (CHO) cell lines were obtained from American Tissue Culture Collection (ATCC). HeLa and CHO cells were maintained in T75 flasks using DMEM (Dulbbecco's modified Eagle's medium) supplemented with 10% CS serum, 2 mM L-glutamine, 100 U/mL penicillin, 100 μg/μL streptomycin, and 1 μg/μL gentamycin. All cells were passaged every 2-3 days. A red-shifted variant of GFP expressed from pEGFP-C1 (Clontech, Palo Alto, Calif.) was used as reporter protein. All plasmids were amplified in the *E. coli* strain DH5a and purified according to the manufacturer's protocol (Qiagen, USA). The isolated DNA was resuspended in Tris-EDTA (pH 8.0) at a concentration of 1 μg/A.

HeLa cells were first seeded onto 24-well plates ($6 \times 10^4$ cells per well, in 0.6 mL growth medium) and 6-well plates ($2 \times 10^5$ cells per well, in 1.5 mL growth medium) 24 hours prior to the experiment. The former plating (24-well) was used for transfection efficiency measurements. The 6-well plating was used for imaging studies.

In a typical transfection experiment, 1 μg of plasmid DNA encoding GFP was added to 10 μg of G2-MSN suspension obtained by dispersing the nanosphere material in 30 μL of HEPES buffer solution (10 mM HEPES, pH 7.4). The mixture was incubated for 2 hours at 4° C. Thirty μL of 100 mM $CaCl_2$(aq) was added to the previous mixture for 2 hours at 4° C. (Haberland et al., *Biochim. Biophys. Acta* 1999, 1445:21; Lam et al., *Biochim. Biophys. Acta* 2000, 1463:279). The MSN/DNA suspension (60 μL/well) was further added to the cells on 24-well plates and incubated for 4 hours at 37° C., followed by the removal of the transfection mixture (residual MSN/DNA complexes). The transfected cells were then washed with PBS buffer and cultured with DMEM+10% calf serum (CS) medium and antibiotics for 2 days for gene expression analysis or image studies.

To compare the transfection efficiency of our G2-MSN system with other commercially available transfection reagents, three different reagents, PolyFect®, SuperFect® (Qiagen, Valencia, Calif.) and Metafectene® (Biontex, Germany), were used to transfect the aforementioned cell types under the same experimental condition. First, 8 and 5 μL of the stock solutions of PolyFect® (2 mg/mL) and SuperFect® (3 mg/mL), respectively, were added to a 30 μL of serum-free medium (DMEM) containing 1 μg DNA. The solutions were incubated at room temperature for 15 minutes to allow the formation of stable complexes between DNA molecules and transfection reagents. The complexes were then added to a culture of HeLa cells in a 24-well plate with a cell density of $6 \times 10^4$ cells/well that contained 350 μL of pre-warmed DMEM+10% CS medium and antibiotics. After 4 hours of incubation, the transfection medium was discarded and replaced with fresh growth medium (DMEM+10% CS medium and antibiotics). The cells were evaluated for expression of the enhanced green fluorescent protein (EGFP) by flow cytometry after 48 hours post-transfection.

For Metafectene®, the protocol involved the addition of 5 μL stock solution of Metafectene® (1 mL stock solution was used as received from Biontex, Germany) to a 30 μL of serum-free medium (DMEM) containing 1 μg DNA. This solution was incubated at room temperature for 15 minutes to allow complex formation before the addition to the cells. The complexes were added to the aforementioned HeLa cell wells that contained 350 μL of pre-warmed, serum-free DMEM. After 4 hours of incubation, the transfection medium was discarded and replaced with fresh growth medium (DMEM+10% CS medium and antibiotics). Cells were evaluated for expression of the enhanced green fluorescent protein (EGFP) by flow cytometry after 48 hours post-transfection. Significant GFP-expression was observed.

4.2. Flow Cytometric Analysis of Transfected Cells

To compare the transfection efficiency of G2-MSN with other commercial transfection reagents, pEGFP-C1 transfection experiments were conducted on HeLa cells with Poly-Fect, SuperFect, and Metafectene under the same experimental condition. Flow cytometric measurements were performed immediately after collection of cultured cells. All cells were trypsinized and resuspended in 0.5 mL of PBS before the FACS analysis. Positive and negative control experiments utilizing cultures of untransfected cells (HeLa cells only) and "mock"-transfected cells (cells incubated with MSNs without pEGFP-C1 plasmid) were measured with an EPICS-ALTRA flow cytometer (Beckman Coulter, Miami, Fla.), using a 488 nm laser for GFP excitation. GFP fluorescence was detected using PMT2 in conjunction with a 525 nm band-pass filter. An electronic gate was set around cells based on the forward and side scatter properties of the population, and a minimum of 10,000 gated events per sample were collected and stored in list mode files. Data analysis was performed with FlowJo software (Tree Star, Ashland, Oreg.). Scatter-gated events are displayed herein as single parameter histograms of logarithmic GFP fluorescence. All experiments were performed in quadruplicate. Untransfected cells were used for background calibration. The average transfection efficiencies of different transfection reagent systems on HeLa cells were summarized in Table 6.

TABLE 6

Transfection Efficiency of different transfection reagents on HeLa cells.

| Transfection Reagent | Efficiency (%) |
| --- | --- |
| G2-MSN | 35 ± 5 |
| PolyFect ® | 15 ± 2 |
| SuperFect ® | 10 ± 2 |
| Metafectene ® | 16 ± 2 |

Flow cytometry analysis of the transfection of pEGFP in HeLa cells with G2-MSN showed efficiencies of 35±5% (G2-MSN), 15±2% (PolyFect), 10±2% (SuperFect), and 16±2% (Metafectene). The results indicated that G2-MSN can offer competitive transfection efficiency to various cell types.

4.3. Mammalian Cell Membrane Permeability

To examine the mammalian cell membrane permeability, Texas Red-loaded G2-MSNs were introduced to GFP-transfected rat astrocytes.

4.3.1. Confocal Microscopy Imaging of Transfected Cells

HeLa cells were grown on coverslips in a 6-well culture plate. All of the samples were washed three times with PBS buffer and fixed with formaldehyde in PBS (3.7%). The samples were excited by an argon laser ($\lambda_{ex}$=488 nm) and the images were subject to a longpass filter ($\lambda$=515 nm). Images were captured on an inverted Nikon Eclipse microscope connected to a Prairie Technologies (Middleton, Wis.). Scanning Laser Confocal Microscope controlled by Prairie Technologies software. Images were analyzed using Metamorph software (Universal Imaging, West Chester, Pa.).

Orthogonal images indicated that cells were packed in a monolayer and no multilayer of cells was observed.

4.3.2. Transmission Electron Micrographs of G2-MSN Transfected Cells

To study the endocytosis of G2-MSN, cells on coverslips were fixed at selected time-points with 2% glutaraldehyde and 2% paraformaldehyde in PBS buffer, pH 7.2, at 4° C. for 48 hours. The samples were then washed in PBS followed by washing in 0.1 M cacodylate buffer, pH 7.2, and post-fixed in 1% osmium tetroxide in 0.1 M cacodylate buffer for 1 hour at room temperature. The samples were then washed briefly in dH$_2$O and dehydrated through a graded ethanol series and cleared using ultra pure acetone and infiltrated and embedded with EPON epoxy resin (EmBed 812, Electron Microscopy Sciences, Ft. Washington, Pa.). Coverslips were embedded by inverting the slips (cell side down) onto upright beem capsules and polymerized at 60° C. for 24 hours and 70° C. for 24 hours. The coverslips were removed from the resin with liquid nitrogen. Thin sections were made using a Reichert Ultracut S ultramicrotome (Leica, Deerfield, Ill.) and collected onto copper grids and stained with 4% uranyl acetate in 50% methanol followed by Sato's lead stain. Images were collected using a JEOL 1200 EMI scanning and transmission electron microscope (Japan Electron Optics Laboratory, Peabody, Mass.) at 80 kV with a Megaview III digital camera and SIS Pro software (Soft Imaging System, Corp., Lakewood, Colo.).

TEM micrographs showed G2-MSNs (black dots) endocytosed by Chinese hamster ovarian (CHO), human cervical cancer (HeLa), and neural glia (astrocytes) cells. Subcellular organelles, e.g., mitochondria and Golgi, were observed with MSNs nearby. The measured distance between channels (including the pore walls) is consistent with the BJH average pore diameter of 3-4 nm from $N_2$ sorption isotherms.

The confocal fluorescence micrograph clearly illustrated that the G2-MSNs (red fluorescent dots) penetrated cell membrane via endocytosis and entered into the cytoplasm of a green fluorescent neural glia cell. Transmission electron micrographs of the post-transfection cells also provided direct evidence that a large number of G2-MSNs were endocytosed by all three types of cells. It is noteworthy that many subcellular organelles, such as mitochondria and Golgi, were observed with MSNs nearby. Given that these organelles disappear rapidly upon cell death, the result strongly suggested that the MSNs were not cytotoxic in vitro.

4.4. Cell Growth Studies

To further investigate the biocompatibility of G2-MSN, the cell growth profiles of HeLa cultures with and without G2-MSNs (0.1 mg/mL) was compared. The in vitro biocompatibility of the G2-MSN, growth studies were performed for HeLa and CHO cells. Two series of experiments were designed for both types of cells: one series studied the natural cells growth (without MSNs) and the other was monitored after MSNs application. All experiments were performed in triplicate. To ensure enough space and media for cell growing, the cells were seeded in T-25 flasks. In the experiments without MSNs, 18 flasks were loaded with the same amount of cells for each cell type. After allowing 24 hours for cell adhesion, the cells were analyzed everyday (3 flasks per day) for 6 days. The cells were trypsinized and counted by using a Guava ViaCount® assay (Guava Technologies, Inc, USA). In the experiments with G2-MSNs, the cells were seeded for 24 hours prior to the incubation with MSNs at 0.1 mg/mL concentration in DMEM+10% CS (calf serum) and antibiotics for 4 hours. After the 4 hour incubation, the cells were washed twice with PBS buffer and incubated for another 6 days. The aforementioned cell counting procedures were followed. All experiments were performed in triplicate (3 flasks/day). During the 6-day growth period, the cells were periodically examined under a phase contrast microscope. The cells were added with fresh media every other day or upon pH fluctuations (Phenol Red dye was used as pH indicator). The doubling times of the cell density of HeLa cells without and with MSNs were calculated from the semilog plots to be 20 hours and 24 hours, respectively. The doubling times of CHO cells without and with MSNs were calculated to be 23 hours and 40 hours, respectively. ($R^2 \geq 97\%$ in the case of HeLa cells, whereas $R^2 \geq 90\%$ for CHO cells).

The cell growth from those cultures with and without G2-MSNs were very similar indicated that the increase of numbers of cells was not hindered by the presence of G2-MSNs. The G2-MSN material can thus serve as a new transmembrane delivery system for many biomedical applications.

Example 8

Use of Particles to Transform Plant Cells

Plant genetic engineering relies mostly on biolistic and *Agrobacterium*-mediated transformation technologies. Both techniques allow DNA delivery into plant cells and subsequent integration into the genome. Recently, the development of nanomaterials such as MSN was shown to deliver marker genes into animal cells (Radu et al., *JACS* 2004, 126:13216). The distinct feature of this nanoparticle is that it can both deliver DNA as well as chemicals encapsulated in the particles. Controlled release of the filling substance is also possible using this material (Gruenhagen et al., *Appl. Spectrosc* 2005, 59:424).

As described below, this material can be used for transforming tobacco mesophyll protoplasts (cell wall "free") and immature maize embryos. Transgene expression was observed both transiently and stably. In addition, chemicals encapsulated in the MSN can be controlled-released in planta when appropriate induction reagents are applied. The use of MSN to deliver transgenes and various substances simultaneously into plant cells opens a wide range of applications for plant genomics.

Two strategies were employed to introduce the MSN in plant cells: physical delivery and direct uptake. The first approach is based on the same rational as for gold particles bombardment: MSN, coated with DNA, works as a carrier. The second strategy relies on endocytosis (Holstein, *Traffic* 2002 3:614; Baluska et al., *J. Exp. Bot.* 2004 55:463; Samaj et al., *Plant Physiol.* 2004 135:1150).

Materials and Methods

Seed Sterilization

*Nicotiana tabacuum* cultivar petite havana seeds were sterilized using the chlorine gas method: seeds were placed in a 100 mm diameter open plastic petri dish in a dessicator (the petri dish lid was also placed in the dessicator). A beaker containing commercial bleach was placed in the same dessicator and 3.5 mL of 12 N HCl was added. The dessicator was closed. After 15 minutes of this treatment the steilized tobacco seeds were transferred in the closed petri dish under a laminar flow bench and leave to "aerate" (petri dish lid off) overnight. The petri dish was sealed with parafilm and the seeds stored at room temperature in the dark until further use.

Tobacco Culture

Autoclaved magenta boxes were filled with about 50 mL of still hot from autoclaving MS media supplemented with hormones and vitamins. After solidification of the media three sterilized tobacco seeds were placed on the media. The magenta box was closed and placed in Percival incubator #1 (settings for soybean). The leaves were ready to harvest after 4 to 6 weeks.

Bombardment

Solid MS media plates were prepared. Leaves were harvested and placed on the MS media (stem in the media) 2 hours prior to the shot. No osmotic treatment is required since this treatment may kill the leaf during the 48 hours after the shot. The gun parameters have been tested using pLMNC95 plasmid (35S-GFP) and fluorescent spots were observed in all the parameters tested.

Magnetic Infiltration

Since the PAMAM-IOMSN are magnetic, they were placed on plant tissue which was then placed on large magnets (4 large stir bars). Flat tobacco leaves were briefly dipped or not in K4-enzyme solution and then placed on a MS media Petri dish. The adaxiale face is in contact with the media. Ten micrograms of freshly sonicated PAMAM-IOMSN in sterile water were placed on the abaxiale face of the tobacco leaf. Immediately after, the adaxiale face was checked. No PAMAM- IOMSN could be detected using a 50× magnification. A plate was then placed on top of the magnet while the other remained on the bench. After 18 hours incubation in the dark, the adaxiale face was checked again for presence of PAMAM-IOMSN.

Tobacco Protocol and MSN Treatment for Endocytosis

Tobacco protoplasts are the starting material. Unlike bombardment, density is not an issue and regular MSN were used. Further, because iron oxide quenches fluorescence, no IOMSN could be used since the detection system uses epifluorescence.

Tobacco protoplasts extraction was done according to Spangenberg and Potrykus guidelines with small modifications. Briefly, after digestion protoplasts were washed in W5 medium (room temperature) and resuspended in 2 mL W5 medium. The resuspension was overlayed on a 2.3 M sucrose-K3 medium 5 mL layer in a 15 mL tube and centrifuged 10 minutes at 80 g in a swinging bucket centrifuge at room temperature. The protoplasts can be kept alive for several days at 4° C.

The MSN were resuspended in K3 medium and sonicated for 5 minutes before each experiment. Note that those MSN seemed not to aggregate as much as the PAMAM-IOMSN. For endocytosis treatment, the MSN were directly placed into the protoplast layer and left overnight. Before observation the tube was centrifuged to pellet cell debris and unincorporated MSN. Three types of MSN were used:

Type I: spherical MSN filled with fluorescein
Type II: spherical MSN filled with fluorescein (next generation)
Type III: spherical MSN filled with fluorescein and coated with PEG One and a half million cells were incubated with either 1.5 µg or 15 µg MSN.

Results

Figure 2:
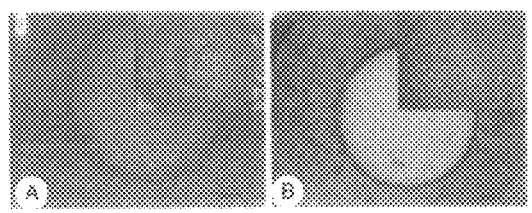
FIG. 2 illustrates loaded macrocarrier before and after the shot. (A) 0.6 μm gold particles coated with pLMNC95. (B) PAMAM-IOMSN coated with pLMNC95. The aggregates are present in the MSN case after a 1 minute sonication and before loading the macrocarrier.
Figure 3:
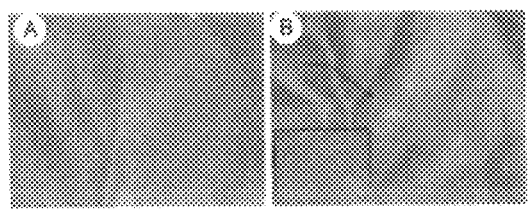
FIG. 3 illustrates tissue damage right after the shot. (A) 0.6 μm gold particles coated with pLMNC95. (B) PAMAM-IOMSN coated with pLMNC95. Patches of tissue damage are visible on the leaf.
Figure 4:
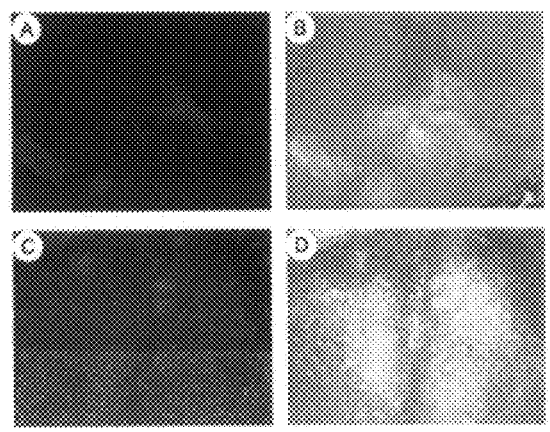
FIG. 4 illustrates tissue damage right after the shot 9 cm/900 psi. A-B) PAMAM-IOMSN coated with pLMNC95, 48 hours after the shot. C-D) 0.6 μm gold particles coated with pLMNC95 shot, 48 hours after the shot. Cell damage and autofluorescence were observed. Forcep induced wounds in C) and D) yield wide fluorescent patches.
Figure 6:
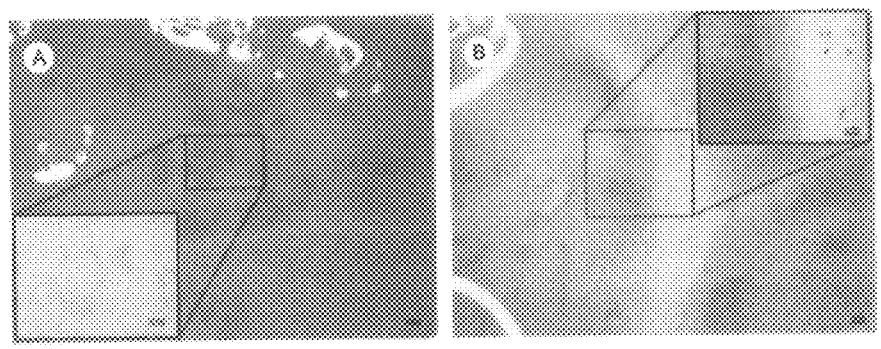
FIG. 6 illustrates GUS staining of tobacco leaf shot: A) 9 cm/900 psi; B) 9 cm/1100 psi. In both cases agglomerates are visible (especially in A). In B), tissue damage (browing) is visible on the impact spot. No GUS expression was seen on the 3 repetition per condition (12 in total) that were observed.

PAMAM-IOMSN coated with pLMNC95 (1/5 ratio) were treated as gold particles regarding the ethanol washes. Agglomeration of the particles in large clusters was noted (FIG. 2). Shooting with such agglomerates resulted systematically in plant tissue damage and death after 48 hours incubation (FIGS. 3 and 4). In order to reduce the tissue damage, gun parameters were varied. Three pressures were tried: 1100 psi, 900 psi and 650 psi, in combination with three distances (3, 6 and 9 cm). For the 3 cm distance, no mesh was used. One result (FIG. 5) showed some spots but mixed with a lot of wound-induced autofluorescence. Because of the wounding effect inducing autofluorescence, pTF102 (constitutive GUS expression) was used instead of pLMNC95. After 48 hours, leaves were stained for GUS activity (FIG. 6). When the same experiment was done using maize callus as a target, no GUS expression was observed (data not shown).

Across all these experiments, the impact of aggregates was minimized. When DNA is added to the PAMAM-IOMSN, it acts like a glue and bigger aggregates form. Sonication reduces aggregation, however, as soon as the sonication ends, the aggregates re-form rapidly. Even when loaded promptly after sonication, PAMAM-IOMSN (DNA coated or not) formed aggregates when ethanol evaporates. Thus, bombardment with the iron-oxide caps was pursued, e.g., with newer generation MSN.

Figure 7:
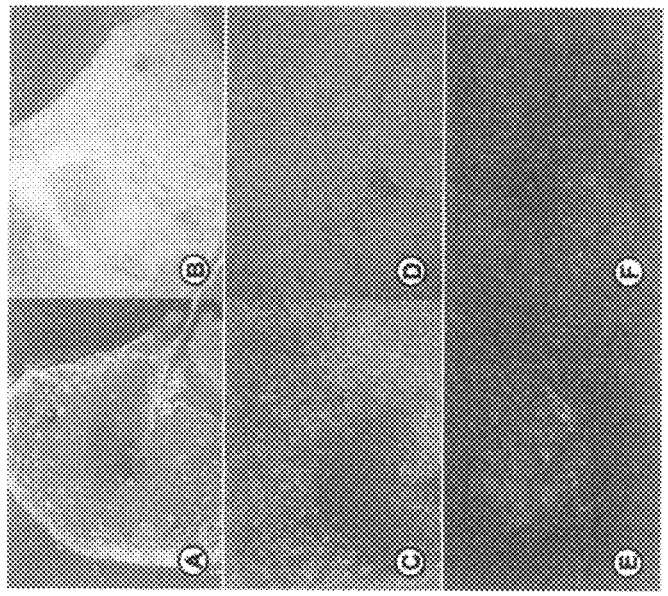
FIG. 7 illustrates tobacco leaf treated with K4-enzyme solution. A) and C) abaxiale face with PAMAM-IOMSN before experiment (X7 and X30, respectively). B) and D) corresponding adaxiale face before experiment (X7 and X30, respectively). E) and F) adaxiale face with PAMAM-IOMSN that penetrated through the leaf tissue (50×).

Using magnetic infiltration, some MSN were clearly visible on the adaxiale face of the enzyme-treated leaves indicating that the magnetic field was strong enough to pull the PAMAM-IOMSN through the leaf tissue (FIG. 7). The experiment was repeated with DNA coated PAMAM-IOMSN (using pTF102) and stained for GUS expression. Maize callus was also used in this experiment. No GUS activity was detected although PAMAM-IOMSN were still visible on the adaxial face of treated tobacco leaves.

As a control when improving the protoplast technique for endocytosis, PEG transformation was done as described in Spangenberg and Potrykus, using pLMNC95 (35S-GFP).

Figure 9:
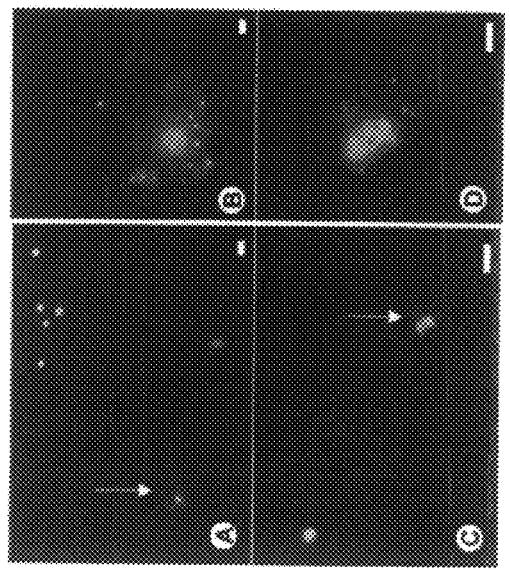
FIG. 9 illustrates epi-fluorescence imaging of tobacco protoplasts incubated with 15 μg of type I MSN. Overlay of DAPI and FITC pictures. The white bar represents 15 μm in A) and C), and 5 μm in B) and D). In both A) and C), a single cell presents fluorescent spots. B) and D) are details of respectively A) and C).
Figure 8:
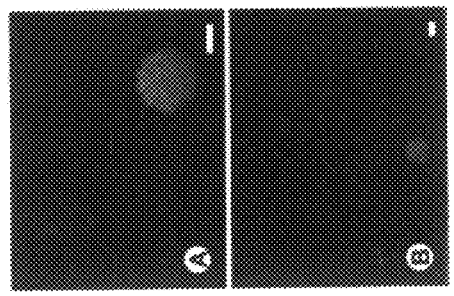
FIG. 8 illustrates epi-fluorescence of tobacco protoplasts transfected with pLMNC95 (35S-GFP). Overlay of DAPI and FITC pictures. The white bar represents 15 μM. In A) DAPI picture was taken in gray scale showing chloroplasts in green. In B) DAPI picture was taken in true colors which shows the chloroplasts in red.

Fluorescent tobacco cells were observed 24 hours after transfection. An example is shown FIG. 9.

Figure 10:
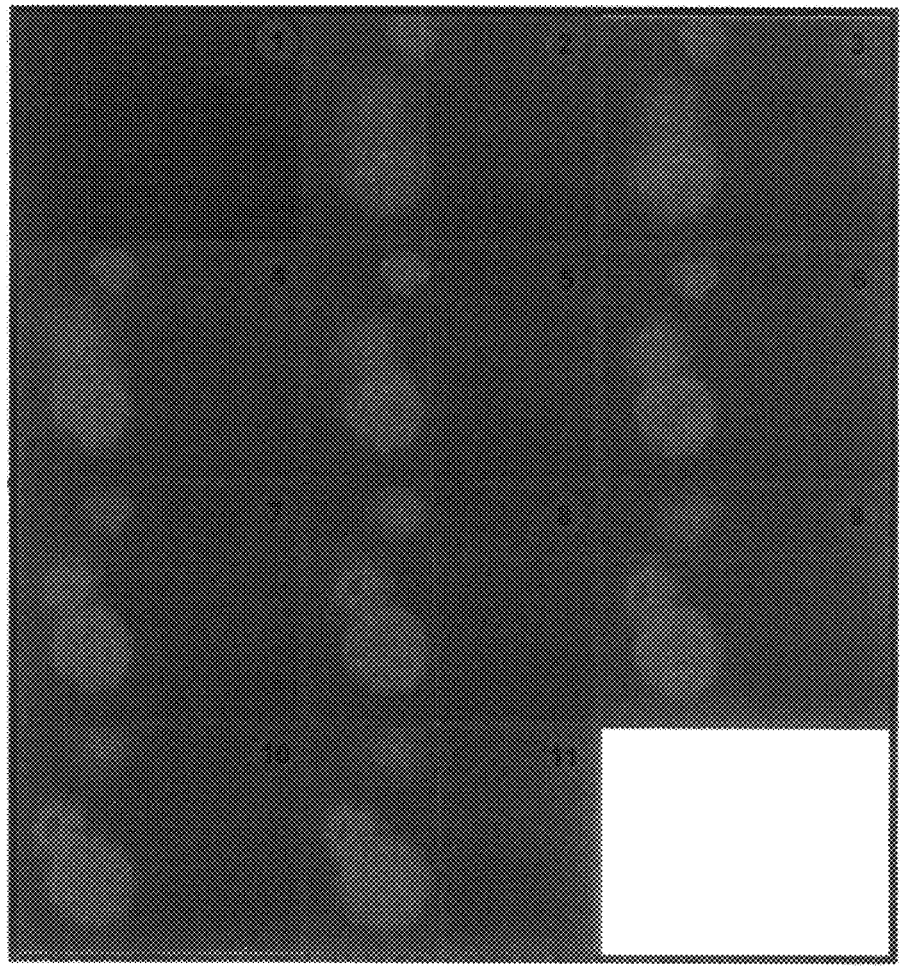
FIG. 10 illustrates detail of a Z-stack movie (With MSN.mov) showing a tobacco protoplasts incubated with 1.5 μg of MSN type III. FITC channel. Numerous fluorescent vesicles can be seen in different focal plans of the Z-stack in one protoplast demonstrating the presence of those vesicles inside the cell. Another smaller protoplast can be seen, although no fluorescent vesicle can be seen in it.

Using Type I MSN, very few cells (about 1%) showed fluorescent dots indicating endocytosis. Those dots were non-homogenous in size ranging from 2.5 to 0.4 µm in diameter. A regular MSN is 0.2 µm in diameter. This suggests that each dot represents several MSN at the same time. The use of epifluorescence microscopy did not distinguish whether the MSN were inside or outside of the cell membrane. In order to palliate the issue, a Z-stack movie was done in the FITC channel on treated protoplasts with Type III MSN (FIG. 10). The size of the fluorescent vesicles, likely containing the MSN, ranged from 0.3 µm to 1.3 µm.

Z-stack of treated and untreated cell are performed using apotome microscopy as well as confocal microscopy.

Example 9

Additional Plant Data

Slight modifications in protoplast production were implemented as follows. Tobacco leaves were sliced and digested overnight as described in Spangenberg and Potrykus. After digestion, the mixture is filtered through a sterile cheese cloth using a sterile plastic funnel into a series of sterile 15 mL culture tubes (10 mL per tube aliquoted using a tip-broken 10 mL sterile pipette with pipette-aid). In each tube, the green filtrate is overlaid with room temperature W5 solution (if W5 is cold the protoplast purification fails), and centrifuged for 10 minutes at 80 g in a swinging-bucket rotor at room temperature. The living protoplasts form a dark green layer at the interphase. A green pellet will be observed as well (cell debris). The cells were treated directly at the interphase ring stage of the protocol. After treatment, another centrifugation (80 g for 10 minutes) eliminated unincorporated MSN. The cells can be stored in a refrigerator at 4° C. as an interphase for several day. The cells need to be brought back to room temperature 4 hours prior to treatment.

All experiments described below were done using this protocol unless otherwise stated.

Magnetic Infiltration

PAMAM-IOMSN were incubated with tobacco protoplasts. After overnight incubation and centrifugation to remove extra PAMAM-IOMSN, a second cell layer was detected. A large stir bar was used as a magnet and applied to the side of the tube. Cells were dragged toward the magnet quickly. A sample of the "moving layer" was observed under microscope. Observation showed that PAMAM-IOMSN aggregates were adsorbed to the cells. Applying a magnetic force resulted in movement of the aggregate without detaching it from the cell, demonstrating a strong binding force.

Endocytosis

Fluid Phase Endocytosis

Using an endocytosis marker, the ability of the tobacco protoplast to perform endocytosis was ascertained. The marker was Lucifer Yellow CH, lithium salts (Invitrogen cat#L-453). Lucifer Yellow (LY) was resuspended in K3 medium at 5 mg/mL. Five microliters of LY solution were added to 1.10 protoplasts in 0.5 ml of K3 medium. The protoplasts were incubated 3 hours at room temperature (26° C.) and observed in confocal microscopy. Fluorescent vesicles forming inside the protoplast were clearly visible demonstrating the ability of tobacco protoplasts to perform endocytosis. See Wright and Oparka, *Planta* 1989, 179; Etxeberria et al., Plant Cell Physiol. 46. Interestingly, in several tobacco protoplast multivesicular structures were observable. This has been recently documented in BY2 cells as pre-vacuolar vesicles Tse et al., *Plant Cell* 2004, 16.

Sterilizing MSN (Works for all Types of MSN)

Sonicate the MSN solution for 30 seconds. Take 50 µg of MSN (about 15 µl) and pellet in a clean tube (5000 rpm for 20 seconds). Remove the supernatant and add 700 µl of 100% ethanol. Sonicate for 10 seconds. Pellet the MSN at 5000 rpm for 20 seconds. Repeat the ethanol wash and pelleting. Resuspend the MSN in 25 µl of freshly autoclaved water by sonicating 30 seconds.

Incubation with MSN

Two types of MSN were used for the following experiments: Type II and Type III. Incubation occurred overnight. The protoplast/MSN ratio was kept constant at $5 \times 10^5/10$ µg. It is an arbitrary ratio. Usually 1 g of fresh tobacco tissue yields 1 to $2 \times 10^6$ protoplasts. The MSN are kept in W5 at 1 mg/mL with 50 µg/mL spectinomycin at 4° C. They were sonicated for 5 minutes before the experiment unless treated with DNA (they are simply vortexed briefly).

When Type-II MSN are used (without PEG coating), no fluorescent vesicles were observed and protoplasts looked just like the untreated protoplasts. As proof that MSN were in the media with protoplasts, pictures were taken without centrifugation after incubation so that the unincorporated MSN were still visible with the protoplasts.

When Type-III MSN were used (with PEG), after overnight incubation, fluorescent vesicles were visible within the cells. Most of the time the vesicles were near the plasmalema, however, some "central clusters" were observed. In some cases the non-treated cells had small fluorescent vesicles, although those vesicles were fluorescent in every channel of the confocal. MSN vesicles fluoresce only in FITC and not in TRITC. Therefore, merging the two channels, green vesicles were visible (MSN) as well as yellow vesicles (unknown vesicles).

Transient Genetic Transformation Using PEG Coated MSN

After demonstrating that tobacco protoplasts could incorporate "naked" PEG-coated MSN, plasmid DNA was coated on the MSN. The coating procedure had been established for PAMAM-coated MSN (Example 10), therefore, a reassessment was necessary with the PEG-coated MSN. A DNA/MSN ratio of 1/8 (in µg) did not allow full binding whereas a 1/10 ratio did. A more refined analysis showed that 1/9 ratio was still not sufficient to bind all the DNA (data not shown). To assess if the DNA bound to PEG coated MSN was available for enzymes, a HindIII digestion was attempted. The digestion buffer allowed a small release of the DNA in the 1/10 ratio, but if the DNA was digested by HindIII on the MSN, it was not released.

The 1/10 ratio was used in subsequent experiments. It is to be noted that incubation with DNA induced formation of aggregates. After DNA binding, the MSN were vortexed for 5 seconds on high speed Vortex Genie 2. This process helped the aggregates to disappear to a certain extent giving a homogenous looking DNA/MSN solution. Protoplast treatment was done as previously described. Observation of the protoplast was done 18 hours to 20 hours after mixing the MSN with the protoplasts. GFP expression was detected in several protoplasts where MSN fluorescent vesicles were observed. Some vesicles containing MSN were in movement within the cell. This demonstrates the feasibility of transient transformation with PEG-coated MSN.

Suzuki et al., *Exp. Cell Res.* 1977, 105 showed that tobacco protoplasts were able to endocytose nanoparticles. The authors described the use of mannitol to enhance the endocytosis rate. Protoplasts do not survive in the mannitol media more than several hours and an overnight incubation killed the vast majority of them (data not shown).

Example 10

Further Plant Data

In addition to MSN coated with GUS encoding DNA, MSN were used to introduce the gfp gene fragment into plant protoplasts via endocytosis. The MSN characteristics were modified by using gold or superparamagnetic iron oxide nanoparticles as caps for the encapsulation of guest molecules. MSN coated with iron oxide (IOMSN) are not spherical but ovoid (Giri, S., Personal communication). The introduction of nanoparticles with high densities to the MSN allows for gene gun bombardment. A chemical may be encapsulated in the pores of MSN and introduced together with DNA to test for release of chemical in plant cells. For example, β-estridiol, a chemical that can induce gene expression under the control of the XVE transactivator system, may be employed (Zuo et al., *Plant J.* 2000, 24:265).

Bombardment

DNA coating on MSN Type-III

To 25 μl of sterile MSN, add 0.5 μg to 1 μg of DNA. Add 50 μl of $CaCl_2$ and maintain on a vortex set on 5 for 1 minute. Stop the vortex and add 20 μl of spermidine. Vortex at setting 5 for 10 minutes. Pellet the DNA coated MSN (5000 rpm for 30 seconds) and resuspend in 200 μl of cold 100% ethanol (by finger tapping the tube). Repeat pelleting and ethanol wash twice. Resuspend the final pellet in 100 μl of ethanol 100%. Maintain the tube closed on the vortex setting 5. Finger vortex before use.

Loading the Macrocarrier

Set the macrocarriers on their metal holders on the sterilized bench. Load the macrocarrier one at a time. Set the foam box with the liquid nitrogen and the racks with the liquid nitrogen level about 3 mm above the top of the rack. Take 10 μl of the still vortexing MSN mix and spread evenly in the center of the macrocarrier. Immediately place on the rack in the liquid nitrogen. Repeat applying the MSN mix for each macrocarrier. Place racks with the macrocarriers in the freeze drier. Set the freezer drier for 2 hours and 30 minutes.

Bombardment

Stop the freeze-drier and slowly let the air in. Bombardment parameters are 650 psi (1100 psi can be used if cut leaves are the target tissue), 10 cm target distance and 10 cm gap distance with a metallic mesh and 28 mm Hg vacuum. MSN at 100 μg/ml in water. To increase MSN density, they may be capped with gold nanoparticles.

Results

Visualization

To visualize MSN (filled with fluorescein) and GUS gene expression in bombarded maize immature embryos, 114 mg of fluorescein filled IOMSN were resuspended in 1.14 ml of ethanol (99%) and treated as gold particles. The IOMSN were separated into two batches, one complexed with pTF 102 and the other one not complexed with DNA. Bombardment was performed at 650 psi and 9 cm. All steps were done according to the maize immature embryo bombardment protocol.

Figure 11:
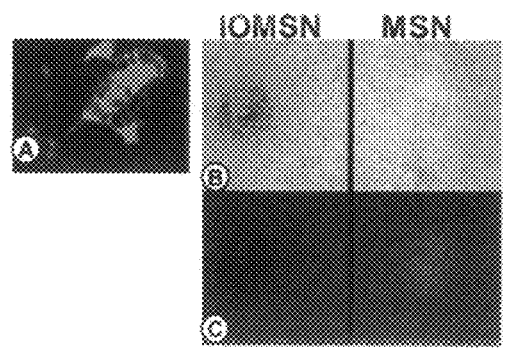
FIG. 11 illustrates visualization of fluorescein in MSN. A) Regular MSN filled with fluorescein were placed on agarose and visualized under UV light with GFP filter in the Olympus SH10. B) IOMSN compared to regular MSN in bright field (above) and under UV light with GFP filters (below). IOMSN, filled with fluorescein are not visible under UV light.
Figure 12:
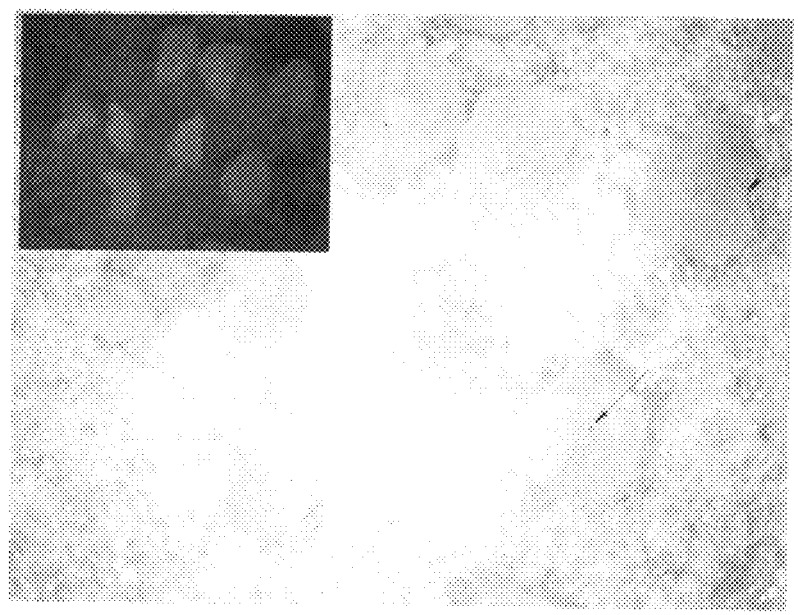
FIG. 12 illustrates IOMSN bombarded embryos. The small image shows the same as the large one but under UV illumination. Arrows show agglomerates of black IOMSN.
Figure 13:
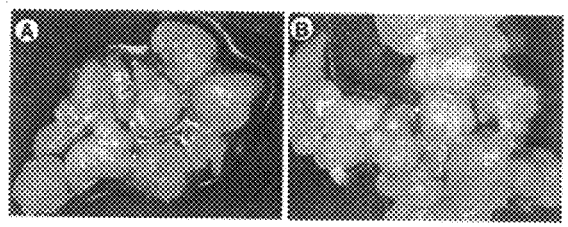
FIG. 13 illustrates histostaining or glucuronidase activity. A) Embryos bombarded with pTF102 coated IOMSN. B) Embryos bombarded with IOMSN alone.
Figure 4A:
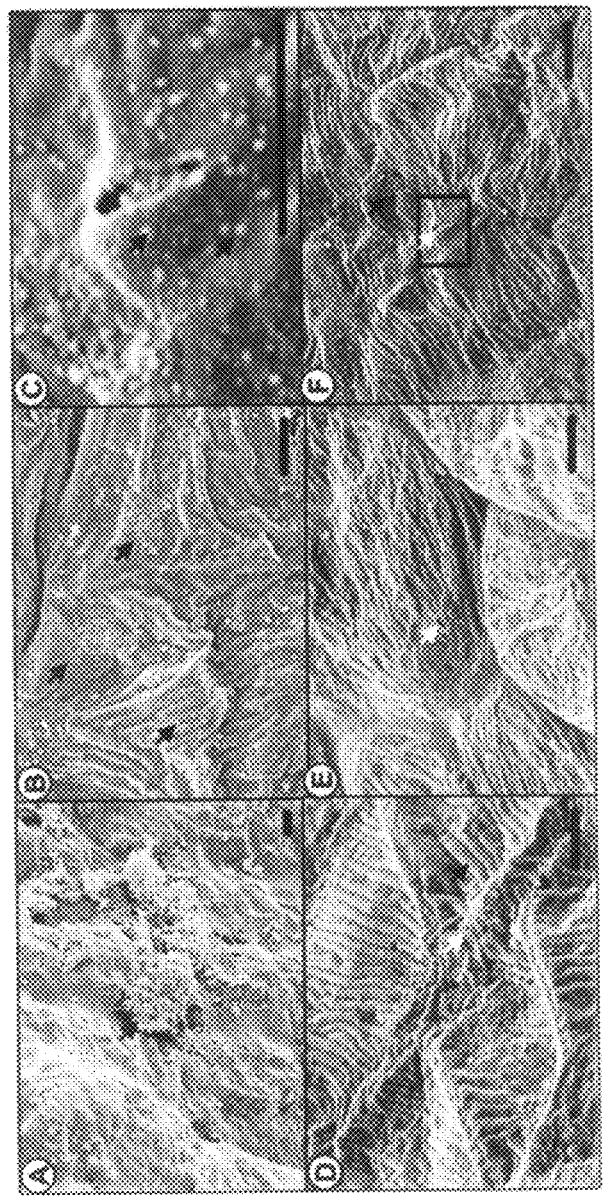

It was determined whether fluorescein could be visualized with the Olympus SH10 stereoscope in the lab under UV illumination (FIG. 11). The IOMSN were not compatible with fluorescein detection. One explanation is that the iron oxide coated on the MSN acts like a shield to the exciting light or to the fluorescence emits by fluorescein if it receives light. Another explanation is that the iron oxide works as a quencher for fluorescence. The embryos were observed under UV illumination after bombardment and no fluorescence observed (FIG. 12). The first possibility is that the IOMSN, although denser than regular MSN, are still not dense enough to be used as microprojectiles. However, observation of the macrocarrier after bombardment showed that no IOMSN remained adsorbed in the macrocarrier surface after the bombardment contrarily to what has been observed with regular MSN. To confirm that IOMSN actually reached the target tissue, the bombarded embryos were observed with a stereoscope (FIG. 12). Large patches of IOMSN could be detected on some embryos. The IOMSN tend to agglomerate when loaded on the macrocarrier and those agglomerates reached the immature embryos. This could be observed both in the DNA coated IOMSN experiment and in the naked IOMSN experiment (data not shown). Some bombarded embryos were sampled and fixed in FAA overnight. The remaining embryos were tested for GUS activity (FIG. 13). No GUS activity was detected showing that, either the MSN did not penetrate the cell or that they penetrated and for some reason gene expression was inhibited. To check if the IOMSN penetrated the cells, the embryos fixed in FAA were desiccated by successive ethanol baths and prepared for scanning electron microscopy. The analysis of the embryo's surface showed that the IOMSN rarely penetrated the embryo scutellar cells (FIG. 14). Some holes could be observed in the cell surface likely corresponding to the penetration of IOMSN. However, the vast majority of the IOMSN were present on the surface of the cells, confirming that they left the macrocarrier and reached the target tissue but did not penetrate the cells. The cell wall seems to be a strong barrier for the IOMSN to penetrate.

MSN/DNA Complexation Parameters

To optimize parameters for coating the DNA onto the IOMSN, the surface charge of the MSN was considered as a parameter for proper coating of the DNA. PAMAM-coated MSN were incubated in a physiological buffer (the buffer composition was not indicated) and various DNA/MSN ratios were tested. In these experiments, the MSN were used to transform animal cells by enocytosis.

Figure 15:
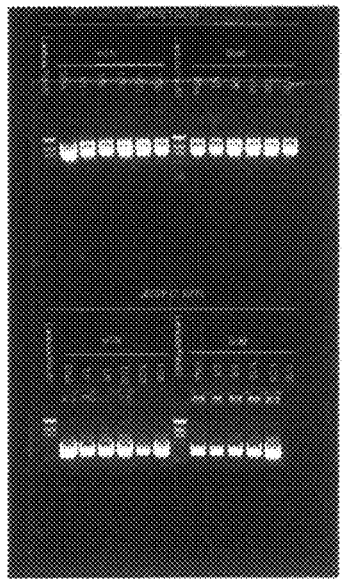
FIG. 15 illustrates DNA/IOMSN and DNA/gold complexation. Two plasmids were used for the experiment: pTF102 (top part of the gel) and pEGFP-C1 (lower part of the gel). Different ratios (μg DNA/μg of particle) were tested. No DNA was coated on either gold or MSN.
Figure 16:
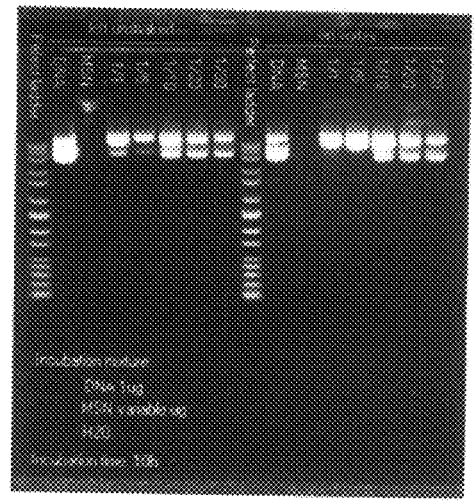
FIG. 16 illustrates effect of permanent vortexing on DNA/IOMSN coating.

The first experiment was done using both IOMSN and gold particles (0.6 μm) in PBS buffer. Several DNA/MSN and DNA/gold ratios were tested. Briefly, the DNA was put with the particles to coat in 20 μL PBS buffer and incubated at room temperature for 10 hours. After incubation loading buffer was added (2 μL) and the sample was loaded in a 1% agarose gel (FIG. 15). In these conditions, no DNA was coated on either type of particles. It is to be noted that the quantities of gold used in this experiment were more than a thousand times smaller than the one used during bombardment experiments. No $CaCl_2$ and no spermidine were added. Both MSN and gold particles tend to sediment in the tube quite rapidly and therefore are not in contact with the DNA during the coating incubation time. For this reason, the experiment was repeated, without the gold particles this time, but half of the MSN/DNA samples were constantly vortex during the incubation time. A gel assay, as described above, was performed (FIG. 16). Curiously, the 1/1 and 1/5 ratios, especially on the vortexed samples seems to lose the supercoiled version of pTF 102.1. No improvement of the coating was observed with vortexing the sample.

Figure 17:
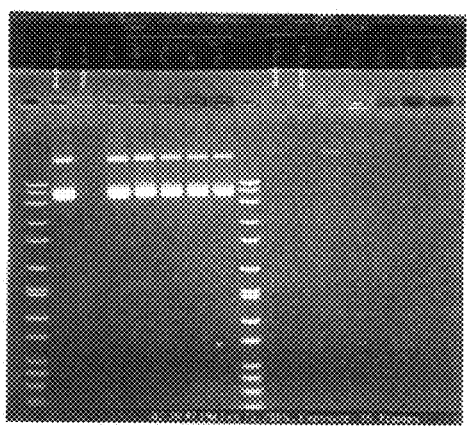
FIG. 17 illustrates effect of 80 mM $CaCl_2$ on DNA/IOMSN coating. The same amount of DNA was used in each sample and the entire sol sample was loaded in the gel.

The effect of $CaCl_2$ (80 mM final as in bombardment protocol) on the coating was tested next. The $CaCl_2$ in the sample prevented migration of the DNA in the gel and the control DNA incubated with $CaCl_2$ and without IOMSN was very weak on the gel suggesting that the DNA precipitates on the tube walls also during the coating. A non $CaCl_2$ treated control (water instead of $CaCl_2$) was added and the experiment repeated (FIG. 17). It is clear that $CaCl_2$ induces great loss of DNA, probably due to the coating of the tube walls. To avoid migration problems due to $CaCl_2$, the gel was left at 15 V for 3 hours and then the voltage was set to 100V. The non treated samples showed no coating and interestingly, the supercoiled plasmid is now present in the 1/2 ratio suggesting that what was observed in FIG. 16 was an artifact. The treated samples showed very few amounts of DNA in the non-IOMSN control and in the 1/4 and 1/10 ratios.

Figure 18:
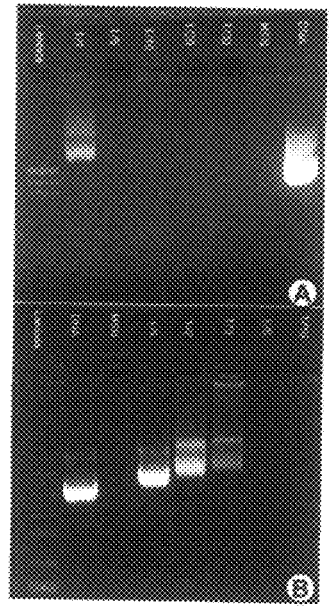
FIG. 18 illustrates DNA/PAMAM-IOMSN complexation. Ratios are indicated in μg. A) First attempt DNA/MSN ratios from 1/1 to 1/30. B) Second attempt with ratios from 1/1 to 1/10. In both cases a DNA alone (DNA) and PAMAM-IOMSN alone MSN) control was loaded.
Figure 44:
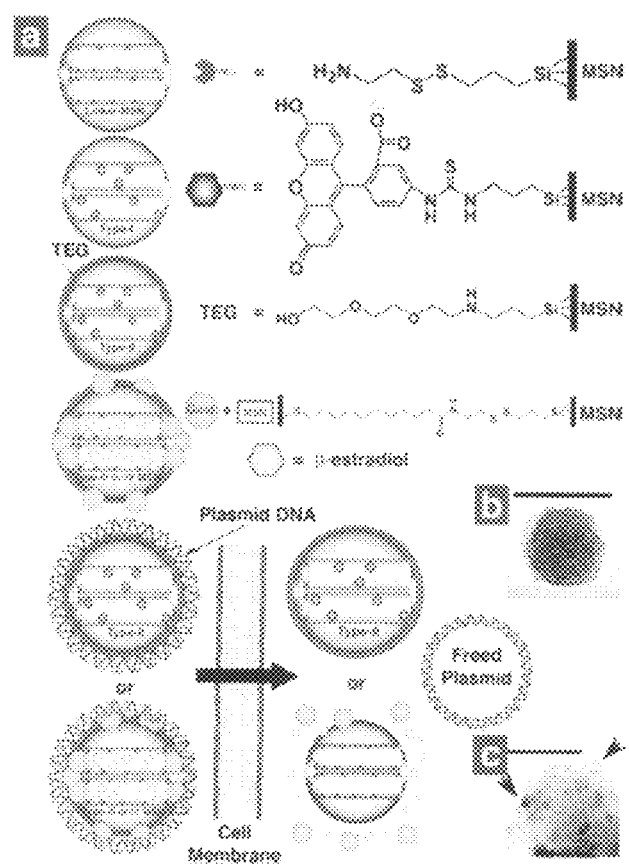

One possibility was to modify the surface of the IOMSN so that electrostatic binding of DNA becomes naturally possible. It was decided to explore the possibility of DNA coating on PAMAM coated IOMSN. Several ratios of PAMAM-IOMSN/DNA were incubated in 20 µL of autoclaved water. The incubation product was loaded on a 1% agarose gel (FIG. 18). The incubation was performed in 20 µL of autoclaved pure water during 6 hours at 4° C. Loading buffer (5 µL) was added and the sample was load on a 1% agarose gel with ethidium bromide in the gel. The DNA is entirely retained by the PAMAM-IOMSN at a 1/5 ratio (FIGS. 18A and B). Interestingly, the DNA complexed with PAMAM-IOMSN remains nonfluorescent in the wells.

The IOMSN appears to quench any fluorescence. When lower ratios were studied (1/1, 1/2 and 1/3, FIG. 18B), the unbound DNA migrated more slowly than the free DNA in the control. This could indicate that the DNA is originally bound to MSN but the PAMAM-IOMSN are too few to retain it against the electrical current in the gel. The more PAMAM-IOMSN, the more the DNA was retained until, at 1/5 ratio, the entire microgram of DNA was retained in the well.

Example 11

The unique structural features, such as chemically and thermally stable mesoporous structures, large surface areas (>800 m²/g), tunable pore sizes (2 to 10 nm in diameter), and well-defined surface properties of organically functionalized MSNs have made them ideal for hosting guest molecules with various sizes, shapes, and functionalities. In many non-porous particle-based delivery systems for plant cells and tissues, the molecules of interest are limited to nucleic acids which are usually adsorbed on the exterior particle surface of the carriers. For example, the widely used "gene gun" system employs DNA-coated gold microparticles as bullets for bombardment of plant cells and tissues to achieve gene transfer in these cell-wall-containing organisms. While such systems are suitable for many applications, it is currently difficult to co-deliver anything other than nucleic acids. Microinjection is a method that can be used for delivery of multiple biogenic species including DNA. However, this method is not suitable for plant transformation due to its limitation in targeting materials, and extremely low efficiency (Potrykus, *BioTech.* 1990, 8:535).

In the case of the MSN system, drugs or other agents may be loaded in the mesopores and encapsulated with covalently bound caps that physically block the agents from leaching out. Molecules entrapped inside the pores are released by the introduction of uncapping triggers (chemicals that cleave the bonds attaching the caps to the MSN). The feasibility of this design was demonstrated by using a disulfide-reducing anti-oxidant, dithiothreitol (DTT), as the gate-opening trigger to release biogenic molecules inside mammalian cells (Lai et al., *J. Am. Chem. Soc.* 2003, 125:4451).

Methods

Mesoporous Silica Nanoparticles

Fluorescein-doped MSN with approximate diameters of 100 to 200 nm (FITC MSN, Type-I MSN) were synthesized as described in Slowing et al. (*J. Am. Chem. Soc.* 2006, 128:14792). For the synthesis of Type-II MSN, the surface of Type-I MSN was modified by covalently attaching an organic ligand, triethylene glycol (TEG). The synthesis of the TEG ligand was achieved via a modified procedure based on Brust et al. (*J. Chem. Soc. Chem. Comm.* 1995, 1655). Specifically, 1-[2-(2-bromoethoxy)-ethoxy]-2-methoxy-ethane was synthesized by following the procedure in Zheng et al. (*J. Am. Chem. Soc.* 2000, 125:7790). The isolated molecule was then attached to 3-aminopropyl-trimethoxysilane by refluxing in ethanol overnight. The crude product was directly grafted to the as-synthesized FITC-MSN (still containing surfactant template). Once grafted, the surfactant template was removed as described in Huo et al. (*J. Am. Chem. Soc.* 2006, 128:6497).

To construct the DNA delivery systems, linker-MSN material (MSN with amine terminal organic linkers reducible by DTT) with an average pore size of about 2.3 nm was synthesized as described in Lai et al. (*J. Am. Chem. Soc.* 2003, 125:4451). To load the analytes (fluorescein or β-estradiol), the linker-MSN (100 mg) was suspended in a buffer or buffer/organic solution of the chosen analyte ($2.6 \times 10^{-4}$ M fluorescein or $5.0 \times 10^{-2}$ M β-estradiol) and stirred at room temperature for 24 hours. Acid functional gold nanoparticles were synthesized by modifying the method described by Brust et al. (1995). Specifically, the organic thiol ligand p-mercaptophenol was substituted with 11-mercaptoundecanoic acid. For capping, these acid-gold-nanoparticles were suspended in the same analyte solutions and along with amide coupling agent (80 mg) that was stirred at room temperature with the linker-MSN for 24 hours. Following centrifugation and washings, gold-capped fluorescein or β-estradiol loaded MSN were isolated. The amount of fluorescein loaded (22 µmoles/g) was calculated by measuring the difference in the initial loading solution and the fluorescein that was physisorbed and was removed by the washings.

Plant Material

Protoplasts were isolated from 6- to 8-week old tobacco plants (*Nicotiana tabacum* cv Petite Havana) aseptically grown on Murashige and Skoog media without plant growth hormones (MS) according to Spangenberg et al., In: *Gene Transfer to Plants*, pp. 58-65 (1995). For tobacco plantlets bombardment experiments, twenty-five surface-sterilized seeds were arranged per plate (5 mm apart) in the center of a 100×25 mm Petri dish containing MS media and germinated aseptically for 14 days (23° C., 18 hours light). For culture conditions of transgenic plants used in controlled release experiments, surface sterilized seeds of each transgenic event were germinated on Y segmented Petri dishes. Each third of a segmented Petri dish contained a different media: (1) MS media; (2) MS+1 mM DTT; and (3) MS+50 µM β-estradiol. In the plate center part of each third, 10 seeds were placed in each segment (30 seeds per plate) and allowed for germination for 14 days. Maize immature zygotic embryos were isolated from genotype Hi II ears 12 days after pollination (Frame et al., *In vitro Cell Devel. Biol. Plant* 2001, 36:21).

Endocytosis Experiments

Tobacco protoplasts were mixed with MSN in W5 media (Spangenberg et al., supra) using $10^6$ cells for 10 µg of MSN. The mix was incubated overnight in 3 mL of W5 in BD Falcon 6-well flat-bottom plates. To remove non-engulfed MSN (except for FIG. 20A), the mixture were overlaid on K4 medium (Spangenberg et al., supra) and centrifuge at 100×g for 10 minutes at room temperature. The protoplasts at the interphase were collected and evaluated.

DNA/MSN Coating and Bombardment

To coat DNA onto Type-II MSN for endocytosis experiments, 1 µg of purified plasmid DNA was incubated with 10

µg MSN in 50 µL water for 2 hours at 23° C. The MSN were washed three times with W5 media prior to incubation with protoplasts.

Bio-Rad Biolistic PDS-1000/He particle delivery system was used for MSN delivery into plant cells. To coat DNA onto gold-capped MSN, the standard protocol for coating gold particles for the biolistic gun (Sanford et al., *Methods Enzym.* 1993, 217:483) was used with modifications. To prevent the agglomerate formation, a quick freeze/drying method of the gun macrocarrier was developed. Once DNA/MSN mixture was in ethanol, the tube was vortex constantly. Immediately after the DNA/MSN was loaded onto the macrocarrier, it was immerged into liquid nitrogen. The frozen macrocarriers were then freeze-dried using a Labconco Freezone 2.5 for 2 hours before being used for bombardment. The bombardment parameters for the tobacco plantlets were 650 psi rupture disk, 10 cm gap distance, and 10 cm target distance. A sterile 150 µm mesh was used between the macrocarrier and the target tissue. Bombardment of maize immature embryos performed using the procedure in Frame et al., supra. After bombardment, the embryos were placed on N6-30 medium without selection for 10 days to avoid callus auto fluorescence to interfere with the GFP expression evaluation.

In Planta Controlled Released

Plants were germinated and grown in Y-segmented Petri dishes as described herein. For each transgenic event, nine Petri dishes with a total of 270 plantlets (90 plants per media treatment) were used. Plants were grown for 48 hours after bombardment before being subjected to evaluation. Fluorescent foci were viewed under an Olympus dissecting scope.

Synthesis of Acid Functionalized Gold Nanoparticles

Acid functionalized gold nanoparticles (Acid-Au-NPs) were synthesized via a modification of the procedure by Brust et al. (1995). In a typical experiment, hydrogen tetrachloroaurate (III) hydrate (300 mg, $7.63 \times 10^{-4}$ mol) was dissolved in 15 mL methanol, followed by the quick addition of 11-mercaptoundecanoic acid (393 mg, $1.8 \times 10^{-3}$ mol) and glacial acetic acid (3.0 mL). While under vigorous stirring, an aqueous solution of sodium borohydride (30 mL, 0.4 M) was added in small portions. Washing with methanol, ethyl ether, and water yielded the desired 10-15 nm Acid-Au-nanoparticles.

Preparation of Type IV MSN

Type IV MSN were prepared by submerging the uncapped MSN particles in an aqueous solution of β-estradiol (50 mM). The mechanism of loading is a simple equilibrium. The β-estradiol was allowed to freely diffuse in and out of the pores of the MSN until capping occurs. When capping occurs, all the molecules of β-estradiol that are in the pores were trapped in the pores. This equilibrium of β-estradiol movement in solution was the same for all MSN particles because of the monodispersity in the pore size, surface area, and particle size, as demonstrated in Lai et al., supra.

Analysis of Transgenic Plants

Transient GFP evaluation was performed 24-48 hours after bombardment. Southern blot analysis of pER8-GFP tobacco plants was performed as described in Sambrook and Russell in *Molecular Cloning* (2001). Ten micrograms of genomic DNA for each plant were digested with restriction enzyme XhoI. The digestion products were separated on a 1% agarose gel and transferred on a Bior-Rad Zeta-probe membrane using standard procedure (Sambrook and Russell, 2001). A probe fragment corresponding to pER8-GFP GFP coding sequence was prepared by PCR and $^{32}$P-labeled using Stratagene Prime it II random primer kit following the manufacturer's instructions.

Microscopy and Image Analysis

Isolated live cells experiments images were taken using a 63× oil objective with a Leica TCS/NT laser scanning confocal microscope equipped with Argon 488 nm and Krypton 568 nm lasers plus a double dichroic DD488/568 filter. To detect fluorescence in the green channel, a combination of RSP580 and BP525/25 filters was used under wavelength between 500 and 550 nm. For the red channel, wavelength above 590 nm was selected using a LP590 filter. During scanning, pinhole was maintained at 1 for all images. Images were acquired using TCS software and analyzed using ImageJ (Abramoff et al., *Biophotonics Int'l* 2004, 11:36). Whole tissue images were taken under either bright field or GFP band pass exciter 460-490 nm with emission filter 510-550 nm using an Olympus SHZ10 stereoscope coupled to a SPOT RT color CCD camera (Diagnostic Instrument Inc.). Images were acquired with SPOT software.

For transmission electron microscopy measurements, a small aliquot was sonicated in nanopure water for 20 minutes. A single drop of this suspension was placed on a lacey carbon coated copper TEM grid and dried in air. The TEM examination was completed on a Philips model CM-30 operated at 300 kV at 69,000 to 340,000 electron optical magnification.

Results

Figure 20:
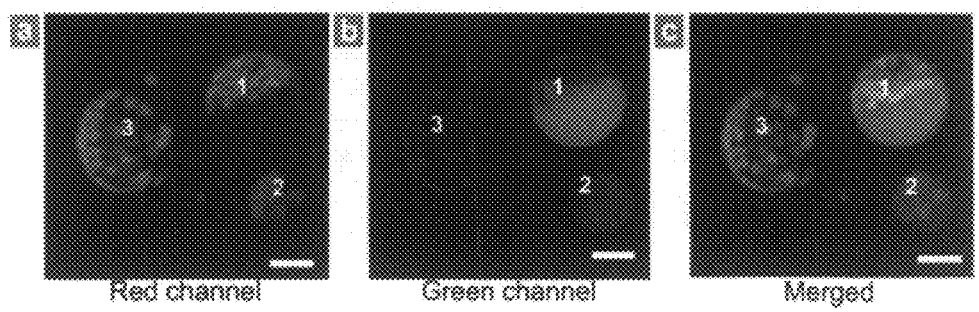
FIG. 20 shows tobacco mesophyllprotoplast endocytosis using Lucifer Yellow CH. (a-c) 3-D reconstitution of confocal images of cells displaying high (1), medium (2) and none (3) level of intracellular Lucifer Yellow CH (LYCH). (d) Summary of frequency of LYCH (level 1 and 2) cells in 5 independent endocytosis experiments. Cells were counted after overnight incubation of protoplasts in W5 media containing 1 mM LYCH. Cells were washed three times before counting.
Figure 21:
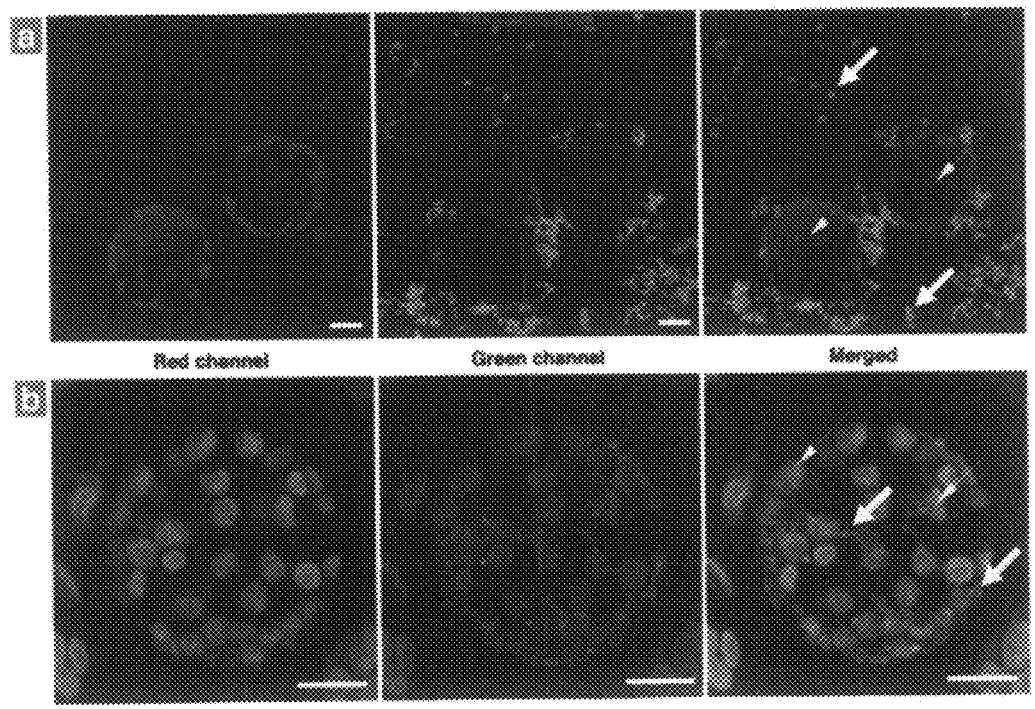
FIG. 21 illustrates confocal imaging of MSN treated tobacco mesophyll protoplasts. Tobacco protoplasts were incubated overnight in W5 medium with Type-I MSN (A, single focal plane images), and Type-II MSN (B, 3D reconstitution images). MSN of both types were functionalized with fluorescein and thus visible in green (thick arrows). Auto-fluorescent chloroplasts in protoplasts are indicated by thin arrows. (bar: 10 μm).

To investigate how the capped MSN system interacts with various plant cells, a series of MSNs with different surface functional groups/caps was synthesized. The use of MSN on protoplasts (plant cells with the cell wall removed) that are often used as model systems in physiological and cellular process studies (Sheen, *Plant Physiol.* 2001, 127:1466) was investigated. Compared to animal systems, plant cell endocytosis is less understood and the tools for studying the mechanisms are limited to membrane impermeable dyes (Samaj, In: *Plant Endocytosis*, Springer, pp. 1-17 (2001)). In the present experimental conditions, 26±7% of tobacco mesophyll protoplasts underwent endocytosis using Lucifer Yellow dye (FIG. 20). Protoplasts incubated with Type-I MSN did not uptake the nanoparticles (FIG. 21A), however, under the same condition, Type-II MSN (i.e., Type-I MSN functionalized with triethylene glycol, TEG) was successfully internalized (FIG. 21B). Type-II MSN remained in endocytotic vesicles in the cytoplasm for the entire duration of the experiment (72 hours). Seven percent (+3%) of the cells examined engulfed Type-II MSN. This demonstrates that surface properties of the particles play a role in plant cell endocytosis. Compared to animal cells, where endocytosis is an efficient process, the amount of MSN per plant cell appeared low. The size of the endocytotic vesicles ranged between 0.2 to 3 µm in diameter, which represents 1 to 15 MSN. The number of vesicles per cell was highly variable ranging from 1 to >20. Because no toxicity to plant cells was observed (FIG. 58), MSN can serve as a new and versatile tool for both plant endocytosis and cell biology studies.

Figure 25:
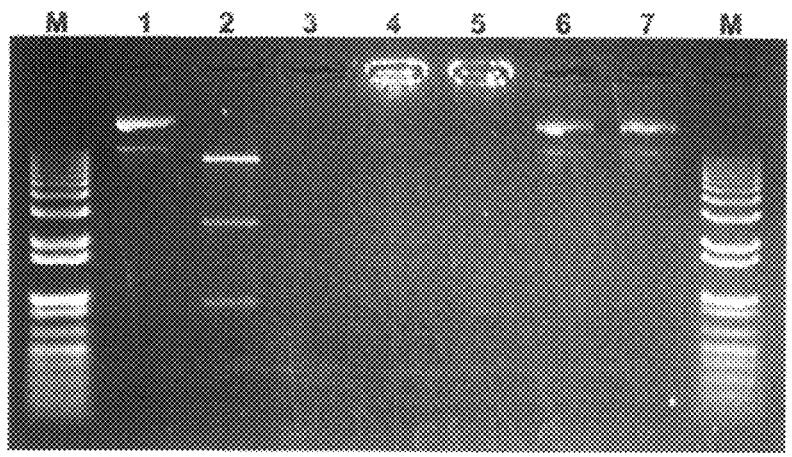
FIG. 25 shows a restriction enzyme digestion of pER8-GFP plasmid DNA coated on Type II MSN. One microgram of pER8-GFP plasmid DNA was incubated with 10 mg of Type II MSN in water for 2 hours at 23° C. To demonstrate that DNA bound to MSN is resistant to restriction enzyme digestion, half of the DNNMSN mixture was incubated with 5 units of Hind III in 1× Promega (Madison, Wis.) buffer E, the other half of mixture was incubated in 1× Promega buffer E only as control. After 2 hours incubation at 37° C., the digestion reaction and control incubation were terminated by heat treatment at 65° C. for 30 minutes. To release MSN bound DNA, these samples were treated with 5 M NaCl at room temperature for 1 hour. Subsequently, the samples were centrifuged and the supernatant was dialyzed against 10 mM EDTA to remove salt and reduce the volume. DNA quantity from all samples where measured using NanoDropB ND-1000 spectrophotometer. An equal amount of DNA from each treatment sample was loaded on a 1% agarose gel containing 100 mg/L ethidium bromide for DNA visualization. The data clearly indicate that DNA bound to MSN is resistant to restriction enzyme digestion (compare Lane 7 with Lane 1). M: 1 Kb molecular marker. Lane 1: Undigested plasmid DNA. Lane 2: Plasmid DNA digested with HindIII. Lane 3: Type II MSN. Lane 4: DNA/Type II MSN. Lane 5: DNA/Type II MSN after HindIII digestion. Lane 6: DNA/Type II MSN treated with 5 M NaCl/dialysis. Lane 7: DNA/Type II MSN after HindIII digestion and 5 M NaCl/dialysis treatment.
Figure 26:
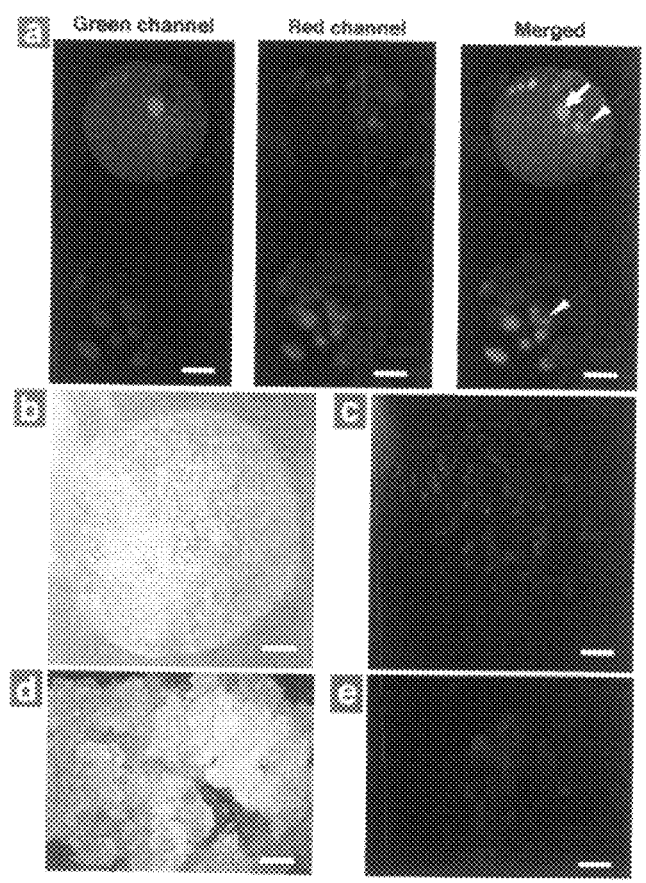
FIG. 26 shows a transgene expression in MSN transformed plant cells. (A) 3D reconstruction of two protoplasts, one (top cell) with endocytosed MSN (thick arrow) and expressing GFP, and one (bottom cell) without endocytosed MSN. Chloroplasts auto-fluorescent are in red and indicated by thin arrows (bar: 10 μm). Tobacco leaf bombarded with DNA-coated Type-III MSN in bright field (B) and UV light/GFP filter (C) (bar: 0.2 mm). Callus developing from immature maize embryos bombarded with DNA-coated Type-III MSN under bright field (D) and UV light/GFP filter (E) (bar: 1 mm).

To prove that MSN can function as a DNA delivery agent for plant cells, a plasmid containing a Green Fluorescent Protein (GFP) gene under the control of a constitutive CaMV 35S promoter (FIG. 23) was used. The optimal coating ratio for DNA/Type-II MSN was 1/10 (w/w). Under this ratio, or less, DNA formed a stable complex with Type-II MSN because no free DNA was observed in solution after 2 hours of incubation (FIG. 24). Type-II MSN-bound DNA endured restriction enzyme digestion (FIG. 25). Transient GFP expression could be observed 36 hours after protoplasts were incubated with DNA-coated Type-II MSN (FIG. 62A). In all GFP-expressing cells examined (about 7% endocytosis frequency), Type-II MSN could also be detected inside the cells (FIG. 26A). Standard polyethylene glycol (PEG)-mediated protoplast transformation can achieve 40-90% transient transformation efficiency when using 1-2 mg of DNA per $10^6$ cells (Sheen; http://genetics.mgh.harvard.edu/sheenweb/ (2002)). Here, transient transformation of 7% of the cells could be achieved when $10^6$ cells were incubated with 1000× less DNA, i.e., 1 µg DNA (coated on 10 µg Type-II MSN). The present results indicate that the DNA-coated Type-II MSN can serve as an efficient delivery system for protoplasts.

Because intact plant tissues are desired targets for plant genetic engineering, it was tested whether MSN could be introduced into plant via the gene gun system. Attempts of bombarding Type-I and Type-II MSNs did not lead to any successful transformation and no MSN was observed inside the cells, possibly because of the low density of these silica-based particles. To overcome this problem, a Type-DI MSN was synthesized, where the mesopores are capped by surface-functionalized gold nanoparticles (FIGS. 26A and C). In this system, the solid gold nanoparticles (10 to about 15 nm in size) not only serve as a biocompatible capping agent (Shukla et al., *Langmuir* 2005, 21:10644), but also add weight to each individual MSN to increase the density of the resulting complex material. GFP-expressing foci can be visualized on tobacco cotyledons bombarded with DNA-coated Type-III MSN (FIGS. 26A and C). On average 32±11 GFP fluorescent foci were visible per bombarded cotyledon. The use of commercially available 0.6 µM gold particles produced an average of 73±24 GFP expressing foci per cotyledon. These results show that the gold nanoparticle-capped MSN can be used for delivering DNA into intact plant cells and tissues by using the gene gun system. Furthermore, in comparison with the gold particle-based DNA delivery systems, where the DNAs are coated on the surface of solid gold particles, the mesoporous structure of MSN (surface area about 900 m²/g) (Lai et al., *J. Am. Chem. Soc.* 2003, 125:4451) offers the possibility of loading a large quantity of biogenic chemicals, including chemicals that are membrane impermeable or incompatible with cell growth media, inside the pores and delivering them along with DNA to the targeted cells.

DNA-coated Type-III MSN were also used to bombard maize immature embryos. GFP-expressing callus sectors from proliferating callus culture grown on non-selective medium were visible 10 days after the bombardment (FIGS. 26D and E). While the gold nanoparticles may be aggregated on the surface of MSN, the results suggested that the DNA could still form stable electrostatic complexes on the surface of Type-III MSN. Thus, this gene transfer system can be used to generate both transient and stable transgenic plant materials.

One of the most advantageous features of MSN is the potential to deliver different biogenic species simultaneously to the target sites and release the encapsulated chemicals in a controlled fashion. To test whether the controlled release that was successful for animal cells (Radu et al., *Proc. Natl. Acad. Sci. USA* 2004, 126:13216; Huang et al., *FASEB J.* 2005, 19:2014; Slaving et al., *J. Am. Chem. Soc.* 2006, 128:14792) could also be applicable to plant cells, transgenic tobacco plants containing an inducible promoter controlled expression gfp gene were prepared (FIG. 23). Two transgenic events were chosen: one with low (event B) and one with higher (event G) integration pattern complexity (FIGS. 27A-D). The expression of GFP in plants can only be observed when the chemical inducer β-estradiol is present (Zeno et al., *Plant J.* 2000, 24:265). Fourteen-day old transgenic tobacco plantlets were bombarded with Type-IV MSN, which were filled with equal amounts of β-estradiol and their pores capped with gold nanoparticles via the aforementioned disulfide chemical linker (Lai et al., *J. Am. Chem. Soc.* 2003, 125:4451). The release of β-estradiol is triggered by DTT, which is a commonly used chemical in the media for enhancing plant transformation frequency (Olhoff et al., *Plant Cell Rep.* 2001, 20:731).

Figure 27:
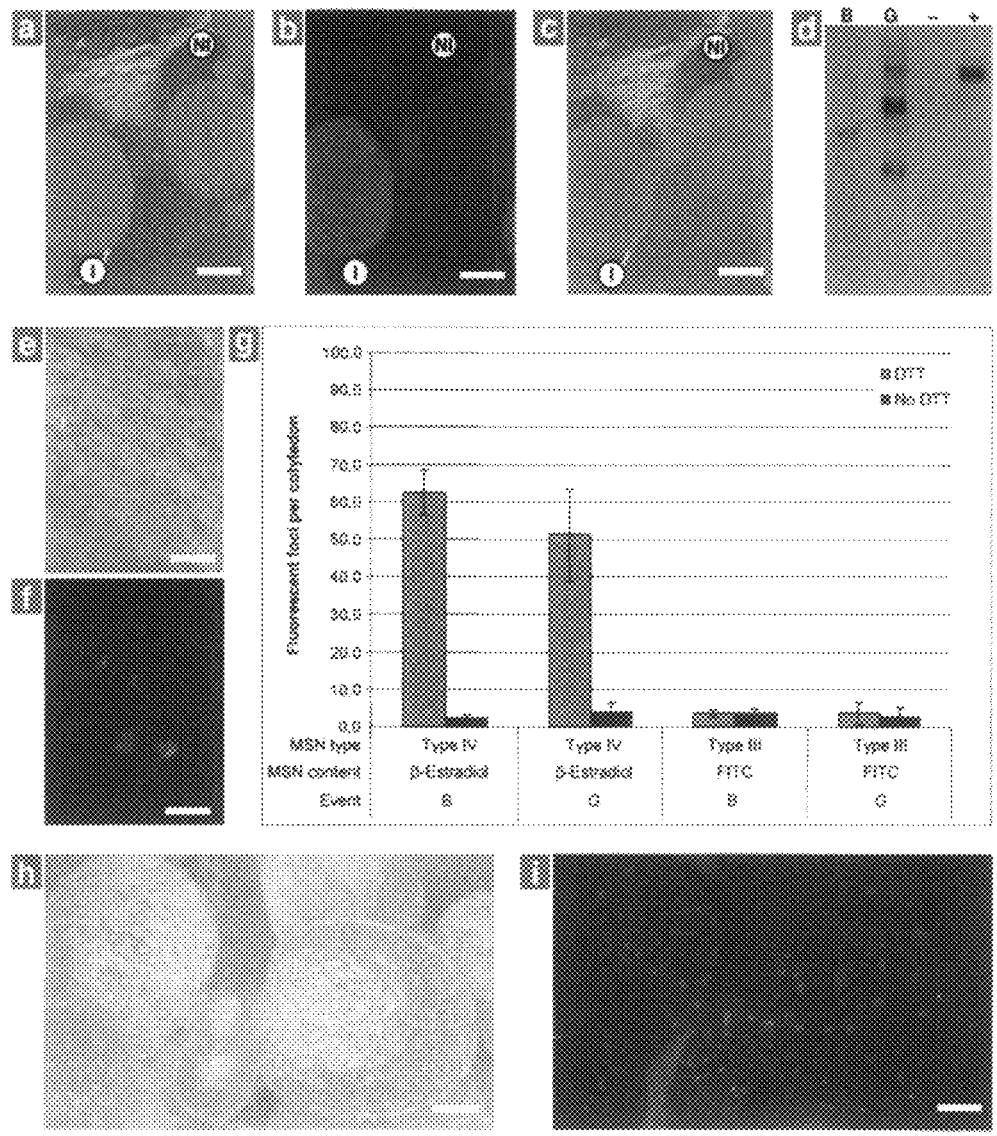
FIG. 27 shows a GFP expression in tobacco induced by MSN-mediated delivery of β-estradiol. Transgenic cotyledons grown in media with (I) or without (NI) β-estradiol, under (A) bright field, (B) UV light/GFP filter and (C) merged (bar: 2 mm). (D) Southern blot analysis of event B, and G, (−), non-transgenic plant, (+), pER8-GFP plasmid. GFP expressing cells under (E) bright field and (F) UV light/GFP filter (bar: 0.1 mm). Fluorescent foci per transgenic cotyledon (G) grown in media with (gray-bar) or without (black-bar) DTT after bombardment with MSN. Non-transgenic tobacco in DTT-medium and bombarded by DNA-coated Type-IV MSN under (H) bright field and (I) UV light/GFP filter (bar: 0.5 mm).

An average of 62.5±6.1 and 51.2±12.4 fluorescent foci was counted for the transgenic events B and G that germinated on DTT-containing plant medium, respectively (FIGS. 27E-G). Less than 5 fluorescent foci were detected on control plants germinated on medium without DTT and bombarded by Type-IV MSN, and on plants bombarded with FITC-filled Type-III MSN regardless of the germination media types. The detection of sporadic fluorescent foci on transgenic plants in the control experiments was likely due to either low level promoter leakage of this β-estradiol inducible system or stress responses caused by bombardment treatment (unpublished). No DTT-induced stresses were detectable from plants. This result indicates that a gene present in the plant genome could be activated by chemicals delivered into the cell and controlled-released subsequently in planta by using this MSN system.

Finally, to demonstrate that the MSN system can deliver both gene and chemicals that trigger gene expression simultaneously, experiments were performed in which nontransgenic plants were bombarded with β-estradiol-loaded, gold nanoparticle capped MSN coated with the inducible GFP marker gene (FIG. 23). An average of 35.6±12.8 fluorescent foci could be detected on plantlets germinated in DTT-containing medium (FIGS. 27H and I). Only a low level of background fluorescent foci (<5 foci in average) was detected in control treatments including plants that germinated in non-DTT medium and plants bombarded with FITC-filled Type-III MSN coated with the inducible GFP marker gene. This data indicates that DNA molecules carrying a marker gene and a chemical for transgene expression can be delivered simultaneously into plant cells and the encapsulated chemical regulated in a controlled manner to trigger the expression of co-delivered transgene in the cell.

Current applications of nanotechnology to biology have been mostly focused on animal science and medical research. Here, it was demonstrated that their versatility can also be applied to plant science research to aid further investigation of plant genomics and gene function as well as improvement of crop species.

Example 12

Use of MSN to Deliver siRNA and Hormones to Plant Cells and Tissues

Figure 28:
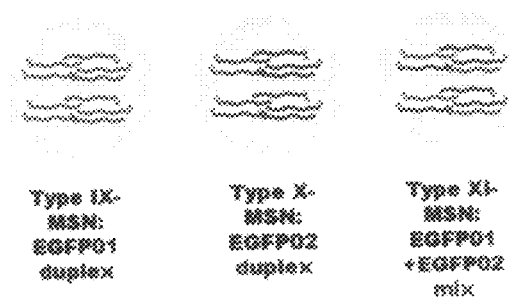
FIG. 28 illustrates MSN used for siRNA delivery.

To deliver and control siRNA delivery to plant cells, MSN were synthesized with wide pores (4.3 nm) to allow for filling with siRNA duplexes. The filled large-pore MSN were capped using gold caps and the DTT reducible hinge (FIG. 28).

Two siRNA sequences were designed to target GFP expression.

EGFP01 Duplex
Sense: r(GAG CGU ACU AUC UUC UUC A)dTdT (SEQ ID NO:1)
Antisense: r(UGA AGA AGA UAG UAC GCU C)dTdT (SEQ ID NO:2)
EGFP02 duplex
Sense: r(GCG UUC AGU UGG CUG AUC A)dTdT (SEQ ID NO:3)
Antisense: r(UGA UCA GCC AAC UGA ACG C)dTdT (SEQ ID NO:4)

To follow the siRNA loading and unloading, each stand of siRNA is labeled with rhodamine at the 5' end. A Blast analysis was performed against nr to ensure specificity:

The two strands were annealed according to the manufacturer's (Qiagen's) instructions in annealing buffer. Briefly, 1 mL of siRNA suspension buffer was added to obtain a 20 μM solution. The tube was heated at 90° C. for 1 minute and then incubated at 37° C. for 60 minutes for annealing. The annealed siRNA solution was kept at −20° C. in the dark (foil wrapped).

An equimolar mix was also prepared to maximize chances of silencing.

Target Plants

Figure 29:
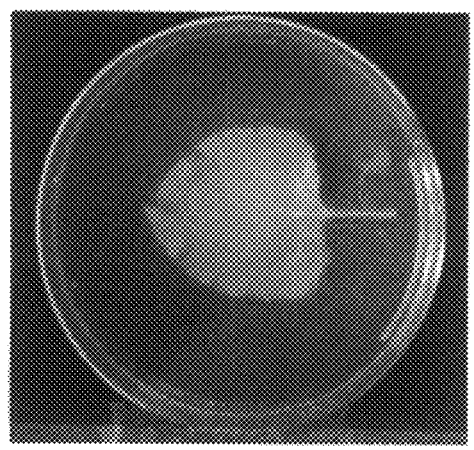
FIG. 29 shows partial overlay of UV light image (upper left part of the picture) and bright field image (lower right part of the image). The green fluorescence of the GFP is clearly visible in the large *N. benthamiana* 16c leaf whereas a red autofluorescence is seen in the small *N. tobaccum* leaf.

*Arabidopsis* plants transformed with pFT01 and pFT02, an *A. thaliana* 35S::GFP line, and a *Nicotiana benthamiana* line 16c are used. Two leaves per plant are excised and placed on G0 germination media (1×MS salts, 30 g.l sucrose, 1× MS vitamins). GFP expression was detected as a green fluorescence instead of a read chlorophyll auto-fluorescence color of the leaf in the non transgenic plants (FIG. 29).

Four types of MSN are used.
Type-IX: EGFP01 filled large pore Au-capped MSN
Type-X: EGFP02 filled large pore Au-capped MSN
Type-XI: EGFPmix filled large pore Au-capped MSN The MSN were surface sterilized by incubating them in 95% ethanol for 5 minutes and rinsing them 4 times with DEPC treated water. In the final suspension, it was observed that the MSN tend to precipitate rapidly, however, the loading could be performed aseptically without using the freeze-dryer technique. For instance, the MSN ethanol suspension (freshly sonicated) is loaded on a macrocarrier and pipeted up and down on the macrocarrier using a low retention tip, until the solution dries out.

Loaded macrocarriers were used to shoot isolated 16c plant leaves using 1100 psi rupture disks at 10 cm in distance under a 28 mm Hg vacuum.

After bombardment, all bombarded leaves were maintained in a 24° C. light incubator for 24 hours. Pictures were taken the next day to reveal any bombardment induced reaction. After 2 days on G0 media, half of the leaves were transferred on G1 media (G0+1 mM DTT). To slow fungus or bacteria formation, the plated leaves were maintained at 10° C.

Plant GFP phenotype is monitored for at least 5 weeks. By the second week, plants may be transferred into pots.

Hormone/Transgene Co-Delivery

To deliver to the same cell a transgene and a physiological signal, e.g., hormones, Type III MSN are synthesized and filled with hormones.
Type-XII: BAP (1 mM) filled Au-capped MSN
Type-XIII: 2,4D (1 mM) filled Au-capped MSN
Type-XIV: BAP/2,4D (0.5 mM each) filled Au-capped MSN
Type-XV: BAP (1 mM) filled large pore Au-capped MSN
Type-XVI: 2,4D (1 mM) filled large pore Au-capped MSN
Type-XVII: BAP/2,4D (0.5 mM each) filled large pore Au-capped MSN DTT is used as the reducing agent for controlled release of the hormones.

Plant Material

Figure 30:
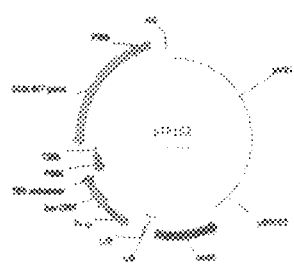
FIG. 30 illustrates pTF102 plasmid. The T-DNA contains a 2x35S CaMV promoter driving a GUS gene. The selectable marker is bar.

Six to 8 weeks old tobacco plants grown aseptically on G0 media are used. One $cm^2$ squares of leaf tissue is cut and placed face down on either G0 or G1 media. Five pieces are used per Petri dish. The MSN are coated with pTF102 plasmid (FIG. 30). Both G0 and G1 media are supplemented, after bombardment, with 3 mg/L Liberty®. After 2 weeks all explants (including the ones treated on G1 media) are re-plated on a weekly basis on G0 media+ Liberty®.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for delivering more than one agent to a plant or fungal cell, comprising:

contacting plant or fungal cells having a cell wall with an amount of a composition comprising a mesoporous silicate body having i) one or more pores which have one or more removable gold nanoparticle caps obstructing the one or more pores and a first agent in the one or more pores, which removable gold nanoparticle caps allow for controlled release of the first agent from the one or more pores and ii) a second agent coated on the surface of the silicate body, so as to deliver the first and second agents into the cells.

2. The method of claim 1 wherein the coating comprises a polymer.

3. The method of claim 2 wherein the polymer is TEG.

4. The method of claim 1 wherein the coating comprises a dendrimer.

5. The method of claim 2 wherein the polymer comprises a poly(amidoamine).

6. The method of claim 1 wherein the second agent comprises isolated nucleic acid encoding at least one gene product.

7. The method of claim 6 wherein the isolated nucleic acid comprises DNA.

8. The method of claim 7 wherein the isolated DNA is on a plasmid.

9. The method of claim 1 wherein the mesoporous silicate body is a particle from about 1 nm to about 10 microns.

10. The method of claim 1 wherein the pores are about 1 to 50 nm in diameter.

11. The method of claim 1 wherein the pores are about 1 nm to about 3 nm in diameter.

12. The method of claim 1 wherein the mesoporous silicate body is a sphere.

13. The method of claim 12 wherein the mesoporous silicate body is a sphere having a diameter of about 100 to about 300 nm.

14. The method of claim 1 wherein the mesoporous silicate body is a rod.

15. The method of claim 1 wherein the one or more caps are covalently bonded to the mesoporous silicate body.

16. The method of claim 15 wherein the one or more caps are covalently bonded to the mesoporous silicate through a linking group that comprises disulfide.

17. The method of claim 1 wherein the one or more caps are removed by contacting the mesoporous silicate body with a reducing agent.

18. The method of claim 17 wherein the reducing agent is dithiothreitol (DTT).

19. The method of claim 1 wherein the first agent comprises a hormone, an antifungal agent, an antiviral agent, or a nutrient.

20. The method of claim 1 wherein the plant cells are dicot cells.

21. The method of claim 1 wherein the plant cells are monocot cells.

22. The method of claim 1 wherein the plant cells are protoplasts.

23. The method of claim 1 wherein the composition is contacted with a plant.

24. The method of claim 1 wherein the composition is contacted with the plant cells via bombardment.

* * * * *

```
                        SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: A synthetic combined DNA/RNA sequence

<400> SEQUENCE: 1
gagcguacua ucuucuucat t                                          21

<210> SEQ ID NO 2
<211> LENGTH: 21
<212> TYPE: DNA
<213> ORGANISM: Artificial Sequence
<220> FEATURE:
<223> OTHER INFORMATION: A synthetic combined DNA/RNA sequence

<400> SEQUENCE: 2
ugaagaagau aguacgcuct t                                          21

<210> SEQ ID NO 3
<211> LENGTH: 21
<212> TYPE: DNA
<213> ORGANISM: Artificial Sequence
```

-continued

```
<220> FEATURE:
<223> OTHER INFORMATION: A synthetic combined DNA/RNA sequence

<400> SEQUENCE: 3
gcguucaguu ggcugaucat t                                            21

<210> SEQ ID NO 4
<211> LENGTH: 21
<212> TYPE: DNA
<213> ORGANISM: Artificial Sequence
<220> FEATURE:
<223> OTHER INFORMATION: A synthetic combined DNA/RNA sequence

<400> SEQUENCE: 4
ugaucagcca acugaacgct t                                            21
```